(12) United States Patent
Oh et al.

(10) Patent No.: US 10,383,859 B2
(45) Date of Patent: Aug. 20, 2019

(54) BENZO[D]THIAZOLE DERIVATIVE OR SALT THEREOF, AND PHARMACEUTICAL COMPOSITION INCLUDING SAME

(71) Applicant: Yuhan Corporation, Seoul (KR)

(72) Inventors: Se-Woong Oh, Gyeonggi-do (KR); Youn Hur, Gyeonggi-do (KR); Jin-Hwi Park, Gyeonggi-do (KR); Jae-Eun Joo, Gyeonggi-do (KR); Ho-Woong Kang, Gyeonggi-do (KR); Hyok-Jun Cho, Gyeonggi-do (KR); Eui-Chul Lee, Gyeonggi-do (KR); Chan-Sun Park, Gyeonggi-do (KR); Dong-Hyun Kim, Seoul (KR); Jong-Gyun Kim, Gyeonggi-do (KR); Su-Youn Nam, Seoul (KR)

(73) Assignee: Yuhan Corporation (KR)

( * ) Notice: Subject to any disclaimer, the term of this patent is extended or adjusted under 35 U.S.C. 154(b) by 0 days.

(21) Appl. No.: 16/315,814

(22) PCT Filed: Jul. 6, 2017

(86) PCT No.: PCT/KR2017/007201
§ 371 (c)(1),
(2) Date: Jan. 7, 2019

(87) PCT Pub. No.: WO2018/008989
PCT Pub. Date: Jan. 11, 2018

(65) Prior Publication Data
US 2019/0142809 A1 May 16, 2019

(30) Foreign Application Priority Data

Jul. 8, 2016 (KR) ........................ 10-2016-0086957

(51) Int. Cl.
C07D 277/82 (2006.01)
A61K 31/428 (2006.01)
A61P 35/04 (2006.01)
(52) U.S. Cl.
CPC ............ *A61K 31/428* (2013.01); *A61P 35/04* (2018.01); *C07D 277/82* (2013.01)
(58) Field of Classification Search
CPC .................................................. C07D 277/82
See application file for complete search history.

(56) References Cited

U.S. PATENT DOCUMENTS

2012/0283300 A1    8/2012  Kim et al.

FOREIGN PATENT DOCUMENTS

| WO | WO-02/46176 A1 * | 6/2002 | ........... C07D 277/56 |
|---|---|---|---|
| WO | 03074495 A1 | 9/2003 | |
| WO | 2006094235 A1 | 9/2006 | |
| WO | 2009126635 A1 | 10/2009 | |
| WO | 2011056021 A2 | 5/2011 | |
| WO | 2013043001 A1 | 3/2013 | |

OTHER PUBLICATIONS

A machine English translation of WO 02/46176 A1 (Yoshida et al.), 2002. (Year: 2002).*
Comess. K. M. et al., "Discovery and Characterization of Non-ATP Site Inhibitors of the Mitogen Activated Protein (MAP) Kinases", ACS Chem. Biol., 2011, vol. 6, pp. 234-244, (web publication date, Nov. 23, 2010).
Givant-Horwitz et al., "Laminin-induced signaling in tumor cells", Cancer Letters, vol. 223, Issue 1, Jun. 2005, pp. 1-10.
International Search Report for Application No. PCT/KR2017/007201 dated Oct. 19, 2017, 2 pages.
Kim et al., "Chemical inhibition of prometastatic lysyl-tRNA synthetase-laminin receptor interaction", Nat Chem Biol. Jan. 2014; 10(1): 29-34.
Ménard et al., "New insights into the metastasis-associated 67 kD Laminin Receptor", Journal of Cellular Bulcheminstry, vol. 67, Issue 2, pp. 155-165, Nov. 1997.
Nelson et al., "The 67 kDa laminin receptor: structure, function and role in disease", Biosci. Rep., Feb. 2008, vol. 28, Issue 1, pp. 33-48.

* cited by examiner

*Primary Examiner* — Laura L Stockton
(74) *Attorney, Agent, or Firm* — Lerner, David, Littenberg, Krumholz & Mentlik, LLP

(57) ABSTRACT

The present invention provides a benzo[d]thiazole derivative or its pharmaceutically acceptable salt, a process for the preparation thereof, and a pharmaceutical composition comprising the same. The benzo[d]thiazole derivative or its pharmaceutically acceptable salt can selectively inhibit the protein-protein interaction between KRS and a laminin receptor (LR), thereby inhibiting migration of cancer cells. Therefore, the benzo[d]thiazole derivative or its pharmaceutically acceptable salt may be usefully applied for preventing or treating the diseases associated with cancer cell metastasis.

8 Claims, 3 Drawing Sheets

BENZO[D]THIAZOLE DERIVATIVE OR SALT THEREOF, AND PHARMACEUTICAL COMPOSITION INCLUDING SAME

This application is a national phase entry under 35 U.S.C. § 371 of International Application No. PCT/KR2017/007201, filed Jul. 6, 2017, which claims priority to Korean Patent Application No. 10-2016-0086957, filed Jul. 8, 2016.

TECHNICAL FIELD

The present invention relates to a benzo[d]thiazole derivative or its pharmaceutically acceptable salt, a process for the preparation thereof, and a pharmaceutical composition comprising the same.

BACKGROUND ART

In general, normal cells control their division and growth precisely in the body. However, when cells lose their regulatory function or divide and grow uncontrollably, they are abnormally over-proliferated, thereby forming malignant tumors. Cancer cells may also spread to other sites in the body. That is, cancer cells growing in a primary cancer may invade neighboring tissues directly, or be metastasized to more distant parts of the body along with the blood vessel or lymphatic vessel. Since cancer cells can freely pass through both the lymphatic system and the venous system, they are broadly metastasized by their vascular spread. Blood-borne cancer cells pass through vascular endothelial cells by aggregation and invasion, thereby entering into the blood stream.

Meanwhile, 67 kDa laminin receptor (LR) is a non-integrin type receptor embedded in plasma membrane and associated with cancer invasion and metastasis (Nelson, J. et al. The 67 kDa laminin receptor: structure, function and role in disease. Biosci. Rep. 28, 33-48 (2008)). LR is often observed at high level in a various cancers (Nelson, J. et al. The 67 kDa laminin receptor: structure, function and role in disease. Biosci. Rep. 28, 33-48 (2008); Menard, S., Castronovo, V., Tagliabue, E. & Sobel, M. E. New insights into the metastasis-associated 67 kD laminin receptor. J. Cell. Biochem. 67, 155-165 (1997)). It has been reported that the laminin signals mediated by LR induce cancer progress and metastasis, through various signaling pathways associated with a G protein, FAK, MAPK, a phosphatase, a phospholipase D, etc (Cancer Letter, 2005).

Recently, it was found that Lysyl-tRNA-synthetases (KRS), one of the aminoacyl-tRNA synthetases (ARSs), bind to laminin receptor (LR) so as to stabilize the laminin receptor (LR). That is, it was reported that KRS facilitates cell migration and cancer metastasis by stabilizing the laminin receptor (LR) and that KRS over-expression leads to increase in metastasis (WO 2011/056021). And also, it was reported that inhibition of the binding between KRS and the LR protein degrades the LR protein, thereby inhibiting cell migration and leading to the inhibition of cancer metastasis in animal models (Nature Chemical Biology, 2014, 10: 29-34).

Therefore, it is expected that a material inhibiting or blocking the interaction between KRS and LR can inhibit or block cancer metastasis, thereby usefully applying to prevention and treatment of cancer.

DETAILED DESCRIPTION OF THE INVENTION

Technical Problem

The present inventors found that a benzo[d]thiazole derivative or its pharmaceutically acceptable salt can selectively inhibit the protein-protein interaction between KRS and LR, thereby inhibiting migration of cancer cells, and therefore can be usefully applied for preventing or treating the diseases associated with cancer cell metastasis.

Therefore, the present invention provides said benzo[d]thiazole derivative or its pharmaceutically acceptable salt, a process for the preparation thereof, and a pharmaceutical composition comprising the same.

Technical Solution

According to an aspect of the present invention, there is provided a benzo[d]thiazole derivative or its pharmaceutically acceptable salt.

According to another aspect of the present invention, there is provided a process for preparing said compound or its pharmaceutically acceptable salt.

According to still another aspect of the present invention, there is provided a pharmaceutical composition for preventing or treating a disease associated with cancer cell metastasis, comprising said compound or its pharmaceutically acceptable salt as an active ingredient.

Advantageous Effects

The compound of the present invention, i.e., the benzo[d]thiazole derivative or its pharmaceutically acceptable salt, can selectively inhibit the protein-protein interaction between KRS and LR, without affecting the KRS's innate function (i.e., protein synthesis function of the KRS), thereby inhibiting migration of cancer cells.

Therefore, the benzo[d]thiazole derivative or its pharmaceutically acceptable salt may be usefully applied for preventing or treating the diseases associated with cancer cell metastasis.

BEST MODE FOR CARRYING OUT THE INVENTION

Figure 1:
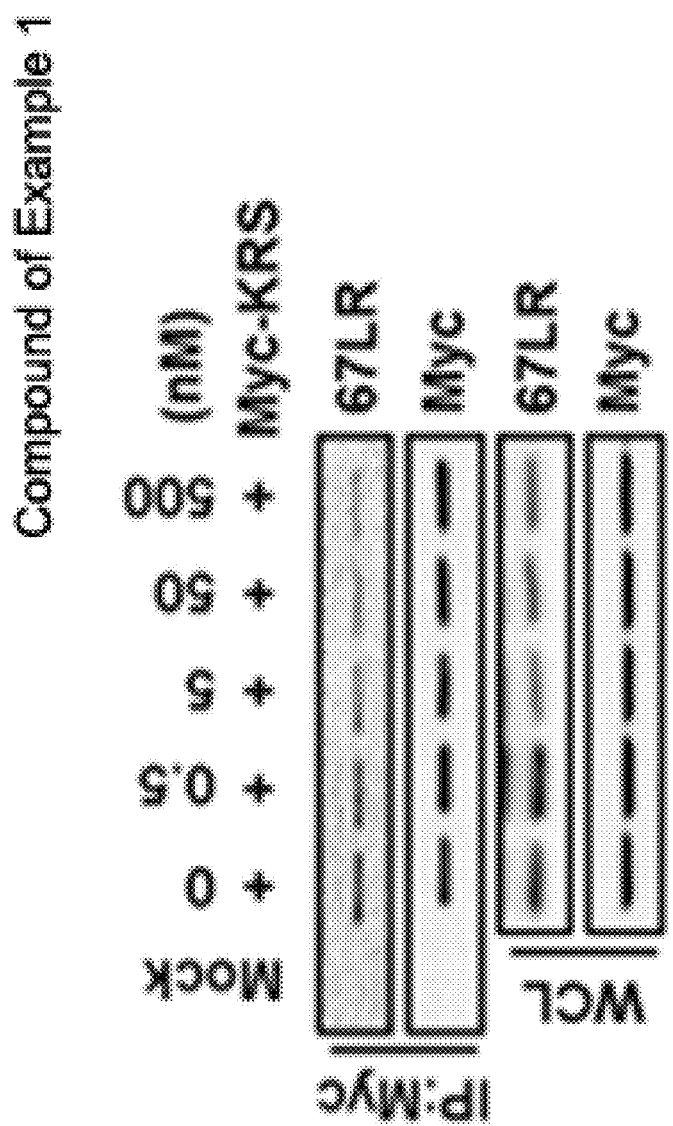
FIGS. 1 to 3 show the results obtained by measuring inhibitions against the protein-protein interaction between KRS and LR, through western blotting assays, when the compounds of Example 1 (FIG. 1), Example 83 (FIG. 2), and Example 93 (FIG. 3) were treated in predetermined concentrations.

As used herein, the term "alkyl" refers to a straight or branched aliphatic hydrocarbon radical. For example, $C_1$~$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "alkoxy" refers to a radical formed by substituting the hydrogen atom of a hydroxyl group with an alkyl. For example, $C_1$~$C_6$ alkoxy includes methoxy, ethoxy, propoxy, n-butoxy, n-pentyloxy, isopropoxy, sec-butoxy, tert-butoxy, neopentyloxy, and isopentyloxy.

The present invention provides a compound of Formula 1 or its pharmaceutically acceptable salt:

<Formula 1>

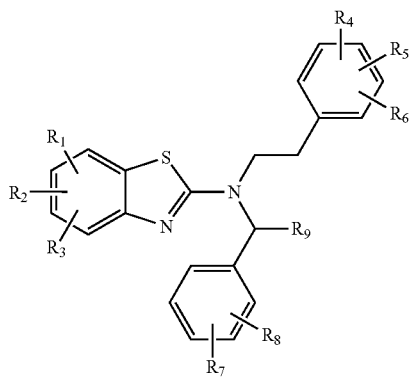

wherein, $R_1$, $R_2$, and $R_3$ are, independently of each other, hydrogen; a halogen group; a nitro group; an amino group; a $C_1$~$C_6$ alkyl group optionally substituted with halogen; or a hydroxycarbonyl group (with the proviso that $R_1$, $R_2$, and $R_3$ are not hydrogen at the same time), $R_4$, $R_5$, and $R_6$ are, independently of each other, hydrogen; a halogen group; a $C_1$~$C_6$ alkyl group; a $C_1$~$C_6$ alkoxy group optionally substituted with $C_3$~$C_6$ cycloalkyl; a $C_1$~$C_6$ alkylsulfanyl group; or a mono- or di-$C_1$~$C_6$ alkylamino group, $R_7$ and $R_8$ are, independently of each other, hydrogen; a hydroxy group; a halogen group; or a hydroxycarbonyl group (with the proviso that $R_7$ and $R_8$ are not hydrogen at the same time), and $R_9$ is hydrogen or a $C_1$~$C_6$ alkyl group.

Preferably, the compound or its pharmaceutically acceptable salt of the present invention may be a compound or its pharmaceutically acceptable salt, wherein $R_1$, $R_2$, and $R_3$ are, independently of each other, hydrogen; or a halogen group (with the proviso that $R_1$, $R_2$, and $R_3$ are not hydrogen at the same time), $R_4$, $R_5$, and $R_6$ are, independently of each other, hydrogen; a halogen group; or a $C_1$~$C_6$ alkoxy group (with the proviso that $R_4$, $R_5$, and $R_6$ are not hydrogen at the same time), $R_7$ and $R_8$ are, independently of each other, hydrogen; or a hydroxycarbonyl group (with the proviso that $R_7$ and $R_8$ are not hydrogen at the same time), and $R_9$ is hydrogen or a $C_1$~$C_6$ alkyl group.

Examples of preferable compounds or its salts in the compound or its pharmaceutically acceptable salt of the present invention includes:

4-({(7-fluorobenzo[d]thiazol-2-yl)[2-(4-methoxyphenyl)ethyl]amino}methyl)benzoic acid;
4-(((2-chlorophenylethyl)(7-fluorobenzo[d]thiazol-2-yl)amino)methyl)benzoic acid;
4-({(7-fluorobenzo[d]thiazol-2-yl)[2-(3-fluorophenyl)ethyl]amino}methyl)benzoic acid;
4-{[[2-(4-chlorophenyl)ethyl](7-fluorobenzo[d]thiazol-2-yl)amino]methyl}benzoic acid;
4-{[[2-(3-chlorophenyl)ethyl](7-fluorobenzo[d]thiazol-2-yl)amino]methyl}benzoic acid;
4-(((7-fluorobenzo[d]thiazol-2-yl)(4-methylphenylethyl)amino)methyl)benzoic acid;
4-({(7-fluorobenzo[d]thiazol-2-yl)[2-(3-methoxyphenyl)ethyl]amino}methyl)benzoic acid;
4-({(7-fluorobenzo[d]thiazol-2-yl)[2-(4-fluorophenyl)ethyl]amino}methyl)benzoic acid;
4-{[[2-(4-ethoxyphenyl)ethyl](7-fluorobenzo[d]thiazol-2-yl)amino]methyl}benzoic acid;
4-({(7-fluorobenzo[d]thiazol-2-yl)[2-(4-propoxyphenyl)ethyl]amino}methyl)benzoic acid;
4-({(7-fluorobenzo[d]thiazol-2-yl)[2-(4-isopropoxyphenyl)ethyl]amino}methyl)benzoic acid;
4-{[(7-fluorobenzo[d]thiazol-2-yl){2-[4-(methylsulfanyl)phenyl]ethyl}amino]methyl}benzoic acid;
4-{[(7-fluorobenzo[d]thiazol-2-yl){2-[3-(methylsulfanyl)phenyl]ethyl}amino]methyl}benzoic acid;
4-({[2-(2,5-dimethoxyphenyl)ethyl](7-fluorobenzo[d]thiazol-2-yl)amino}methyl)benzoic acid;
4-({[2-(3,4-dimethoxyphenyl)ethyl](7-fluorobenzo[d]thiazol-2-yl)amino}methyl)benzoic acid;
4-({(7-fluorobenzo[d]thiazol-2-yl)[2-(2-methoxyphenyl)ethyl]amino}methyl)benzoic acid;
4-({(7-fluorobenzo[d]thiazol-2-yl)[2-(3-methylphenyl)ethyl]amino}methyl)benzoic acid;
4-({(7-fluorobenzo[d]thiazol-2-yl)[2-(4-isobutoxyphenyl)ethyl]amino}methyl)benzoic acid;
4-{[[2-(4-cyclopropylmethoxyphenyl)ethyl](7-fluorobenzo[d]thiazol-2-yl)amino]methyl}benzoic acid;
4-{[(7-fluorobenzo[d]thiazol-2-yl){2-[4-(methylamino)phenyl]ethyl}amino]methyl}benzoic acid;
4-{[{2-[4-(dimethylamino)phenyl]ethyl}(7-fluorobenzo[d]thiazol-2-yl)amino]methyl}benzoic acid;
4-{[(7-fluorobenzo[d]thiazol-2-yl)(2-phenylethyl)amino]methyl}benzoic acid;
4-{[[2-(4-cyclohexylmethoxyphenyl)ethyl]-(7-fluorobenzo[d]thiazol-2-yl)amino]methyl}benzoic acid;
4-{[[2-(4-cyclobutylmethoxyphenyl)ethyl]-(7-fluorobenzo[d]thiazol-2-yl)amino]methyl}benzoic acid;
4-({[2-(4-ethoxy-3-methoxyphenyl)ethyl](7-fluorobenzo[d]thiazol-2-yl)amino}methyl)benzoic acid;
4-({(7-fluorobenzo[d]thiazol-2-yl)[2-(2-fluoro-4-methoxyphenyl)ethyl]amino}methyl)benzoic acid;
4-({[2-(2,4-dimethoxyphenyl)ethyl](7-fluorobenzo[d]thiazol-2-yl)amino}methyl)benzoic acid;
4-({(7-fluorobenzo[d]thiazol-2-yl)[2-(3-fluoro-4-methoxyphenyl)ethyl]amino}methyl)benzoic acid;
4-({[2-(3-chloro-4-methoxyphenyl)ethyl](7-fluorobenzo[d]thiazol-2-yl)amino}methyl)benzoic acid;
4-{[[2-(4-sec-butoxyphenyl)ethyl](7-fluorobenzo[d]thiazol-2-yl)amino]methyl}benzoic acid;
4-{[[2-(4-ethylaminophenyl)ethyl](7-fluorobenzo[d]thiazol-2-yl)amino]methyl}benzoic acid;
4-({[2-(4-ethylphenyl)ethyl](7-fluorobenzo[d]thiazol-2-yl)amino}methyl)benzo acid;
4-{[(7-fluorobenzo[d]thiazol-2-yl){2-[4-(propan-2-yl)phenyl]ethyl}amino]methyl}benzoic acid;
4-({[2-(2,3-difluorophenyl)ethyl](7-fluorobenzo[d]thiazol-2-yl)amino}methyl)benzoic acid;
4-({[2-(2,5-difluorophenyl)ethyl](7-fluorobenzo[d]thiazol-2-yl)amino}methyl)benzoic acid;
4-({(7-fluorobenzo[d]thiazol-2-yl)[2-(3,4,5-trifluorophenyl)ethyl]amino}methyl)benzoic acid;
4-({[2-(3-bromo-4-methoxyphenyl)ethyl](7-fluorobenzo[d]thiazol-2-yl)amino}methyl)benzoic acid;
4-({[2-(2,4-dichlorophenyl)ethyl](7-fluorobenzo[d]thiazol-2-yl)amino}methyl)benzoic acid;
4-({[2-(2,4-difluorophenyl)ethyl](7-fluorobenzo[d]thiazol-2-yl)amino}methyl)benzoic acid;
4-({(7-fluorobenzo[d]thiazol-2-yl)[2-(2-methoxyphenyl)ethyl]amino}methyl)benzoic acid;
4-({(7-fluorobenzo[d]thiazol-2-yl)[2-(2-fluorophenyl)ethyl]amino}methyl)benzoic acid;

4-({(7-fluorobenzo[d]thiazol-2-yl)[2-(3-methoxyphenyl)ethyl]amino}methyl)benzoic acid;

4-({[2-(2,3-difluoro-4-methoxyphenyl)ethyl](7-fluorobenzo[d]thiazol-2-yl)amino}methyl)benzoic acid;

4-{[(7-fluorobenzo[d]thiazol-2-yl){2-[4-methoxy-2-methyl-5-(propan-2-yl)phenyl]ethyl}amino]methyl}benzoic acid;

4-({[2-(2,5-difluoro-4-methoxyphenyl)ethyl](7-fluorobenzo[d]thiazol-2-yl)amino}methyl)benzoic acid;

4-({[2-(2-chloro-4-methoxyphenyl)ethyl](7-fluorobenzo[d]thiazol-2-yl)amino}methyl)benzoic acid;

4-({(7-fluorobenzo[d]thiazol-2-yl)[2-(4-methoxy-2,3-dimethylphenyl)ethyl]amino}methyl)benzoic acid;

4-({(7-fluorobenzo[d]thiazol-2-yl)[2-(4-methoxy-2,5-dimethylphenyl)ethyl]amino}methyl)benzoic acid;

4-({(7-fluorobenzo[d]thiazol-2-yl)[2-(4-methoxy-3-methylphenyl)ethyl]amino}methyl)benzoic acid;

4-({(7-fluorobenzo[d]thiazol-2-yl)[2-(4-methoxy-2-methylphenyl)ethyl]amino}methyl)benzoic acid;

4-({[2-(2,6-difluoro-4-methoxyphenyl)ethyl](7-fluorobenzo[d]thiazol-2-yl)amino}methyl)benzoic acid;

4-(1-{(7-fluorobenzo[d]thiazol-2-yl)[2-(4-methoxyphenyl)ethyl]amino}ethyl)benzoic acid;

4-(1-{(7-fluorobenzo[d]thiazol-2-yl)[2-(4-methoxyphenyl)ethyl]amino}propyl)benzoic acid;

4-(1-{(7-fluorobenzo[d]thiazol-2-yl)[2-(3-fluoro-4-methoxyphenyl)ethyl]amino}ethyl)benzoic acid;

4-(1-{[2-(3-bromo-4-methoxyphenyl)ethyl](7-fluorobenzo[d]thiazol-2-yl)amino}ethyl)benzoic acid;

4-(1-{[2-(2,4-difluorophenyl)ethyl](7-fluorobenzo[d]thiazol-2-yl)amino}ethyl)benzoic acid;

4-(1-{[2-(2,3-difluorophenyl)ethyl](7-fluorobenzo[d]thiazol-2-yl)amino}ethyl)benzoic acid;

4-(1-{(7-fluorobenzo[d]thiazol-2-yl)[2-(3,4,5-trifluorophenyl)ethyl]amino}ethyl)benzoic acid;

4-(1-{[2-(2,4-dichlorophenyl)ethyl](7-fluorobenzo[d]thiazol-2-yl)amino}ethyl)benzoic acid;

4-(1-{[2-(2,3-difluoro-4-methoxyphenyl)ethyl](7-fluorobenzo[d]thiazol-2-yl)amino}ethyl)benzoic acid;

4-(1-{[2-(2,5-difluoro-4-methoxyphenyl)ethyl](7-fluorobenzo[d]thiazol-2-yl)amino}ethyl)benzoic acid;

4-{1-[(7-fluorobenzo[d]thiazol-2-yl){2-[4-methoxy-2-methyl-5-(propan-2-yl)phenyl]ethyl}amino]ethyl}benzoic acid;

4-(1-{(7-fluorobenzo[d]thiazol-2-yl)[2-(4-methoxy-2,3-dimethylphenyl)ethyl]amino}ethyl)benzoic acid;

4-(1-{(7-fluorobenzo[d]thiazol-2-yl)[2-(4-methoxy-2,5-dimethylphenyl)ethyl]amino}ethyl)benzoic acid;

4-(1-{(7-fluorobenzo[d]thiazol-2-yl)[2-(4-methoxy-3-methylphenyl)ethyl]amino}ethyl)benzoic acid;

4-(1-{(7-fluorobenzo[d]thiazol-2-yl)[2-(4-methoxy-2-methylphenyl)ethyl]amino}ethyl)benzoic acid;

4-(1-{[2-(2,6-difluoro-4-methoxyphenyl)ethyl](7-fluorobenzo[d]thiazol-2-yl)amino}ethyl)benzoic acid;

4-(1-{[2-(2,3-difluoro-4-methoxyphenyl)ethyl](7-fluorobenzo[d]thiazol-2-yl)amino}propyl)benzoic acid;

4-(1-{[2-(2,5-difluoro-4-methoxyphenyl)ethyl](7-fluorobenzo[d]thiazol-2-yl)amino}propyl)benzoic acid;

4-(1-{[2-(2-chloro-4-methoxyphenyl)ethyl](7-fluorobenzo[d]thiazol-2-yl)amino}propyl)benzoic acid;

4-(1-{(7-fluorobenzo[d]thiazol-2-yl)[2-(4-methoxy-2,3-dimethylphenyl)ethyl]amino}propyl)benzoic acid;

4-(1-{(7-fluorobenzo[d]thiazol-2-yl)[2-(4-methoxy-2,5-dimethylphenyl)ethyl]amino}propyl)benzoic acid;

4-(1-{(7-fluorobenzo[d]thiazol-2-yl)[2-(4-methoxy-3-methylphenyl)ethyl]amino}propyl)benzoic acid;

4-(1-{(7-fluorobenzo[d]thiazol-2-yl)[2-(4-methoxy-2-methylphenyl)ethyl]amino}propyl)benzoic acid;

4-(1-{[2-(2,6-difluoro-4-methoxyphenyl)ethyl](7-fluorobenzo[d]thiazol-2-yl)amino}propyl)benzoic acid;

4-{1-[(7-fluorobenzo[d]thiazol-2-yl){2-[4-methoxy-2-methyl-5-(propan-2-yl)phenyl]ethyl}amino]propyl}benzoic acid;

4-({(7-fluorobenzo[d]thiazol-2-yl)[2-(4-methoxyphenyl)ethyl]amino}methyl)-2 hydroxybenzoic acid;

3-chloro-4-({(7-fluorobenzo[d]thiazol-2-yl)[2-(4-methoxyphenyl)ethyl]amino}methyl)benzoic acid;

4-({[2-(4-methoxyphenyl)ethyl](6-nitro-benzo[d]thiazol-2-yl)amino}methyl)benzoic acid;

4-({[2-(4-methoxyphenyl)ethyl](7-nitro-benzo[d]thiazol-2-yl)amino}methyl)benzoic acid;

4-({(6-amino-benzo[d]thiazol-2-yl)[2-(4-methoxyphenyl)ethyl]amino}methyl)benzoic acid;

4-({(7-amino-benzo[d]thiazol-2-yl)[2-(4-methoxyphenyl)ethyl]amino}methyl)benzoic acid;

4-({(7-chloro-benzo[d]thiazol-2-yl)[2-(4-methoxyphenyl)ethyl]amino}methyl)benzoic acid;

4-({(6-chloro-benzo[d]thiazol-2-yl)[2-(4-methoxyphenyl)ethyl]amino}methyl)benzoic acid;

4-({(5-chloro-benzo[d]thiazol-2-yl)[2-(4-methoxyphenyl)ethyl]amino}methyl)benzoic acid;

4-({(5,6-difluorobenzo[d]thiazol-2-yl)[2-(4-methoxyphenyl)ethyl]amino}methyl)benzoic acid;

4-{[[2-(4-methoxyphenyl)ethyl](5,6,7-trifluorobenzo[d]thiazol-2-yl)amino]methyl}benzoic acid;

4-({(6-chloro-7-fluorobenzo[d]thiazol-2-yl)[2-(4-methoxyphenyl)ethyl]amino}methyl)benzoic acid;

4-{[[2-(4-methoxyphenyl)ethyl](7-trifluoromethyl-benzo[d]thiazol-2-yl)amino]methyl}benzoic acid;

4-({(6,7-difluorobenzo[d]thiazol-2-yl)-[2-(4-methoxyphenyl)ethyl]amino}methyl)benzoic acid;

4-({(5-bromo-benzo[d]thiazol-2-yl)[2-(4-methoxyphenyl)ethyl]amino}methyl)benzoic acid;

4-({(6-fluorobenzo[d]thiazol-2-yl)[2-(4-methoxyphenyl)ethyl]amino}methyl)benzoic acid;

4-({(5,7-difluorobenzo[d]thiazol-2-yl)[2-(4-methoxyphenyl)ethyl]amino}methyl)benzoic acid;

4-({(7-fluoro-6-methyl-benzo[d]thiazol-2-yl)[2-(4-methoxyphenyl)ethyl]amino}methyl)benzoic acid;

4-({(4,6-difluorobenzo[d]thiazol-2-yl)[2-(4-methoxyphenyl)ethyl]amino}methyl)benzoic acid;

4-({[2-(4-methoxyphenyl)ethyl](7-methyl-benzo[d]thiazol-2-yl)amino}methyl)benzoic acid;

4-({[2-(4-methoxyphenyl)ethyl](6-methyl-benzo[d]thiazol-2-yl)amino}methyl)benzoic acid;

4-({[2-(4-methoxyphenyl)ethyl](5-methyl-benzo[d]thiazol-2-yl)amino}methyl)benzoic acid;

4-(1-{(5,7-difluorobenzo[d]thiazol-2-yl)[2-(4-methoxyphenyl)ethyl]amino}ethyl)benzoic acid;

4-(1-{(5,6-difluorobenzo[d]thiazol-2-yl)[2-(4-methoxyphenyl)ethyl]amino}ethyl)benzoic acid;

4-(1-{[2-(4-methoxyphenyl)ethyl](5,6,7-trifluorobenzo[d]thiazol-2-yl)amino}ethyl)benzoic acid;

4-(1-{(6-chloro-7-fluorobenzo[d]thiazol-2-yl)[2-(4-methoxyphenyl)ethyl]amino}ethyl)benzoic acid;

4-(1-{(5-bromo-benzo[d]thiazol-2-yl)[2-(4-methoxyphenyl)ethyl]amino}ethyl)benzoic acid;

4-(1-{(6,7-difluorobenzo[d]thiazol-2-yl)[2-(4-methoxyphenyl)ethyl]amino}ethyl)benzoic acid;

4-(1-{(7-fluoro-6-methyl-benzo[d]thiazol-2-yl)[2-(4-methoxyphenyl)ethyl]amino}ethyl)benzoic acid;

4-{1-{[2-(4-methoxyphenyl)ethyl][7-(trifluoromethyl)-benzo[d]thiazol-2-yl]amino}ethyl)benzoic acid;

4-(1-{(5-chloro-benzo[d]thiazol-2-yl)[2-(4-methoxyphenyl) ethyl]amino}ethyl)benzoic acid;
4-(1-{(6-chloro-benzo[d]thiazol-2-yl)[2-(4-methoxyphenyl) ethyl]amino}ethyl)benzoic acid;
4-(1-{(7-chloro-benzo[d]thiazol-2-yl)[2-(4-methoxyphenyl) ethyl]amino}ethyl)benzoic acid;
4-(1-{[2-(4-methoxyphenyl)ethyl](7-methyl-benzo[d]thiazol-2-yl)amino}ethyl)benzoic acid;
4-(1-{[2-(4-methoxyphenyl)ethyl](6-methyl-benzo[d]thiazol-2-yl)amino}ethyl)benzoic acid;
4-(1-{[2-(4-methoxyphenyl)ethyl](5-methyl-benzo[d]thiazol-2-yl)amino}ethyl)benzoic acid;
4-(1-{(5-fluorobenzo[d]thiazol-2-yl)[2-(4-methoxyphenyl) ethyl]amino}ethyl)benzoic acid;
4-(1-{(4,6-difluorobenzo[d]thiazol-2-yl)[2-(4-methoxyphenyl)ethyl]amino}ethyl)benzoic acid;
4-({(6-bromo-benzo[d]thiazol-2-yl)[2-(4-methoxyphenyl) ethyl]amino}methyl)benzoic acid;
4-(1-{(6-bromo-benzo[d]thiazol-2-yl)[2-(4-methoxyphenyl)ethyl]amino}ethyl)benzoic acid;
2-{(4-carboxybenzyl)[2-(4-methoxyphenyl)ethyl] amino}benzo[d]thiazole-6-carboxylic acid;
2-{(4-carboxybenzyl)[2-(4-methoxyphenyl)ethyl] amino}benzo[d]thiazole-7-carboxylic acid;
4-({[2-(4-methoxyphenyl)ethyl][6-(trifluoromethyl)benzo [d]thiazol-2-yl]amino}methyl)benzoic acid;
4-({[2-(4-methoxyphenyl)ethyl][5-(trifluoromethyl)benzo [d]thiazol-2-yl]amino}methyl)benzoic acid;
4-({[7-fluoro-6-(trifluoromethyl)benzo[d]thiazol-2-yl][2-(4-methoxyphenyl)ethyl]amino}methyl)benzoic acid;
4-(1-{(5,7-difluorobenzo[d]thiazol-2-yl)[2-(3-fluoro-4-methoxyphenyl)ethyl]amino}ethyl)benzoic acid;
4-(1-{[2-(4-methoxyphenyl)ethyl][6-(trifluoromethyl) benzo[d]thiazol-2-yl]amino}ethyl)benzoic acid;
4-(1-{[2-(4-methoxyphenyl)ethyl][5-(trifluoromethyl) benzo[d]thiazol-2-yl]amino}ethyl)benzoic acid; and
4-(1-{[7-fluoro-6-(trifluoromethyl)benzo[d]thiazol-2-yl][2-(4-methoxyphenyl)ethyl]amino}ethyl)benzoic acid.

Examples of more preferable compounds or its salts in the compound or its pharmaceutically acceptable salt of the present invention includes:
4-({(7-fluorobenzo[d]thiazol-2-yl)[2-(4-methoxyphenyl) ethyl]amino}methyl)benzoic acid;
4-(((2-chlorophenylethyl)(7-fluorobenzo[d]thiazol-2-yl) amino)methyl)benzoic acid;
4-(((7-fluorobenzo[d]thiazol-2-yl)(4-methylphenylethyl) amino)methyl)benzoic acid;
4-{[[2-(4-ethoxyphenyl)ethyl](7-fluorobenzo[d]thiazol-2-yl)amino]methyl}benzoic acid;
4-{[(7-fluorobenzo[d]thiazol-2-yl){2-[4-(methylsulfanyl) phenyl]ethyl}amino]methyl}benzoic acid;
4-{[(7-fluorobenzo[d]thiazol-2-yl){2-[3-(methylsulfanyl) phenyl]ethyl}amino]methyl}benzoic acid;
4-({[2-(3,4-dimethoxyphenyl)ethyl](7-fluorobenzo[d]thiazol-2-yl)amino}methyl)benzoic acid;
4-{[[2-(4-cyclopropylmethoxyphenyl)ethyl](7-fluorobenzo[d]thiazol-2-yl)amino]methyl}benzoic acid;
4-{[(7-fluorobenzo[d]thiazol-2-yl){2-[4-(methylamino)phenyl]ethyl}amino]methyl}benzoic acid;
4-{[{2-[4-(dimethylamino)phenyl]ethyl}(7-fluorobenzo[d] thiazol-2-yl)amino]methyl}benzoic acid;
4-({(7-fluorobenzo[d]thiazol-2-yl)[2-(2-fluoro-4-methoxyphenyl)ethyl]amino}methyl)benzoic acid;
4-({(7-fluorobenzo[d]thiazol-2-yl)[2-(3-fluoro-4-methoxyphenyl)ethyl]amino}methyl)benzoic acid;
4-({[2-(3-chloro-4-methoxyphenyl)ethyl](7-fluorobenzo[d] thiazol-2-yl)amino}methyl)benzoic acid;
4-({[2-(4-ethylphenyl)ethyl](7-fluorobenzo[d]thiazol-2-yl) amino}methyl)benzo acid;
4-({[2-(2,3-difluoro-4-methoxyphenyl)ethyl](7-fluorobenzo [d]thiazol-2-yl)amino}methyl)benzoic acid;
4-({[2-(2,5-difluoro-4-methoxyphenyl)ethyl](7-fluorobenzo [d]thiazol-2-yl)amino}methyl)benzoic acid;
4-({(7-fluorobenzo[d]thiazol-2-yl)[2-(4-methoxy-2,5-dimethylphenyl)ethyl]amino}methyl)benzoic acid;
4-({(7-fluorobenzo[d]thiazol-2-yl)[2-(4-methoxy-3-methylphenyl)ethyl]amino}methyl)benzoic acid;
4-({(7-fluorobenzo[d]thiazol-2-yl)[2-(4-methoxy-2-methylphenyl)ethyl]amino}methyl)benzoic acid;
4-({[2-(2,6-difluoro-4-methoxyphenyl)ethyl](7-fluorobenzo [d]thiazol-2-yl)amino}methyl)benzoic acid;
4-(1-{(7-fluorobenzo[d]thiazol-2-yl)[2-(4-methoxyphenyl) ethyl]amino}ethyl)benzoic acid;
4-(1-{(7-fluorobenzo[d]thiazol-2-yl)[2-(4-methoxyphenyl) ethyl]amino}propyl)benzoic acid;
4-(1-{[2-(2,3-difluoro-4-methoxyphenyl)ethyl](7-fluorobenzo[d]thiazol-2-yl)amino}ethyl)benzoic acid;
4-(1-{[2-(2,5-difluoro-4-methoxyphenyl)ethyl](7-fluorobenzo[d]thiazol-2-yl)amino}ethyl)benzoic acid;
4-(1-{(7-fluorobenzo[d]thiazol-2-yl)[2-(4-methoxy-2,3-dimethylphenyl)ethyl]amino}ethyl)benzoic acid;
4-(1-{(7-fluorobenzo[d]thiazol-2-yl)[2-(4-methoxy-2,5-dimethylphenyl)ethyl]amino}ethyl)benzoic acid;
4-(1-{(7-fluorobenzo[d]thiazol-2-yl)[2-(4-methoxy-3-methylphenyl)ethyl]amino}ethyl)benzoic acid;
4-(1-{(7-fluorobenzo[d]thiazol-2-yl)[2-(4-methoxy-2-methylphenyl)ethyl]amino}ethyl)benzoic acid;
4-(1-{[2-(2,6-difluoro-4-methoxyphenyl)ethyl](7-fluorobenzo[d]thiazol-2-yl)amino}ethyl)benzoic acid;
4-(1-{[2-(2,3-difluoro-4-methoxyphenyl)ethyl](7-fluorobenzo[d]thiazol-2-yl)amino}propyl)benzoic acid;
4-({(7-fluorobenzo[d]thiazol-2-yl)[2-(4-methoxyphenyl) ethyl]amino}methyl)-2 hydroxybenzoic acid;
3-chloro-4-({(7-fluorobenzo[d]thiazol-2-yl)[2-(4-methoxyphenyl)ethyl]amino}methyl)benzoic acid;
4-({[2-(4-methoxyphenyl)ethyl](6-nitro-benzo[d]thiazol-2-yl)amino}methyl)benzoic acid;
4-({[2-(4-methoxyphenyl)ethyl](7-nitro-benzo[d]thiazol-2-yl)amino}methyl)benzoic acid;
4-({(6-amino-benzo[d]thiazol-2-yl)[2-(4-methoxyphenyl) ethyl]amino}methyl)benzoic acid;
4-({(7-amino-benzo[d]thiazol-2-yl)[2-(4-methoxyphenyl) ethyl]amino}methyl)benzoic acid;
4-({(7-chloro-benzo[d]thiazol-2-yl)[2-(4-methoxyphenyl) ethyl]amino}methyl)benzoic acid;
4-({(6-chloro-benzo[d]thiazol-2-yl)[2-(4-methoxyphenyl) ethyl]amino}methyl)benzoic acid;
4-({(5-chloro-benzo[d]thiazol-2-yl)[2-(4-methoxyphenyl) ethyl]amino}methyl)benzoic acid;
4-({(5,6-difluorobenzo[d]thiazol-2-yl)[2-(4-methoxyphenyl)ethyl]amino}methyl)benzoic acid;
4-{[[2-(4-methoxyphenyl)ethyl](5,6,7-trifluorobenzo[d]thiazol-2-yl)amino]methyl}benzoic acid;
4-({(6-chloro-7-fluorobenzo[d]thiazol-2-yl)[2-(4-methoxyphenyl)ethyl]amino}methyl)benzoic acid;

4-{[[2-(4-methoxyphenyl)ethyl](7-trifluoromethyl-benzo[d]thiazol-2-yl)amino]methyl}benzoic acid;
4-({(6,7-difluorobenzo[d]thiazol-2-yl)-[2-(4-methoxyphenyl)ethyl]amino}methyl)benzoic acid;
4-({(5-bromo-benzo[d]thiazol-2-yl)[2-(4-methoxyphenyl)ethyl]amino}methyl)benzoic acid;
4-({(6-fluorobenzo[d]thiazol-2-yl)[2-(4-methoxyphenyl)ethyl]amino}methyl)benzoic acid;
4-({(5,7-difluorobenzo[d]thiazol-2-yl)[2-(4-methoxyphenyl)ethyl]amino}methyl)benzoic acid;
4-({(7-fluoro-6-methyl-benzo[d]thiazol-2-yl)[2-(4-methoxyphenyl)ethyl]amino}methyl)benzoic acid;
4-({(4,6-difluorobenzo[d]thiazol-2-yl)[2-(4-methoxyphenyl)ethyl]amino}methyl)benzoic acid;
4-(1-{(7-chloro-benzo[d]thiazol-2-yl)[2-(4-methoxyphenyl)ethyl]amino}ethyl)benzoic acid;
4-({[2-(4-methoxyphenyl)ethyl][5-(trifluoromethyl)benzo[d]thiazol-2-yl]amino}methyl)benzoic acid;
4-(1-{(5,7-difluorobenzo[d]thiazol-2-yl)[2-(3-fluoro-4-methoxyphenyl)ethyl]amino}ethyl)benzoic acid; and
4-(1-{[2-(4-methoxyphenyl)ethyl][5-(trifluoromethyl)benzo[d]thiazol-2-yl]amino}ethyl)benzoic acid.

Examples of especially preferable compounds or its salts in the compound or its pharmaceutically acceptable salt of the present invention includes:
4-({(7-fluorobenzo[d]thiazol-2-yl)[2-(4-methoxyphenyl)ethyl]amino}methyl)benzoic acid;
4-({(7-chloro-benzo[d]thiazol-2-yl)[2-(4-methoxyphenyl)ethyl]amino}methyl)benzoic acid; and
4-({(5,7-difluorobenzo[d]thiazol-2-yl)[2-(4-methoxyphenyl)ethyl]amino}methyl)benzoic acid.

The compound of Formula 1 or its pharmaceutically acceptable salt may have substituents containing asymmetric carbon and therefore be in the form of racemic mixture (RS) or in forms of optical isomers, such as (R) or (S) isomer. The compound of Formula 1 or its pharmaceutically acceptable salt comprises both racemic mixture (RS) and optical isomers such as (R) or (S) isomer, unless otherwise indicated.

The compound of Formula 1 of the present invention may be in a pharmaceutically acceptable salt form. The salt may be an acid addition salt form, which includes e.g., salts derived from an inorganic acid such as hydrochloric acid, hydrobromic acid, sulfuric acid, or phosphoric acid; and salts derived from an organic acid such as citric acid, acetic acid, lactic acid, tartaric acid, maleic acid, fumaric acid, formic acid, propionic acid, oxalic acid, trifluoroacetic acid, benzoic acid, glucuronic acid, methanesulfonic acid, glycolic acid, succinic acid, p-toluenesulfonic acid, glutamic acid, or aspartic acid. And also, the pharmaceutically acceptable salt may be a metal salt form, which includes e.g., salts derived from an alkali metal such as lithium, sodium, or potassium; or an alkali earth metal such as calcium or magnesium. The matal salt form also includes a chrome salt. In addition, the pharmaceutically acceptable salt may be an organic ligand-derived salt, e.g., quarternary ammonium salt; an amine salt, e.g., dicyclohexylamine salt or N-methyl-D-glucamine salt; or an amino acid salt derived from arginine, lysine, etc.

The present invention also provides a process for preparing a compound of Formula 1a or 1b or its pharmaceutically acceptable salt, which comprises reacting a compound of Formula 2 with a compound of Formula 3 to obtain a compound of Formula 4; reacting the compound of Formula 4 with a compound of Formula 5 to obtain a compound of Formula 1a; and optionally hydrolyzing the compound of Formula 1a to obtain a compound of Formula 1b, as shown in the following Reaction Scheme 1:

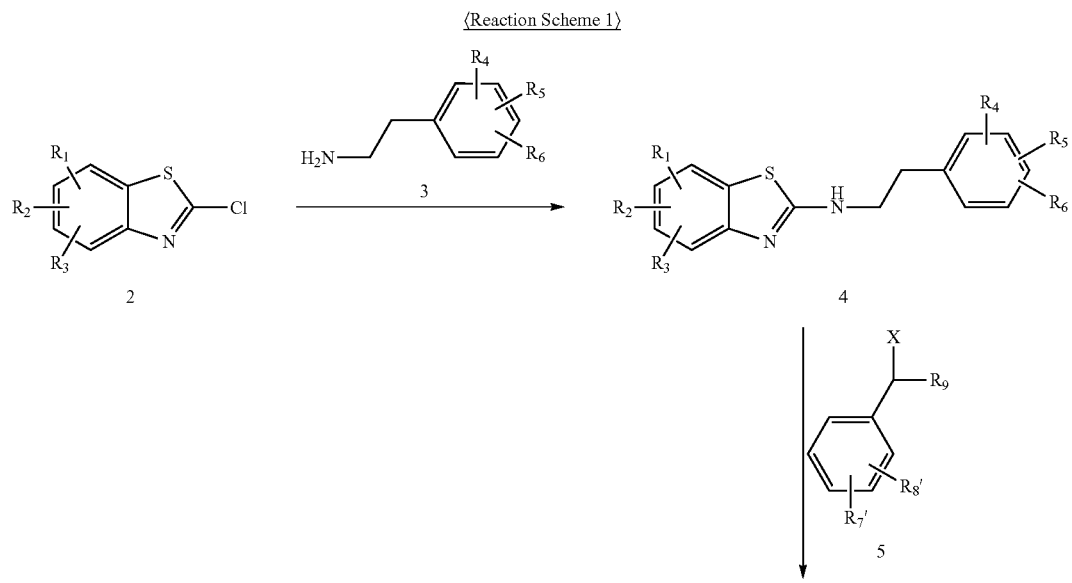

-continued

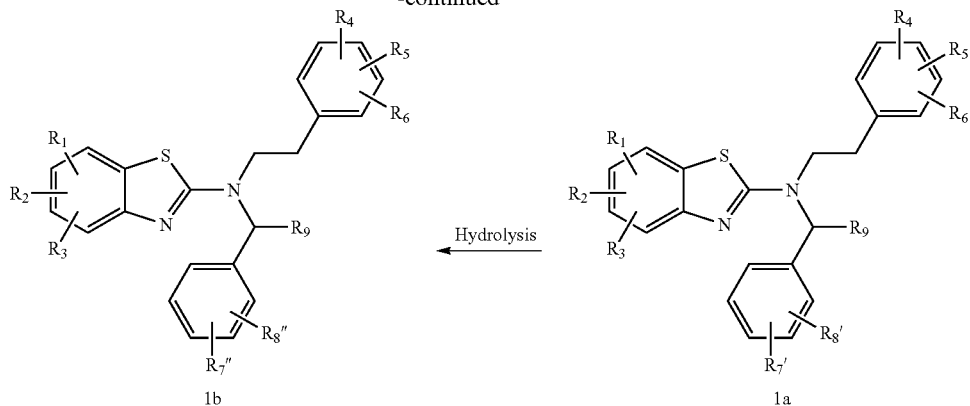

1b          1a

Hydrolysis

In the Reaction Scheme 1, $R_1$, $R_2$, $R_3$, $R_4$, $R_5$, $R_6$, and $R_9$ are the same as defined in the above. $R_7'$ and $R_7''$ are hydrogen; a hydroxy group; or a halogen group, $R_8'$ is a $C_1$~$C_6$ alkoxycarbonyl group, and $R_8''$ is a hydroxycarbonyl group.

The compound of Formula 2 is commercially available and may be prepared according to a known method (for example, Armitage, Bruce A. et al., Journal of the American Chemical Society, 2007(129), 5710; Gavin W. Stewart, Journal of Organic Chemistry, 2009(74), 3229). In addition, the compound of Formula 3 is also commercially available.

The reaction of the compound of Formula 2 and the compound of Formula 3 may be carried out in the presence of a base. The base includes an alkali metal salt or an organic base. Said alkali metal salt includes potassium carbonate, cesium carbonate, sodium hydroxide, sodium bicarbonate, etc. Said organic base includes pyridine, triethylamine, N,N-dimethylaniline, diisopropylethylamine, DBU (1,8-diazabicycloundec-7-ene), etc. The amount of the base to be used is not particularly limited. For example, the base may be used in ratio ranging from 1 to 3 equivalents based on 1 equivalent of the compound of Formula 2. And also, the compound of Formula 3 may be used in a ratio ranging from 1 to 5 equivalents based on 1 equivalent of the compound of Formula 2, but not limited thereto. Said reaction may be carried out in a solvent such as dimethylformamide, tetrahydrofuran, N,N-dimethylformamide, etc. at 0° C. to 80° C. for 10 minutes to 12 hours. And also, said reaction, i.e., the reaction for C—N bond formation, may be performed according to known methods such as a coupling reaction, an addition reaction, a Buchwald-Hartwig reaction, or a substitution reaction (For example, Verma, Sanjeev K., RCS advances, 2013(3), 18783).

The reaction of the compound of Formula 4 and the compound of Formula 5 is a reaction of nucleophilic substitution. Preferably, the reaction may be performed in the presence of a base. The base includes an inorganic base such as potassium carbonate ($K_2CO_3$), cesium carbonate ($Cs_2CO_3$), sodium tert-butoxide (tert-BuONa), potassium tert-butoxide (tert-BuOK), or sodium hydride (NaH). The reaction may be performed in a solvent including a non-polar organic solvent such as benzene, toluene, etc.; or a polar organic solvent such as N,N-dimethylformamide, acetonitrile, dioxane, tetrahydrofuran, etc. Typically, the reaction may be carried out at 0 to 150° C., preferably 40 to 120° C.

The hydrolysis of the compound of Formula 1a may be performed under alkaline condition, using sodium hydroxide, lithium hydroxide, potassium hydroxide, etc. And also, said hydrolysis may be performed in water or a mixed solvent of water and a polar solvent (e.g., tetrahydrofuran, ethanol, etc.) as a solvent. Typically, the reaction may be carried out at room temperature to 50° C.

The present invention also provides an inhibitor against cancer cell metastasis, comprising a therapeutically effective amount of the compound of Formula 1 or its pharmaceutically acceptable salt as an active ingredient. The therapeutically effective amount refers to an amount sufficient for providing an inhibitory activity against cancer cell metastasis. For example, the therapeutically effective amount may be from about 1 mg/kg to about 300 mg/kg per day. Of course, the therapeutically effective amount may be changed according to the patient's age, weight, susceptibility, symptom, or activity of the compound.

And also, the present invention provides a pharmaceutical composition for preventing or treating a disease associated with cancer cell metastasis, comprising a therapeutically effective amount of the compound of Formula 1 or its pharmaceutically acceptable salt; and a pharmaceutically acceptable carrier. The disease associated with cancer cell metastasis may be selected from the group consisting of colon cancer, lung cancer, hepatic cancer, gastric cancer, esophageal cancer, pancreatic cancer, gallbladder cancer, kidney cancer, bladder cancer, prostate cancer, testicular cancer, cervical cancer, endometrial cancer, choriocarcinoma, ovarian cancer, breast cancer, thyroid cancer, brain tumor, head and neck cancer, malignant melanoma, lymphoma, and aplastic anemia, but not limited thereto.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as injection, according to conventional methods. The dosage form may be various forms, e.g., dosage forms for single administration or for multiple administrations.

The pharmaceutical composition of the present invention may comprise, for example, a diluent (e.g., lactose, corn starch, etc); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The compound of Formula 1 or its pharmaceutically acceptable salt may be administered in a therapeutically effective amount ranging from about 1 mg/kg to about 300 mg/kg per day to a subject patient. Of course, the dosage may be changed according to the patient's age, weight, susceptibility, symptom, or activity of the compound.

The following examples and experimental examples are provided for illustration purposes only, and are not intended to limit the scope of the invention.

The analyses of the compounds prepared in the following Examples were carried out as follows: Nuclear magnetic resonance (NMR) spectrum analysis was carried out using Bruker 400 MHz spectrometer and chemical shifts thereof were analyzed in ppm. LCMS analysis was carried out using Agilent 1260 Infinity. Column chromatography was carried out on silica gel (Merck, 70-230 mesh) (W. C. Still, *J. Org. Chem.*, 1978 (43), 2923-2925). The starting materials in each Example are known compounds, which were synthesized according literatures or obtained from Sigma-Aldrich.

Example 1. 4-({(7-fluorobenzo[d]thiazol-2-yl)[2-(4-methoxyphenyl)ethyl]amino}methyl)benzoic acid Step 1: 7-fluorobenzo[d]thiazol-2-thiol 2,3-Difluoroaniline (100.0 g, 0.774 mol) and potassium ethyl xanthogenate (273.0 g, 1.702 mol) were dissolved in anhydrous dimethylformamide (1000 ml), followed by stirring at 95° C. for 4 hours. After confirming through TLC analysis that the starting materials disappeared, the reaction mixture was cooled to room temperature. Water (750 ml) and a 3N HCl solution (750 ml) were added to the reaction mixture to generate a solid precipitate. The reaction mixture was further stirred for 30 minutes and then filtered under reduced pressure. The resulting solid precipitate was washed with water, dissolved in toluene (900 ml) and then subject to Dean-Stark distillation overnight. The resulting solution was cooled to room temperature. The resulting white solid filtered under reduced pressure was dried to obtain the titled compound (95 g).

Step 2: 2-chloro-7-fluorobenzo[d]thiazole

A flask was charged with sulfuryl chloride (120 ml) and stirred in an ice bath. 7-Fluorobenzo[d]thiazol-2-thiol (90.0 g) prepared in Step 1 was slowly added thereto, while the temperature of the reaction mixture was adjusted to room temperature or lower. After the addition, the temperature of the reaction mixture was raised to room temperature and then stirred for 2 hours. After confirming through TLC analysis that the starting materials disappeared, the reaction mixture was poured into ice water and then further stirred for 2 hours. The reaction mixture was extracted with ethyl acetate and then washed with brine. The organic layer was washed with a saturated sodium bicarbonate solution, dried over magnesium sulfate, and then filtered under reduced pressure. The resulting organic solution was concentrated to obtaining a liquid, which was used in the next step without further purification.

Step 3: 7-fluoro-2-((4-methoxyphenylethyl)amino) benzo[d]thiazole

4-Methoxyphenylethylamine (32.2 g) was dissolved in dimethylformamide (40 ml) and then DBU (32.4 mmol) was added thereto. After the reaction mixture was stirred for 30 minutes, 2-chloro-7-fluorobenzo[d]thiazole (40 g, 0.213 mol) prepared in Step 2 was slowly added to the reaction mixture, using a dropping funnel. After the reaction mixture was stirred at room temperature for 2 hours, water (150 ml) was poured into the reaction mixture and then a 3N hydrochloric acid solution (300 ml) was added thereto. The resulting aqueous suspension was filtered under reduced pressure and then washed with diisopropyl ether. The resulting solid was dried in a 50° C. vacuum oven to obtain the titled compound (63 g) as a white solid.

Step 4: methyl 4-(((7-fluorobenzo[d]thiazol-2-yl)(4-methoxyphenylethyl)amino)methyl)benzoate After 7-fluoro-2-((4-methoxyphenylethyl)amino)benzo[d]thiazole (6.3 g, 19.6 mmol) prepared in Step 3 was dissolved in dimethylformamide (100 ml), cesium carbonate (30.0 g) and methyl 4-(bromomethyl)benzoate (5.4 g) were added thereto. The reaction mixture was stirred at room temperature overnight, diluted with ethyl acetate, and then washed with water. The separated organic layer was dried over magnesium sulfate, filtered under reduced pressure, and then concentrated. The resulting residue was purified with silica gel column chromatography (eluent: ethyl acetate/n-hexane=1/4, v/v) to give 5.5 g of the titled compound as pale yellow solid.

Rf=0.55 (EA:Hex=1:3)

Step 5: 4-({(7-fluorobenzo[d]thiazol-2-yl)-[2-(4-methoxyphenyl)-ethyl]-amino}-methyl)-benzoic acid After methyl 4-(((7-fluorobenzo[d]thiazol-2-yl)(4-methoxyphenylethyl)amino)methyl)benzoate (5.0 g) prepared in Step 4 was dissolved in a mixed solvent of tetrahydrofuran (7.5 ml) and methanol (7.5 mL), a 1N sodium hydroxide solution (15.0 mL) was slowly added thereto. The reaction mixture was stirred at room temperature overnight. Water (10.0 ml) was added to the reaction mixture, which was concentrated to remove the organic solvent and then washed with diethyl ether. The organic layer was discarded. By slowly adding a 1N hydrochloric acid solution, the pH of the water layer was adjusted to about pH 3. The resulting water layer was extracted twice with ethyl acetate. The combined organic layer was washed with brine, dried over magnesium sulfate, filtered under reduced pressure, concentrated and then recrystallized with diisopropyl ether to give 3.0 g of the titled compound as white solid.
$^1$H NMR (400 MHz, CDCl$_3$) 8.07 (d, 2H), 7.35 (t, 3H), 7.26 (m, 1H), 7.11 (d, 2H), 6.84 (d, 3H), 4.72 (s, 2H), 3.79 (t, 3H), 3.67 (t, 2H), 2.95 (t, 2H).

Example 2. 4-(((2-chlorophenylethyl)(7-fluorobenzo[d]thiazol-2-yl)amino)methyl)benzoic acid The titled compound was prepared in accordance with the same procedures as in Example 1, using 2-chlorophenylethylamine instead of 4-methoxyphenylethylamine used in Step 3 of Example 1.
$^1$H NMR (400 MHz, CDCl$_3$) 8.01-8.11 (m, 2H), 7.56 (br d, J=7.83 Hz, 2H), 7.50 (br t, J=8.84 Hz, 1H), 7.25-7.42 (m, 7H), 6.84 (t, J=8.72 Hz, 1H), 4.73 (s, 2H), 3.76 (br t, J=7.45 Hz, 2H), 3.08 (br t, J=7.45 Hz, 2H).

Example 3. 4-({(7-fluorobenzo[d]thiazol-2-yl)[2-(3-fluorophenyl)ethyl]amino}methyl)benzoic acid The titled compound was prepared in accordance with the same procedures as in Example 1, using 3-fluorophenylethylamine instead of 4-methoxyphenylethylamine used in Step 3 of Example 1.
$^1$H NMR (400 MHz, CD$_3$OD) 7.90 (d, 2H), 7.30 (d, 3H), 7.21 (m, 3H), 6.85 (m, 4H), 4.71 (s, 2H), 3.70 (t, 2H), 2.94 (t, 2H).

Example 4. 4-{[[2-(4-chlorophenyl)ethyl](7-fluorobenzo[d]thiazol-2-yl)amino]methyl}benzoic acid The titled compound was prepared in accordance with the same procedures as in Example 1, using 4-chlorophenylethylamine instead of 4-methoxyphenylethylamine used in Step 3 of Example 1.
$^1$H NMR (400 MHz, CD$_3$OD) 8.01 (d, 2H), 7.41 (d, 2H), 7.28 (m, 3H), 6.88 (t, 1H), 4.82 (s, 2H), 3.80 (t, 2H), 3.04 (t, 2H).

Example 5. 4-{[[2-(3-chlorophenyl)ethyl](7-fluorobenzo[d]thiazol-2-yl)amino]methyl}benzoic acid The titled compound was prepared in accordance with the same procedures as in Example 1, using 3-chlorophenylethylamine instead of 4-methoxyphenylethylamine used in Step 3 of Example 1.
$^1$H NMR (400 MHz, CD$_3$OD) 8.02 (d, 2H), 7.41 (d, 2H), 7.27 (m, 5H), 6.87 (t, 1H), 4.83 (s, 2H), 3.82 (t, 2H), 3.04 (t, 2H).

Example 6. 4-(((7-fluorobenzo[d]thiazol-2-yl)(4-methylphenylethyl)amino)methyl)benzoic acid The titled compound was prepared in accordance with the same procedures as in Example 1, using 4-methylphenylethylamine instead of 4-methoxyphenylethylamine used in Step 3 of Example 1.
$^1$H NMR (400 MHz, CDCl$_3$) 8.04 (d, J=8.34 Hz, 2H), 7.31-7.52 (m, 3H), 7.27-7.31 (m, 1H), 7.00-7.18 (m, 4H), 6.83 (t, J=8.72 Hz, 1H), 4.73 (s, 2H), 3.68 (t, J=7.58 Hz, 2H), 2.97 (t, J=7.58 Hz, 2H), 2.33 (s, 3H).

Example 7. 4-({(7-fluorobenzo[d]thiazol-2-yl)[2-(3-methoxyphenyl)ethyl]amino}methyl)benzoic acid The titled compound was prepared in accordance with the same procedures as in Example 1, using 3-methoxyphenylethylamine instead of 4-methoxyphenylethylamine used in Step 3 of Example 1.

LCMS (m/z) 437.2 (M+H)+;
$^1$H NMR (400 MHz, CD$_3$OD) 8.01 (d, 2H), 7.35 (m, 4H), 7.16 (d, 2H), 6.86 (m, 3H), 4.79 (s, 2H), 3.75 (m, 5H), 2.97 (t, 2H).

Example 8. 4-({(7-fluorobenzo[d]thiazol-2-yl)[2-(4-fluorophenyl)ethyl]amino}methyl)benzoic acid The titled compound was prepared in accordance with the same procedures as in Example 1, using 4-fluorophenylethylamine instead of 4-methoxyphenylethylamine used in Step 3 of Example 1.
$^1$H NMR (400 MHz, CD$_3$OD) 8.00 (d, 2H), 7.33 (m, 4H), 7.21 (t, 1H), 6.83 (m, 4H), 4.78 (s, 2H), 3.78 (m, 5H), 3.00 (t, 2H).

Example 9. 4-{[[2-(4-ethoxyphenyl)ethyl](7-fluorobenzo[d]thiazol-2-yl)amino]methyl}benzoic acid The titled compound was prepared in accordance with the same procedures as in Example 1, using 4-ethoxyphenylethylamine instead of 4-methoxyphenylethylamine used in Step 3 of Example 1.
LCMS (m/z) 451.1 (M+H)+;
$^1$H NMR (400 MHz, CDCl$_3$) 12.05 (br. s, 1H), 7.98-8.11 (m, 2H), 7.22-7.44 (m, 4H), 7.03-7.15 (m, 2H), 6.77-6.89 (m, 3H), 4.71 (s, 2H), 3.95-4.15 (m, 2H), 3.67 (t, J=7.33 Hz, 2H), 2.94 (t, J=7.33 Hz, 2H), 1.33-1.47 (m, 3H).

Example 10. 4-({(7-fluorobenzo[d]thiazol-2-yl)[2-(4-propoxyphenyl)ethyl]amino}methyl)benzoic acid The titled compound was prepared in accordance with the same procedures as in Example 1, using 4-(n-propoxy)phenylethylamine instead of 4-methoxyphenylethylamine used in Step 3 of Example 1.
LCMS (m/z) 465.1 (M+H)+;
$^1$H NMR (400 MHz, CDCl$_3$) 12.14 (br. s, 1H), 8.04 (m, 2H), 7.20-7.40 (m, 4H), 7.08 (m, 2H), 6.83 (m, 3H), 4.71 (m, 2H), 3.88 (m, 2H), 3.67 (m, 2H), 2.94 (br. s, 2H), 1.77 (m, 2H), 1.02 (m, 3H).

Example 11. 4-({(7-fluorobenzo[d]thiazol-2-yl)[2-(4-isopropoxyphenyl)ethyl]amino}methyl)benzoic acid The titled compound was prepared in accordance with the same procedures as in Example 1, using 4-isopropoxyphenylethylamine instead of 4-methoxyphenylethylamine used in Step 3 of Example 1.
LCMS (m/z) 465.2 (M+H)+;
$^1$H NMR (400 MHz, CDCl$_3$) 12.36 (br. s, 1H), 7.98-8.07 (m, 2H), 7.40 (m, 1H), 7.20-7.35 (m, 3H), 7.03-7.13 (m, 2H), 6.76-6.86 (m, 3H), 4.72 (m, 2H), 4.48 (m, 1H), 3.63-3.72 (m, 2H), 2.93 (m, 2H), 1.23-1.35 (m, 6H).

Example 12. 4-{[(7-fluorobenzo[d]thiazol-2-yl){2-[4-(methylsulfanyl)phenyl]ethyl}amino]methyl}benzoic acid The titled compound was prepared in accordance with the same procedures as in Example 1, using 4-methylthiophenylethylamine instead of 4-methoxyphenylethylamine used in Step 3 of Example 1.
LCMS (m/z) 453 (M+H)+;
$^1$H NMR (400 MHz, CD$_3$OD) 7.99 (d, J=8.34 Hz, 2H), 7.38 (d, J=8.34 Hz, 2H), 7.24-7.35 (m, 2H), 7.10-7.23 (m, 4H), 6.85 (t, J=8.41 Hz, 1H), 4.78 (s, 2H), 3.75 (t, J=7.45 Hz, 2H), 2.98 (t, J=7.33 Hz, 2H), 2.42 (s, 3H).

Example 13. 4-{[(7-fluorobenzo[d]thiazol-2-yl){2-[3-(methylsulfanyl)phenyl]ethyl}amino] methyl}benzoic acid The titled compound was prepared in accordance with the same procedures as in Example 1, using 3-methylthiophenylethylamine instead of 4-methoxyphenylethylamine used in Step 3 of Example 1.

LCMS (m/z) 453 (M+H)+;
$^1$H NMR (400 MHz, CD$_3$OD), 8.00 (d, J=8.08 Hz, 2H), 7.38 (d, J=8.34 Hz, 2H), 7.26-7.34 (m, 2H), 7.18-7.24 (m, 1H), 7.08-7.14 (m, 2H), 7.01 (d, J=7.58 Hz, 1H), 6.81-6.89 (m, 1H), 4.78 (s, 2H), 3.79 (t, J=7.33 Hz, 2H), 3.00 (t, J=7.20 Hz, 2H), 2.41 (s, 3H).

Example 14. 4-({[2-(2,5-dimethoxyphenyl)ethyl](7-fluorobenzo[d]thiazol-2-yl)amino}methyl)benzoic acid The titled compound was prepared in accordance with the same procedures as in Example 1, using 2,5-dimethoxyphenylethylamine instead of 4-methoxyphenylethylamine used in Step 3 of Example 1.

$^1$H NMR (400 MHz, DMSO-d$_6$), 12.95 (s, 1H), 7.93 (d, 2H), 7.43 (d, 2H), 7.31 (d, 2H), 6.81-6.72 (m, 2H), 4.87 (s, 2H), 3.75 (s, 3H), 3.66 (s, 5H), 2.92 (t, 2H).

Example 15. 4-({[2-(3,4-dimethoxyphenyl)ethyl](7-fluorobenzo[d]thiazol-2-yl)amino}methyl)benzoic acid The titled compound was prepared in accordance with the same procedures as in Example 1, using 3,4-dimethoxyphenylethylamine instead of 4-methoxyphenylethylamine used in Step 3 of Example 1.

$^1$H NMR (400 MHz, DMSO-d$_6$), 12.95 (s, 1H), 7.93 (d, 2H), 7.43 (d, 2H), 7.37-7.25 (m, 2H), 7.01-6.91 (m, 1H), 6.90-6.83 (m, 2H), 6.77 (d, 1H), 4.86 (s, 2H), 3.88-3.58 (m, 8H), 2.91 (t, 2H).

Example 16. 4-({(7-fluorobenzo[d]thiazol-2-yl)[2-(2-methoxyphenyl)ethyl]amino}methyl)benzoic acid The titled compound was prepared in accordance with the same procedures as in Example 1, using 2-methoxyphenylethylamine instead of 4-methoxyphenylethylamine used in Step 3 of Example 1.

LCMS (m/z) 437.1 (M+H)+;
$^1$H NMR (400 MHz, CDCl$_3$) 7.97 (d, J=8.08 Hz, 2H), 7.29-7.34 (m, 1H), 7.11-7.24 (m, 3H), 7.05 (d, J=7.33 Hz, 1H), 6.71-6.84 (m, 3H), 4.74 (s, 2H), 3.74 (s, 3H), 3.42-3.65 (m, 2H), 2.95 (br t, J=7.58 Hz, 2H).

Example 17. 4-({(7-fluorobenzo[d]thiazol-2-yl)[2-(3-methylphenyl)ethyl]amino}methyl)benzoic acid The titled compound was prepared in accordance with the same procedures as in Example 1, using 3-methylphenylethylamine instead of 4-methoxyphenylethylamine used in Step 3 of Example 1.

$^1$H NMR (400 MHz, CDCl$_3$) 8.03 (br d, J=7.83 Hz, 2H), 7.16-7.41 (m, 5H), 6.95-7.07 (m, 3H), 6.82 (t, J=8.72 Hz, 1H), 4.73 (s, 2H), 3.69 (br t, J=7.45 Hz, 2H), 2.96 (br t, J=7.58 Hz, 2H), 2.32 (s, 3H).

Example 18. 4-({(7-fluorobenzo[d]thiazol-2-yl)[2-(4-isobutoxyphenyl)ethyl]amino}methyl)benzoic acid The titled compound was prepared in accordance with the same procedures as in Example 1, using 4-isobutoxyphenylethylamine instead of 4-methoxyphenylethylamine used in Step 3 of Example 1.

LCMS (m/z) 479.2 (M+H)+;
$^1$H NMR (400 MHz, CDCl$_3$) 7.96-8.13 (m, 2H), 7.21-7.44 (m, 5H), 7.09 (m, 2H), 6.74-6.94 (m, 3H), 4.72 (s, 2H), 3.60-3.78 (m, 4H), 2.88-3.04 (m, 2H), 2.00-2.18 (m, 1H), 0.97-1.08 (m, 6H).

Example 19. 4-{[[2-(4-cyclopropylmethoxyphenyl) ethyl](7-fluorobenzo[d]thiazol-2-yl)amino] methyl}benzoic acid The titled compound was prepared in accordance with the same procedures as in Example 1, using 4-cyclopropylmethoxyphenylethylamine instead of 4-methoxyphenylethylamine used in Step 3 of Example 1.

LCMS (m/z) 477.2 (M+H)+;
$^1$H NMR (400 MHz, CDCl$_3$) 10.26 (br. s, 1H), 8.00-8.09 (m, 2H), 7.40 (m, 1H), 7.22-7.36 (m, 3H), 7.04-7.13 (m, 2H), 6.79-6.88 (m, 3H), 4.72 (s, 2H), 3.64-3.83 (m, 4H), 2.94 (m, 2H), 1.20-1.31 (m, 1H), 0.54-0.73 (m, 2H), 0.28-0.41 (m, 2H).

Example 20. 4-{[(7-fluorobenzo[d]thiazol-2-yl){2-[4-(methylamino)phenyl]ethyl}amino] methyl}benzoic acid The titled compound was prepared in accordance with the same procedures as in Example 1, using 4-methylaminophenylethylamine instead of 4-methoxyphenylethylamine used in Step 3 of Example 1.

$^1$H NMR (400 MHz, DMSO-d$_6$) 12.97 (s, 1H), 7.92 (d, 2H), 7.43 (d, 2H), 7.34-7.29 (m, 2H), 7.02-6.91 (m, 3H), 6.47 (d, 2H), 4.85 (s, 2H), 3.65 (t, 2H), 2.81 (t, 2H), 2.63 (s, 3H).

Example 21. 4-{[{2-[4-(dimethylamino)phenyl] ethyl}(7-fluorobenzo[d]thiazol-2-yl)amino] methyl}benzoic acid The titled compound was prepared in accordance with the same procedures as in Example 1, using 4-dimethylaminophenylethylamine instead of 4-methoxyphenylethylamine used in Step 3 of Example 1.

$^1$H NMR (400 MHz, DMSO-d$_6$) 12.95 (s, 1H), 7.92 (d, 2H), 7.43 (d, 2H), 7.36-7.25 (m, 2H), 7.07 (d, 2H), 7.01-6.91 (m, 1H), 6.67 (d, 2H), 4.86 (s, 2H), 3.67 (t, 2H), 2.91-2.79 (m, 6H).

Example 22. 4-{[(7-fluorobenzo[d]thiazol-2-yl)(2-phenylethyl)amino]methyl}benzoic acid The titled compound was prepared in accordance with the same procedures as in Example 1, using phenylethylamine instead of 4-methoxyphenylethylamine used in Step 3 of Example 1.

¹H NMR (400 MHz, DMSO-d$_6$) 12.95 (s, 1H), 7.93 (d, 2H), 7.44 (d, 2H), 7.38-7.25 (m, 6H), 7.23 (d, 1H), 6.95 (q, 1H), 4.87 (s, 2H), 3.77 (t, 2H), 2.99 (t, 2H).

Example 23. 4-{[[2-(4-cyclohexylmethoxyphenyl) ethyl]-(7-fluorobenzo[d]thiazol-2-yl)amino] methyl}benzoic acid The titled compound was prepared in accordance with the same procedures as in Example 1, using 4-cyclohexyl-methoxyphenylethylamine instead of 4-methoxyphenylethylamine used in Step 3 of Example 1.
LCMS (m/z) 519.2 (M+H)+;
¹H NMR (400 MHz, CDCl$_3$) 8.04 (m, 2H), 7.22-7.41 (m, 4H), 7.03-7.13 (m, 2H), 6.77-6.87 (m, 3H), 4.72 (br s, 2H), 3.63-3.78 (m, 4H), 2.94 (m, 2H), 1.86 (m, 2H), 1.71-1.80 (m, 4H), 1.13-1.36 (m, 3H), 0.98-1.10 (m, 2H).

Example 24. 4-{[[2-(4-cyclobutylmethoxyphenyl) ethyl]-(7-fluorobenzo[d]thiazol-2-yl)amino] methyl}benzoic acid The titled compound was prepared in accordance with the same procedures as in Example 1, using 4-cyclobutyl-methoxyphenylethylamine instead of 4-methoxyphenylethylamine used in Step 3 of Example 1.
LCMS (m/z) 491.2 (M+H)+;
¹H NMR (400 MHz, CDCl$_3$) 10.49 (br s, 1H), 8.03 (m, 2H), 7.22-7.43 (m, 4H), 7.03-7.15 (m, 2H), 6.78-6.89 (m, 3H), 4.71 (s, 2H), 3.89 (m, 2H), 3.67 (m, 2H), 2.88-3.00 (m, 2H), 2.69-2.81 (m, 1H), 2.07-2.18 (m, 3H), 1.80-2.06 (m, 4H).

Example 25. 4-({[2-(4-ethoxy-3-methoxyphenyl) ethyl](7-fluorobenzo[d]thiazol-2-yl)amino}methyl) benzoic acid The titled compound was prepared in accordance with the same procedures as in Example 1, using 4-ethoxy-3-methoxyphenylethylamine instead of 4-methoxyphenylethylamine used in Step 3 of Example 1.
LCMS (m/z) 481 (M+H)+;
¹H NMR (400 MHz, DMSO-d$_6$) 12.93 (br s, 1H), 7.93 (d, J=8.08 Hz, 2H), 7.43 (d, J=8.34 Hz, 2H), 7.25-7.38 (m, 2H), 6.90-7.02 (m, 1H), 6.82-6.89 (m, 2H), 6.75 (d, J=8.08 Hz, 1H), 4.85 (s, 2H), 3.86-4.03 (m, 2H), 3.66-3.80 (m, 5H), 2.91 (br t, J=7.33 Hz, 2H), 1.29 (t, J=6.95 Hz, 3H).

Example 26. 4-({(7-fluorobenzo[d]thiazol-2-yl)[2-(2-fluoro-4-methoxyphenyl)ethyl]amino}methyl) benzoic acid The titled compound was prepared in accordance with the same procedures as in Example 1, using 2-fluoro-4-methoxyphenylethylamine instead of 4-methoxyphenylethylamine used in Step 3 of Example 1.
¹H NMR (400 MHz, DMSO-d$_6$), 12.94 (s, 1H), 7.93 (d, 2H), 7.47-7.40 (m, 2H), 7.36-7.13 (m, 3H), 6.96 (ddd, 1H), 6.83-6.68 (m, 2H), 4.87 (s, 2H), 3.75-3.67 (m, 5H), 2.95 (t, 2H).

Example 27. 4-({[2-(2,4-dimethoxyphenyl)ethyl](7-fluorobenzo[d]thiazol-2-yl)amino}methyl)benzoic acid The titled compound was prepared in accordance with the same procedures as in Example 1, using 2,4-dimethoxyphenylethylamine instead of 4-methoxyphenylethylamine used in Step 3 of Example 1.
¹H NMR (400 MHz, DMSO-d$_6$), 12.93 (s, 1H), 7.93 (d, 2H), 7.42 (d, 2H), 7.35-7.27 (m, 2H), 7.05 (d, 1H), 7.01-6.89 (m, 1H), 6.53 (d, 1H), 6.44 (dd, 1H), 4.85 (s, 2H), 3.79 (s, 3H), 3.72 (s, 3H), 3.62 (t, 2H), 2.87 (t, 2H).

Example 28. 4-({(7-fluorobenzo[d]thiazol-2-yl)[2-(3-fluoro-4-methoxyphenyl)ethyl]amino}methyl) benzoic acid The titled compound was prepared in accordance with the same procedures as in Example 1, using 3-fluoro-4-methoxyphenylethylamine instead of 4-methoxyphenylethylamine used in Step 3 of Example 1.
¹H NMR (400 MHz, DMSO-d$_6$) 12.94 (s, 1H), 7.93 (d, 2H), 7.44 (d, 2H), 7.38-7.27 (m, 2H), 7.20-7.12 (m, 1H), 7.11-7.00 (m, 2H), 6.96 (ddd, 1H), 4.87 (s, 2H), 3.80 (s, 5H), 2.94 (t, 2H).

Example 29. 4-({[2-(3-chloro-4-methoxyphenyl) ethyl](7-fluorobenzo[d]thiazol-2-yl)amino}methyl) benzoic acid The titled compound was prepared in accordance with the same procedures as in Example 1, using 3-chloro-4-methoxyphenylethylamine instead of 4-methoxyphenylethylamine used in Step 3 of Example 1.
¹H NMR (400 MHz, DMSO-d$_6$) 12.93 (s, 1H), 7.93 (d, 2H), 7.44 (d, 2H), 7.39-7.23 (m, 3H), 7.20 (dd, 1H), 7.06 (d, 1H), 7.01-6.86 (m, 1H), 4.87 (s, 2H), 3.81 (s, 3H), 3.76 (t, 2H), 2.93 (t, 2H).

Example 30. 4-{[[2-(4-sec-butoxyphenyl)ethyl](7-fluorobenzo[d]thiazol-2-yl)amino]methyl}benzoic acid The titled compound was prepared in accordance with the same procedures as in Example 1, using 4-sec-butoxyphenylethylamine instead of 4-methoxyphenylethylamine used in Step 3 of Example 1.
LCMS (m/z) 479.2 (M+H)+;
¹H NMR (400 MHz, CDCl$_3$) 8.04 (m, 2H), 7.22-7.41 (m, 5H), 7.08 (m, 2H), 6.77-6.87 (m, 2H), 4.75 (s, 2H), 4.18-4.35 (m, 1H), 3.67 (m, 2H), 2.94 (m, 2H), 1.54-1.78 (m, 2H), 1.21-1.31 (m, 3H), 0.83-1.04 (m, 3H).

Example 31. 4-{[[2-(4-ethylaminophenyl)ethyl](7-fluorobenzo[d]thiazol-2-yl)amino]methyl}benzoic acid The titled compound was prepared in accordance with the same procedures as in Example 1, using 4-ethylaminophenylethylamine instead of 4-methoxyphenylethylamine used in Step 3 of Example 1.
LCMS (m/z) 450.2 (M+H)+;
¹H NMR (400 MHz, CD$_3$OD), 7.96-8.07 (m, 2H), 7.35-7.55 (m, 3H), 7.22-7.35 (m, 3H), 7.05 (m, 1H), 6.73-6.89 (m, 1H), 4.79-4.84 (m, 2H), 3.78 (m, 2H), 3.13-3.28 (m, 2H), 3.02 (m, 2H), 1.15-1.40 (m, 3H).

Example 32. 4-({[2-(4-ethylphenyl)ethyl](7-fluorobenzo[d]thiazol-2-yl)amino}methyl)benzoic acid The titled compound was prepared in accordance with the same procedures as in Example 1, using 4-ethylphenylethylamine instead of 4-methoxyphenylethylamine used in Step 3 of Example 1.

¹H NMR (400 MHz, CDCl₃) 8.04 (br d, J=8.08 Hz, 2H), 7.31-7.42 (m, 3H), 7.02-7.25 (m, 4H), 6.83 (br t, J=8.46 Hz, 1H), 4.75 (s, 2H), 3.69 (br t, J=7.33 Hz, 2H), 2.98 (br t, J=7.45 Hz, 2H), 2.63 (q, J=7.33 Hz, 2H), 1.22 (t, J=7.58 Hz, 3H).

Example 33. 4-{[(7-fluorobenzo[d]thiazol-2-yl){2-[4-(propan-2-yl)phenyl]ethyl}amino]methyl}benzoic acid The titled compound was prepared in accordance with the same procedures as in Example 1, using 4-isopropylphenylethylamine instead of 4-methoxyphenylethylamine used in Step 3 of Example 1.
¹H NMR (400 MHz, DMSO-d₆) 7.03 (br d, J=8.08 Hz, 2H), 6.32-6.47 (m, 4H), 6.19-6.29 (m, 4H), 5.94 (br t, J=8.97 Hz, 1H), 3.84 (s, 2H), 2.82 (br t, J=7.20 Hz, 2H), 2.01-2.12 (m, 2H), 1.95 (td, J=7.07, 14.15 Hz, 1H), 0.30 (brd, J=6.82 Hz, 6H).

Example 34. 4-({[2-(2,3-difluorophenyl)ethyl](7-fluorobenzo[d]thiazol-2-yl)amino}methyl)benzoic acid The titled compound was prepared in accordance with the same procedures as in Example 1, using 2,3-difluorophenylethylamine instead of 4-methoxyphenylethylamine used in Step 3 of Example 1.
¹H NMR (400 MHz, CDCl₃) 8.06 (d, J=8.08 Hz, 2H), 7.38 (br d, J=8.08 Hz, 3H), 7.27-7.33 (m, 1H), 6.91-7.14 (m, 3H), 6.83 (t, J=8.97 Hz, 1H), 4.79 (s, 2H), 3.75 (br t, J=7.45 Hz, 2H), 3.09 (br t, J=7.58 Hz, 2H).

Example 35. 4-({[2-(2,5-difluorophenyl)ethyl](7-fluorobenzo[d]thiazol-2-yl)amino}methyl)benzoic acid The titled compound was prepared in accordance with the same procedures as in Example 1, using 2,5-difluorophenylethylamine instead of 4-methoxyphenylethylamine used in Step 3 of Example 1.
¹H NMR (400 MHz, CDCl₃) 8.06 (d, J=8.08 Hz, 2H), 7.38 (d, J=8.08 Hz, 3H), 7.27-7.33 (m, 1H), 6.74-7.06 (m, 4H), 4.79 (s, 2H), 3.74 (br t, J=7.20 Hz, 2H), 3.03 (br t, J=7.45 Hz, 2H).

Example 36. 4-({(7-fluorobenzo[d]thiazol-2-yl)[2-(3,4,5-trifluorophenyl)ethyl]amino}methyl)benzoic acid The titled compound was prepared in accordance with the same procedures as in Example 1, using 3,4,5-trifluorophenylethylamine instead of 4-methoxyphenylethylamine used in Step 3 of Example 1.
¹H NMR (400 MHz, CDCl₃) 8.08 (d, J=8.08 Hz, 2H), 7.34-7.44 (m, 3H), 7.26-7.34 (m, 1H), 6.78-6.92 (m, 3H), 4.74 (s, 2H), 3.74 (br t, J=7.45 Hz, 2H), 2.88-3.05 (m, 2H).

Example 37. 4-({[2-(3-bromo-4-methoxyphenyl)ethyl](7-fluorobenzo[d]thiazol-2-yl)amino}methyl)benzoic acid The titled compound was prepared in accordance with the same procedures as in Example 1, using 3-bromo-4-methoxyphenylethylamine instead of 4-methoxyphenylethylamine used in Step 3 of Example 1.
¹H NMR (400 MHz, CDCl₃) 8.06 (d, J=8.08 Hz, 2H), 7.31-7.47 (m, 3H), 7.23-7.29 (m, 2H), 7.13-7.23 (m, 1H), 6.79-6.90 (m, 3H), 4.87 (s, 2H), 3.70 (br t, J=7.33 Hz, 2H), 3.09 (br t, J=7.45 Hz, 2H).

Example 38. 4-({[2-(2,4-dichlorophenyl)ethyl](7-fluorobenzo[d]thiazol-2-yl)amino}methyl)benzoic acid The titled compound was prepared in accordance with the same procedures as in Example 1, using 2,4-dichlorophenylethylamine instead of 4-methoxyphenylethylamine used in Step 3 of Example 1.
¹H NMR (400 MHz, CDCl₃), 8.06 (d, J=7.83 Hz, 2H), 7.34-7.42 (m, 4H), 7.23-7.31 (m, 1H), 7.12-7.22 (m, 2H), 6.84 (t, J=8.72 Hz, 1H), 4.75 (s, 2H), 3.73 (br t, J=7.33 Hz, 2H), 3.13 (br t, J=7.33 Hz, 2H).

Example 39. 4-({[2-(2,4-difluorophenyl)ethyl](7-fluorobenzo[d]thiazol-2-yl)amino}methyl)benzoic acid The titled compound was prepared in accordance with the same procedures as in Example 1, using 2,4-difluorophenylethylamine instead of 4-methoxyphenylethylamine used in Step 3 of Example 1.
¹H NMR (400 MHz, CDCl₃) 8.06 (d, J=8.08 Hz, 2H), 7.38 (br d, J=8.34 Hz, 3H), 7.22-7.32 (m, 1H), 7.10-7.21 (m, 1H), 6.81 (quin, J=8.15 Hz, 3H), 4.78 (s, 2H), 3.71 (br t, J=7.45 Hz, 2H), 2.94-3.09 (m, 2H).

Example 40. 4-({(7-fluorobenzo[d]thiazol-2-yl)[2-(2-methoxyphenyl)ethyl]amino}methyl)benzoic acid The titled compound was prepared in accordance with the same procedures as in Example 1, using 2-methoxyphenylethylamine instead of 4-methoxyphenylethylamine used in Step 3 of Example 1.
LCMS (m/z) 437.1 (M+H)+.

Example 41. 4-({(7-fluorobenzo[d]thiazol-2-yl)[2-(2-fluorophenyl)ethyl]amino}methyl)benzoic acid The titled compound was prepared in accordance with the same procedures as in Example 1, using 2-fluorophenylethylamine instead of 4-methoxyphenylethylamine used in Step 3 of Example 1.
LCMS (m/z) 425.1 (M+H)+.

Example 42. 4-({(7-fluorobenzo[d]thiazol-2-yl)[2-(3-methoxyphenyl)ethyl]amino}methyl)benzoic acid The titled compound was prepared in accordance with the same procedures as in Example 1, using 3-methoxyphenylethylamine instead of 4-methoxyphenylethylamine used in Step 3 of Example 1.
LCMS (m/z) 437.2 (M+H)+

Example 43. 4-({[2-(2,3-difluoro-4-methoxyphenyl)ethyl](7-fluorobenzo[d]thiazol-2-yl)amino}methyl)benzoic acid The titled compound was prepared in accordance with the same procedures as in Example 1, using 2,3-difluoro-4-methoxyphenylethylamine instead of 4-methoxyphenylethylamine used in Step 3 of Example 1.
LCMS (m/z) 473.1 (M+H)+;

¹H NMR (400 MHz, CDCl₃) 8.05 (br d, J=8.08 Hz, 3H), 7.32-7.48 (m, 3H), 7.26 (br d, J=5.05 Hz, 2H), 6.84 (br d, J=8.08 Hz, 2H), 6.65 (s, 2H), 4.78 (s, 2H), 3.86 (s, 3H), 3.72 (br t, J=7.20 Hz, 2H), 3.02 (br t, J=7.33 Hz, 2H).

Example 44. 4-{[(7-fluorobenzo[d]thiazol-2-yl){2-[4-methoxy-2-methyl-5-(propan-2-yl)phenyl]ethyl}amino]methyl}benzoic acid The titled compound was prepared in accordance with the same procedures as in Example 1, using 4-methoxy-2-methyl-5-isopropylphenylethylamine instead of 4-methoxyphenylethylamine used in Step 3 of Example 1.
LCMS (m/z) 493.2 (M+H)+;
¹H NMR (400 MHz, CDCl₃) 8.05 (br d, J=8.08 Hz, 2H), 7.29-7.44 (m, 4H), 7.25 (s, 1H), 6.90 (s, 1H), 6.82 (s, 1H), 6.63 (s, 1H), 4.73 (s, 2H), 3.79 (s, 3H), 3.62 (br s, 2H), 3.19-3.45 (m, 1H), 2.96 (br d, J=7.58 Hz, 2H), 2.28 (s, 3H), 1.16 (d, J=6.82 Hz, 6H).

Example 45. 4-({[2-(2,5-difluoro-4-methoxyphenyl)ethyl](7-fluorobenzo[d]thiazol-2-yl)amino}methyl)benzoic acid The titled compound was prepared in accordance with the same procedures as in Example 1, using 2,5-difluoro-4-methoxyphenylethylamine instead of 4-methoxyphenylethylamine used in Step 3 of Example 1.
LCMS (m/z) 473.1 (M+H)+;
¹H NMR (400 MHz, CDCl₃) 8.05 (br d, J=8.08 Hz, 2H), 7.38 (br d, J=8.08 Hz, 3H), 7.19-7.33 (m, 3H), 6.75-7.02 (m, 2H), 6.58-6.75 (m, 2H), 4.79 (s, 2H), 3.84 (s, 3H), 3.70 (br t, J=7.33 Hz, 2H), 2.96 (br t, J=7.45 Hz, 2H).

Example 46. 4-({[2-(2-chloro-4-methoxyphenyl)ethyl](7-fluorobenzo[d]thiazol-2-yl)amino}methyl)benzoic acid The titled compound was prepared in accordance with the same procedures as in Example 1, using 2-chloro-4-methoxyphenylethylamine instead of 4-methoxyphenylethylamine used in Step 3 of Example 1.
LCMS (m/z) 471.1 (M+H)+;
¹H NMR (400 MHz, CDCl₃) 8.05 (br d, J=8.08 Hz, 2H), 7.38 (br d, J=8.08 Hz, 3H), 7.26 (s, 3H), 7.12 (d, J=8.34 Hz, 1H), 6.91 (d, J=2.27 Hz, 1H), 6.79-6.87 (m, 1H), 6.75 (br d, J=8.59 Hz, 1H), 4.76 (s, 2H), 3.78 (s, 3H), 3.69 (br t, J=7.33 Hz, 3H), 3.09 (br t, J=7.33 Hz, 2H).

Example 47. 4-({(7-fluorobenzo[d]thiazol-2-yl)[2-(4-methoxy-2,3-dimethylphenyl)ethyl]amino}methyl)benzoic acid The titled compound was prepared in accordance with the same procedures as in Example 1, using 4-methoxy-2,3-dimethylphenylethylamine instead of 4-methoxyphenylethylamine used in Step 3 of Example 1.
LCMS (m/z) 465.2 (M+H)+;
¹H NMR (400 MHz, CD₃OD), 7.94-8.05 (m, 2H), 7.26-7.43 (m, 4H), 6.95 (d, J=8.34 Hz, 1H), 6.87 (ddd, J=1.52, 7.58, 9.35 Hz, 1H), 6.71 (d, J=8.59 Hz, 1H), 4.70-4.78 (m, 2H), 3.77 (s, 3H), 3.59-3.69 (m, 2H), 3.01 (br t, J=7.45 Hz, 2H), 2.21 (s, 3H), 2.14 (s, 3H).

Example 48. 4-({(7-fluorobenzo[d]thiazol-2-yl)[2-(4-methoxy-2,5-dimethylphenyl)ethyl]amino}methyl)benzoic acid The titled compound was prepared in accordance with the same procedures as in Example 1, using 4-methoxy-2,5-dimethylphenylethylamine instead of 4-methoxyphenylethylamine used in Step 3 of Example 1.
LCMS (m/z) 465.2 (M+H)+;
¹H NMR (400 MHz, CD₃OD), 8.01 (d, J=8.34 Hz, 1H), 7.96-8.05 (m, 1H), 7.39 (br d, J=8.34 Hz, 2H), 7.26-7.36 (m, 2H), 6.82-6.92 (m, 2H), 6.68 (s, 1H), 4.72-4.80 (m, 2H), 3.78 (s, 3H), 3.66 (b r t, J=7.45 Hz, 2H), 2.94 (br t, J=7.58 Hz, 2H), 2.27 (s, 3H), 2.10 (s, 3H).

Example 49. 4-({(7-fluorobenzo[d]thiazol-2-yl)[2-(4-methoxy-3-methylphenyl)ethyl]amino}methyl)benzoic acid The titled compound was prepared in accordance with the same procedures as in Example 1, using 4-methoxy-3-methylphenylethylamine instead of 4-methoxyphenylethylamine used in Step 3 of Example 1.
LCMS (m/z) 451.1 (M+H)+;
¹H NMR (400 MHz, CD₃OD), 8.01 (d, J=8.34 Hz, 2H), 7.39 (d, J=8.08 Hz, 2H), 7.26-7.36 (m, 2H), 6.95-7.05 (m, 2H), 6.77-6.91 (m, 2H), 4.74-4.81 (m, 2H), 3.79 (s, 3H), 3.74 (br t, J=7.45 Hz, 2H), 2.94 (t, J=7.45 Hz, 2H), 2.16 (s, 3H).

Example 50. 4-({(7-fluorobenzo[d]thiazol-2-yl)[2-(4-methoxy-2-methylphenyl)ethyl]amino}methyl)benzoic acid The titled compound was prepared in accordance with the same procedures as in Example 1, using 4-methoxy-2-methylphenylethylamine instead of 4-methoxyphenylethylamine used in Step 3 of Example 1.
LCMS (m/z) 451.2 (M+H)+;
¹H NMR (400 MHz, CD₃OD), 8.01 (d, J=7.82 Hz, 2H), 7.40 (d, J=8.59 Hz, 2H), 7.28-7.37 (m, 2H), 7.06 (d, J=8.34 Hz, 1H), 6.87 (ddd, J=1.52, 7.52, 9.41 Hz, 1H), 6.73 (s, 1H), 6.70 (d, J=8.05 Hz, 1H), 4.74-4.82 (m, 2H), 3.75 (s, 3H), 3.64-3.72 (m, 2H), 2.93-3.03 (m, 2H), 2.29 (s, 3H).

Example 51. 4-({[2-(2,6-difluoro-4-methoxyphenyl)ethyl](7-fluorobenzo[d]thiazol-2-yl)amino}methyl)benzoic acid The titled compound was prepared in accordance with the same procedures as in Example 1, using 2,6-difluoro-4-methoxyphenylethylamine instead of 4-methoxyphenylethylamine used in Step 3 of Example 1.
LCMS (m/z) 473.1 (M+H)+;
¹H NMR (400 MHz, CD₃OD), 7.92-8.07 (m, 2H), 7.41 (d, J=8.34 Hz, 2H), 7.22-7.35 (m, 2H), 6.80-6.89 (m, 1H), 6.45-6.58 (m, 2H), 4.83-4.86 (m, 2H), 3.68-3.78 (m, 5H), 3.04 (br t, J=6.82 Hz, 2H).

Example 52. 4-(1-{(7-fluorobenzo[d]thiazol-2-yl)[2-(4-methoxyphenyl)ethyl]amino}ethyl)benzoic acid The titled compound was prepared in accordance with the same procedures as in Example 1, using methyl 4-(1-bromoethyl)benzoate instead of methyl 4-(bromomethyl)benzoate used in Step 4 of Example 1.
LCMS (m/z) 451.0 (M+H)+;
¹H NMR (400 MHz, CDCl₃) 8.09 (d, J=8.34 Hz, 2H), 7.49 (d, J=8.34 Hz, 2H), 7.40 (dd, J=0.76, 8.08 Hz, 1H), 7.26-7.34 (m, 1H), 6.93-7.06 (m, 2H), 6.73-6.89 (m, 3H), 5.82 (br d, J=6.82 Hz, 1H), 3.77 (s, 3H), 3.31-3.52 (m, 2H), 2.84-2.96 (m, 1H), 2.59-2.73 (m, 1H), 1.70 (d, J=7.07 Hz, 3H)

Example 53. 4-(1-{(7-fluorobenzo[d]thiazol-2-yl)[2-(4-methoxyphenyl)ethyl]amino}propyl)benzoic acid The titled compound was prepared in accordance with the same procedures as in Example 1, using methyl 4-(1-bromopropyl)benzoate instead of methyl 4-(bromomethyl)benzoate used in Step 4 of Example 1.

$^1$H NMR (400 MHz, DMSO-d$_6$) 12.99 (s, 1H), 7.97 (d, 2H), 7.62 (d, 2H), 7.44-7.29 (m, 2H), 7.06 (d, 2H), 6.99 (t, 1H), 6.91-6.78 (m, 2H), 5.38 (s, 1H), 3.71 (s, 3H), 3.53-3.41 (m, 1H), 3.37-3.32 (m, 1H), 2.86-2.73 (m, 1H), 2.36 (td, 1H), 2.27-2.15 (m, 2H), 0.96 (t, 3H).

Example 54. 4-(1-{(7-fluorobenzo[d]thiazol-2-yl)[2-(3-fluoro-4-methoxyphenyl)ethyl]amino}ethyl)benzoic acid The titled compound was prepared in accordance with the same procedures as in Example 28, using methyl 4-(1-bromoethyl)benzoate instead of methyl 4-(bromomethyl)benzoate used in Step 4 of Example 28.

LCMS (m/z) 469.0 (M+H)+;

$^1$H NMR (400 MHz, CDCl$_3$) 8.04-8.15 (m, J=8.34 Hz, 2H), 7.45-7.54 (m, J=8.34 Hz, 2H), 7.41 (dd, J=0.88, 7.96 Hz, 1H), 7.26-7.31 (m, 1H), 6.72-6.90 (m, 4H), 5.68-5.81 (m, 1H), 3.85 (s, 3H), 3.32-3.56 (m, 2H), 2.82-3.02 (m, 1H), 2.53-2.74 (m, 1H), 1.70 (d, J=7.07 Hz, 3H)

Example 55. 4-(1-{[2-(3-bromo-4-methoxyphenyl)ethyl](7-fluorobenzo[d]thiazol-2-yl)amino}ethyl)benzoic acid The titled compound was prepared in accordance with the same procedures as in Example 37, using methyl 4-(1-bromoethyl)benzoate instead of methyl 4-(bromomethyl)benzoate used in Step 4 of Example 37.

LCMS (m/z) 530.0 (M+H)+;

$^1$H NMR (400 MHz, CDCl$_3$) 8.06 (d, J=8.34 Hz, 2H), 7.49 (d, J=8.08 Hz, 2H), 7.41 (d, J=8.08 Hz, 1H), 7.26-7.32 (m, 1H), 7.09-7.21 (m, 1H), 6.75-6.90 (m, 3H), 5.87 (br d, J=6.82 Hz, 1H), 3.45-3.60 (m, 1H), 3.29-3.45 (m, 1H), 2.90-3.10 (m, 2H), 1.74 (d, J=7.07 Hz, 3H)

Example 56. 4-(1-{[2-(2,4-difluorophenyl)ethyl](7-fluorobenzo[d]thiazol-2-yl)amino}ethyl)benzoic acid The titled compound was prepared in accordance with the same procedures as in Example 39, using methyl 4-(1-bromoethyl)benzoate instead of methyl 4-(bromomethyl)benzoate used in Step 4 of Example 39.

LCMS (m/z) 457.0 (M+H)+;

$^1$H NMR (400 MHz, CDCl$_3$) 8.03-8.15 (m, J=8.34 Hz, 2H), 7.45-7.53 (m, J=8.34 Hz, 2H), 7.41 (dd, J=0.76, 8.08 Hz, 1H), 7.27-7.32 (m, 1H), 7.09 (dt, J=6.32, 8.46 Hz, 1H), 6.69-6.89 (m, 3H), 5.74 (br d, J=6.57 Hz, 1H), 3.45-3.59 (m, 1H), 3.30-3.45 (m, 1H), 2.91-3.05 (m, 1H), 2.70-2.83 (m, 1H), 1.72 (d, J=7.07 Hz, 3H)

Example 57. 4-(1-{[2-(2,3-difluorophenyl)ethyl](7-fluorobenzo[d]thiazol-2-yl)amino}ethyl)benzoic acid The titled compound was prepared in accordance with the same procedures as in Example 34, using methyl 4-(1-bromoethyl)benzoate instead of methyl 4-(bromomethyl)benzoate used in Step 4 of Example 34.

LCMS (m/z) 457 (M+H)+;

$^1$H NMR (400 MHz, CDCl$_3$) 8.08 (d, J=8.34 Hz, 2H), 7.38-7.53 (m, 3H), 7.27-7.31 (m, 1H), 6.81-7.05 (m, 4H), 5.72 (br d, J=6.82 Hz, 1H), 3.50-3.62 (m, 1H), 3.36-3.50 (m, 1H), 2.95-3.10 (m, 1H), 2.77-2.95 (m, 1H), 1.73 (d, J=7.07 Hz, 3H)

Example 58. 4-(1-{(7-fluorobenzo[d]thiazol-2-yl)[2-(3,4,5-trifluorophenyl)ethyl]amino}ethyl)benzoic acid The titled compound was prepared in accordance with the same procedures as in Example 36, using methyl 4-(1-bromoethyl)benzoate instead of methyl 4-(bromomethyl)benzoate used in Step 4 of Example 36.

LCMS (m/z) 475 (M+H)+;

$^1$H NMR (400 MHz, CDCl$_3$) 8.06-8.15 (m, 2H), 7.39-7.54 (m, 3H), 7.28-7.33 (m, 1H), 6.65-6.91 (m, 2H), 5.51-5.63 (m, 1H), 3.33-3.58 (m, 2H), 2.81-2.99 (m, 1H), 2.55-2.76 (m, 1H), 1.63-1.78 (m, 3H)

Example 59. 4-(1-{[2-(2,4-dichlorophenyl)ethyl](7-fluorobenzo[d]thiazol-2-yl)amino}ethyl)benzoic acid The titled compound was prepared in accordance with the same procedures as in Example 38, using methyl 4-(1-bromoethyl)benzoate instead of methyl 4-(bromomethyl)benzoate used in Step 4 of Example 38.

LCMS (m/z) 490 (M+H)+;

$^1$H NMR (400 MHz, CDCl$_3$) 8.07 (d, J=8.34 Hz, 2H), 7.37-7.53 (m, 3H), 7.26-7.34 (m, 2H), 7.05-7.22 (m, 2H), 6.85 (t, J=8.72 Hz, 1H), 5.70 (br d, J=6.57 Hz, 1H), 3.37-3.56 (m, 2H), 3.10 (ddd, J=5.81, 10.42, 13.07 Hz, 1H), 2.92 (ddd, J=5.81, 10.23, 13.01 Hz, 1H), 1.71 (d, J=7.07 Hz, 3H)

Example 60. 4-(1-{[2-(2,3-difluoro-4-methoxyphenyl)ethyl](7-fluorobenzo[d]thiazol-2-yl)amino}ethyl)benzoic acid The titled compound was prepared in accordance with the same procedures as in Example 43, using methyl 4-(1-bromoethyl)benzoate instead of methyl 4-(bromomethyl)benzoate used in Step 4 of Example 43.

LCMS (m/z) 487.1 (M+H)+;

$^1$H NMR (400 MHz, CDCl$_3$) 8.07 (m, 2H), 7.35-7.57 (m, 3H), 7.20-7.35 (m, 2H), 6.71-6.98 (m, 3H), 6.56-6.71 (m, 1H), 5.73 (m, 1H), 3.86 (s, 3H), 3.35-3.61 (m, 2H), 2.80-3.14 (m, 2H), 1.72 (m, 2H)

Example 61. 4-(1-{[2-(2,5-difluoro-4-methoxyphenyl)ethyl](7-fluorobenzo[d]thiazol-2-yl)amino}ethyl)benzoic acid The titled compound was prepared in accordance with the same procedures as in Example 45, using methyl 4-(1-bromoethyl)benzoate instead of methyl 4-(bromomethyl)benzoate used in Step 4 of Example 45.

LCMS (m/z) 487.1 (M+H)+;

$^1$H NMR (400 MHz, CDCl$_3$) 8.07 (m, 2H), 7.35-7.57 (m, 3H), 7.19-7.35 (m, 2H), 6.78-6.93 (m, 2H), 6.62 (m, 1H), 5.72 (m, 1H), 3.83 (s, 3H), 3.49 (m, 1H), 3.18-3.43 (m, 1H), 2.83-3.06 (m, 1H), 2.75 (m, 1H), 1.72 (d, J=7.07 Hz, 3H)

Example 62. 4-{1-[(7-fluorobenzo[d]thiazol-2-yl){2-[4-methoxy-2-methyl-5-(propan-2-yl)phenyl]ethyl}amino]ethyl}benzoic acid The titled compound was prepared in accordance with the same procedures as in Example 44, using methyl 4-(1-bromoethyl)benzoate instead of methyl 4-(bromomethyl)benzoate used in Step 4 of Example 44.

LCMS (m/z) 507.2 (M+H)+;

$^1$H NMR (400 MHz, CDCl$_3$) 8.10 (d, J=8.08 Hz, 2H), 7.52 (m, 2H), 7.41 (m, 1H), 7.07-7.35 (m, 2H), 6.84 (m, 1H), 6.75 (s, 1H), 6.58 (s, 1H), 5.79 (m, 1H), 3.77 (s, 3H), 3.27-3.53 (m, 2H), 3.10-3.27 (m, 1H), 2.94 (m, 1H), 2.60 (m, 1H), 2.21 (s, 3H), 1.71 (d, J=6.82 Hz, 3H), 1.17 (t, J=7.07 Hz, 6H)

Example 63. 4-(1-{(7-fluorobenzo[d]thiazol-2-yl)[2-(4-methoxy-2,3-dimethylphenyl)ethyl]amino}ethyl)benzoic acid The titled compound was prepared in accordance with the same procedures as in Example 47, using methyl 4-(1-bromoethyl)benzoate instead of methyl 4-(bromomethyl)benzoate used in Step 4 of Example 47.

LCMS (m/z) 479.2 (M+H)+;

$^1$H NMR (400 MHz, CD$_3$OD), 8.03 (d, J=8.34 Hz, 2H), 7.51 (d, J=8.08 Hz, 2H), 7.35-7.41 (m, 1H), 7.27-7.35 (m, 1H), 6.87 (t, J=8.72 Hz, 1H), 6.78 (d, J=8.34 Hz, 1H), 6.65 (d, J=8.34 Hz, 1H), 5.64 (br d, J=6.57 Hz, 1H), 3.75 (s, 3H), 3.35-3.48 (m, 2H), 2.94 (ddd, J=5.81, 10.61, 13.39 Hz, 1H), 2.61 (ddd, J=5.81, 10.48, 13.26 Hz, 1H), 2.07 (d, J=6.32 Hz, 6H), 1.68 (d, J=7.07 Hz, 3H)

Example 64. 4-(1-{(7-fluorobenzo[d]thiazol-2-yl)[2-(4-methoxy-2,5-dimethylphenyl)ethyl]amino}ethyl)benzoic acid The titled compound was prepared in accordance with the same procedures as in Example 48, using methyl 4-(1-bromoethyl)benzoate instead of methyl 4-(bromomethyl)benzoate used in Step 4 of Example 48.

LCMS (m/z) 479.2 (M+H)+;

$^1$H NMR (400 MHz, CD$_3$OD), 8.05 (d, J=8.34 Hz, 2H), 7.55 (d, J=8.08 Hz, 2H), 7.28-7.42 (m, 2H), 6.83-6.94 (m, 1H), 6.68 (s, 1H), 6.61 (s, 1H), 5.67 (br d, J=7.07 Hz, 1H), 3.76 (s, 3H), 3.35-3.52 (m, 2H), 2.84-2.97 (m, 1H), 2.47-2.60 (m, 1H), 2.16 (s, 3H), 2.09 (s, 3H), 1.70 (d, J=7.07 Hz, 3H)

Example 65. 4-(1-{(7-fluorobenzo[d]thiazol-2-yl)[2-(4-methoxy-3-methylphenyl)ethyl]amino}ethyl)benzoic acid The titled compound was prepared in accordance with the same procedures as in Example 49, using methyl 4-(1-bromoethyl)benzoate instead of methyl 4-(bromomethyl)benzoate used in Step 4 of Example 49.

LCMS (m/z) 465.2 (M+H)+;

$^1$H NMR (400 MHz, CD$_3$OD), 8.06 (d, J=7.83 Hz, 2H), 7.55 (br d, J=7.58 Hz, 2H), 7.27-7.43 (m, 2H), 6.73-6.84 (m, 2H), 5.67 (br d, J=6.82 Hz, 1H), 3.79 (s, 3H), 3.41-3.59 (m, 2H), 2.89 (br s, 1H), 2.54 (br s, 1H), 2.14 (s, 3H), 1.72 (d, J=7.07 Hz, 3H)

Example 66. 4-(1-{(7-fluorobenzo[d]thiazol-2-yl)[2-(4-methoxy-2-methylphenyl)ethyl]amino}ethyl)benzoic acid The titled compound was prepared in accordance with the same procedures as in Example 50, using methyl 4-(1-bromoethyl)benzoate instead of methyl 4-(bromomethyl)benzoate used in Step 4 of Example 50.

LCMS (m/z) 465.2 (M+H)+;

$^1$H NMR (400 MHz, CD$_3$OD), 8.06 (d, J=8.34 Hz, 2H), 7.56 (d, J=8.08 Hz, 2H), 7.28-7.41 (m, 2H), 6.84-6.95 (m, 2H), 6.62-6.70 (m, 2H), 5.66 (br d, J=6.82 Hz, 1H), 3.74 (s, 3H), 3.35-3.56 (m, 2H), 2.88-3.02 (m, 1H), 2.53-2.66 (m, 1H), 2.17 (s, 3H), 1.71 (d, J=7.07 Hz, 3H)

Example 67. 4-(1-{[2-(2,6-difluoro-4-methoxyphenyl)ethyl](7-fluorobenzo[d]thiazol-2-yl)amino}ethyl)benzoic acid The titled compound was prepared in accordance with the same procedures as in Example 51, using methyl 4-(1-bromoethyl)benzoate instead of methyl 4-(bromomethyl)benzoate used in Step 4 of Example 51.

LCMS (m/z) 487.1 (M+H)+;

$^1$H NMR (400 MHz, CD$_3$OD), 8.01 (d, J=8.34 Hz, 2H), 7.50 (d, J=8.08 Hz, 2H), 7.27-7.42 (m, 2H), 6.89 (t, J=8.84 Hz, 1H), 6.49 (d, J=9.60 Hz, 2H), 5.71 (br d, J=7.07 Hz, 1H), 3.77 (s, 3H), 3.51-3.63 (m, 1H), 3.48 (br dd, J=6.06, 8.84 Hz, 1H), 2.80-3.00 (m, 2H), 1.71 (d, J=6.82 Hz, 3H)

Example 68. 4-(1-{[2-(2,3-difluoro-4-methoxyphenyl)ethyl](7-fluorobenzo[d]thiazol-2-yl)amino}propyl)benzoic acid The titled compound was prepared in accordance with the same procedures as in Example 43, using methyl 4-(1-bromopropyl)benzoate instead of methyl 4-(bromomethyl)benzoate used in Step 4 of Example 43.

LCMS (m/z) 501.2 (M+H)+;

$^1$H NMR (400 MHz, CDCl$_3$) 7.99-8.14 (m, 2H), 7.53 (br d, J=7.83 Hz, 2H), 7.35-7.47 (m, 1H), 7.22-7.34 (m, 1H), 6.71-6.96 (m, 3H), 6.56-6.69 (m, 1H), 5.45 (br s, 1H), 3.77-3.93 (m, 3H), 3.36-3.55 (m, 2H), 2.80-3.04 (m, 1H), 2.53-2.70 (m, 1H), 2.09-2.26 (m, 2H), 1.06 (br t, J=6.95 Hz, 3H)

Example 69. 4-(1-{[2-(2,5-difluoro-4-methoxyphenyl)ethyl](7-fluorobenzo[d]thiazol-2-yl)amino}propyl)benzoic acid The titled compound was prepared in accordance with the same procedures as in Example 45, using methyl 4-(1-bromopropyl)benzoate instead of methyl 4-(bromomethyl)benzoate used in Step 4 of Example 45.

LCMS (m/z) 501.2 (M+H)+;

$^1$H NMR (400 MHz, CDCl$_3$) 8.08 (br d, J=8.08 Hz, 2H), 7.53 (br d, J=8.08 Hz, 2H), 7.41 (br d, J=8.08 Hz, 1H), 7.20-7.34 (m, 1H), 6.78-7.00 (m, 2H), 6.53-6.71 (m, 1H), 5.44 (br s, 1H), 3.75-3.91 (m, 3H), 3.42 (br t, J=7.96 Hz, 2H), 2.85 (br d, J=13.14 Hz, 1H), 2.58 (br s, 1H), 2.12-2.39 (m, 2H), 1.07 (br t, J=7.07 Hz, 3H)

Example 70. 4-(1-{[2-(2-chloro-4-methoxyphenyl)ethyl](7-fluorobenzo[d]thiazol-2-yl)amino}propyl)benzoic acid The titled compound was prepared in accordance with the same procedures as in Example 46, using methyl 4-(1- bromopropyl)benzoate instead of methyl 4-(bromomethyl) benzoate used in Step 4 of Example 46.

LCMS (m/z) 499.1 (M+H)+;
$^1$H NMR (400 MHz, CDCl$_3$) 7.97-8.16 (m, 2H), 7.54 (br d, J=8.08 Hz, 2H), 7.35-7.49 (m, 1H), 7.16-7.33 (m, 1H), 7.06 (br d, J=8.34 Hz, 1H), 6.77-6.94 (m, 2H), 6.71 (br d, J=8.34 Hz, 2H), 5.53 (br s, 1H), 3.70-3.82 (m, 3H), 3.33-3.58 (m, 2H), 2.88-3.14 (m, 1H), 2.66-2.86 (m, 1H), 2.16-2.29 (m, 1H), 1.07 (br t, J=7.07 Hz, 3H)

Example 71. 4-(1-{(7-fluorobenzo[d]thiazol-2-yl)[2-(4-methoxy-2,3-dimethylphenyl)ethyl]amino}propyl)benzoic acid The titled compound was prepared in accordance with the same procedures as in Example 47, using methyl 4-(1-bromopropyl)benzoate instead of methyl 4-(bromomethyl) benzoate used in Step 4 of Example 47.

LCMS (m/z) 493.2 (M+H)+;
$^1$H NMR (400 MHz, CD$_3$OD), 8.02 (d, J=8.34 Hz, 2H), 7.55 (br d, J=8.34 Hz, 2H), 7.25-7.38 (m, 2H), 6.86 (t, J=8.89 Hz, 1H), 6.73 (d, J=8.34 Hz, 1H), 6.62 (d, J=7.60 Hz, 1H), 5.40 (br s, 1H), 3.73 (s, 3H), 3.25-3.31 (m, 2H), 2.86 (ddd, J=6.32, 10.23, 13.01 Hz, 1H), 2.39 (ddd, J=6.19, 10.29, 13.33 Hz, 1H), 2.11-2.26 (m, 2H), 2.06 (s, 6H), 1.02 (t, J=7.33 Hz, 3H)

Example 72. 4-(1-{(7-fluorobenzo[d]thiazol-2-yl)[2-(4-methoxy-2,5-dimethylphenyl)ethyl]amino}propyl)benzoic acid The titled compound was prepared in accordance with the same procedures as in Example 48, using methyl 4-(1-bromopropyl)benzoate instead of methyl 4-(bromomethyl) benzoate used in Step 4 of Example 48.

LCMS (m/z) 493.2 (M+H)+;
$^1$H NMR (400 MHz, CD$_3$OD) 7.96-8.11 (m, J=8.08 Hz, 2H), 7.50-7.63 (m, J=8.08 Hz, 2H), 7.26-7.40 (m, 2H), 6.86 (br t, J=8.72 Hz, 1H), 6.62 (s, 1H), 6.56 (s, 1H), 5.41 (br s, 1H), 3.73 (s, 3H), 3.32-3.45 (m, 2H), 2.71-2.91 (m, 1H), 2.24-2.36 (m, 1H), 2.14-2.24 (m, 2H), 2.12 (s, 3H), 2.06 (s, 3H), 1.02 (brt, J=7.20 Hz, 3H)

Example 73. 4-(1-{(7-fluorobenzo[d]thiazol-2-yl)[2-(4-methoxy-3-methylphenyl)ethyl]amino}propyl) benzoic acid The titled compound was prepared in accordance with the same procedures as in Example 49, using methyl 4-(1-bromopropyl)benzoate instead of methyl 4-(bromomethyl) benzoate used in Step 4 of Example 49.

LCMS (m/z) 479.2 (M+H)+;
$^1$H NMR (400 MHz, METHANOL-d4) 8.04 (d, J=8.34 Hz, 2H), 7.58 (d, J=8.08 Hz, 2H), 7.34-7.42 (m, 1H), 7.31 (dt, J=5.81, 8.08 Hz, 1H), 6.78-6.90 (m, 2H), 6.69-6.78 (m, 2H), 5.43 (br s, 1H), 3.76 (s, 3H), 3.43 (ddd, J=3.41, 6.25, 9.79 Hz, 2H), 2.70-2.87 (m, 1H), 2.13-2.32 (m, 3H), 2.11 (s, 3H), 1.02 (t, J=7.33 Hz, 3H)

Example 74. 4-(1-{(7-fluorobenzo[d]thiazol-2-yl)[2-(4-methoxy-2-methylphenyl)ethyl]amino}propyl) benzoic acid The titled compound was prepared in accordance with the same procedures as in Example 50, using methyl 4-(1-bromopropyl)benzoate instead of methyl 4-(bromomethyl) benzoate used in Step 4 of Example 50.

LCMS (m/z) 479.2 (M+H)+;
$^1$H NMR (400 MHz, CD$_3$OD) 8.05 (s, 1H), 8.03 (s, 1H), 7.59 (d, J=8.08 Hz, 2H), 7.26-7.40 (m, 2H), 6.81-6.93 (m, 2H), 6.56-6.69 (m, 2H), 5.43 (br s, 1H), 3.71 (s, 3H), 3.34-3.44 (m, 2H), 3.25-3.33 (m, 6H), 2.86 (td, J=3.57, 6.76 Hz, 1H), 2.35 (td, J=3.63, 6.63 Hz, 1H), 2.16-2.27 (m, 2H), 2.15 (s, 3H), 1.04 (t, J=7.33 Hz, 3H)

Example 75. 4-(1-{[2-(2,6-difluoro-4-methoxyphenyl)ethyl](7-fluorobenzo[d]thiazol-2-yl)amino}propyl)benzoic acid The titled compound was prepared in accordance with the same procedures as in Example 51, using methyl 4-(1-bromopropyl)benzoate instead of methyl 4-(bromomethyl) benzoate used in Step 4 of Example 51.

LCMS (m/z) 501.2 (M+H)+;
$^1$H NMR (400 MHz, DMSO-d$_6$) 12.97 (br s, 1H), 7.92 (d, J=8.08 Hz, 2H), 7.54 (d, J=8.34 Hz, 2H), 7.30-7.41 (m, 2H), 7.00 (ddd, J=1.77, 7.33, 9.35 Hz, 1H), 6.64 (d, J=9.60 Hz, 2H), 5.36 (br s, 1H), 3.73 (s, 3H), 3.36-3.50 (m, 2H), 2.75-2.87 (m, 1H), 2.52-2.60 (m, 1H), 2.05-2.23 (m, 2H), 0.94 (t, J=7.20 Hz, 3H)

Example 76. 4-{1-[(7-fluorobenzo[d]thiazol-2-yl){2-[4-methoxy-2-methyl-5-(propan-2-yl)phenyl]ethyl}amino]propyl}benzoic acid The titled compound was prepared in accordance with the same procedures as in Example 44, using methyl 4-(1-bromopropyl)benzoate instead of methyl 4-(bromomethyl) benzoate used in Step 4 of Example 44.

LCMS (m/z) 521.2 (M+H)+;
$^1$H NMR (400 MHz, CDCl$_3$) 8.11 (br d, J=8.34 Hz, 1H), 7.57 (br d, J=8.34 Hz, 2H), 7.40 (br d, J=8.08 Hz, 1H), 7.21-7.35 (m, 1H), 6.83 (br t, J=8.59 Hz, 1H), 6.75 (s, 1H), 6.61-6.69 (m, 1H), 6.57 (s, 1H), 5.53 (br s, 1H), 3.74-3.86 (m, 3H), 3.45 (br d, J=7.07 Hz, 1H), 3.27-3.40 (m, 2H), 3.22 (br dd, J=6.44, 13.26 Hz, 1H), 2.85-3.05 (m, 1H), 2.29-2.49 (m, 2H), 2.14-2.29 (m, 4H), 1.12-1.32 (m, 8H), 1.02-1.12 (m, 2H)

Example 77. 4-({(7-fluorobenzo[d]thiazol-2-yl)[2-(4-methoxyphenyl)ethyl]amino}methyl)-2-hydroxybenzoic acid The titled compound was prepared in accordance with the same procedures as in Example 1, using methyl 4-bromomethyl-2-hydroxybenzoate instead of methyl 4-(bromomethyl)benzoate used in Step 4 of Example 1.

$^1$H NMR (400 MHz, DMSO-d$_6$) 11.37 (s, 1H), 7.80-7.72 (m, 1H), 7.37-7.23 (m, 2H), 7.20 (d, 2H), 6.96 (ddd, 1H), 6.94-6.83 (m, 4H), 4.79 (s, 2H), 3.72 (d, 5H), 2.92 (t, 2H).

Example 78. 3-chloro-4-({(7-fluorobenzo[d]thiazol-2-yl)[2-(4-methoxyphenyl)ethyl]amino}methyl)benzoic acid The titled compound was prepared in accordance with the same procedures as in Example 1, using methyl 4-bromomethyl-3-chlorobenzoate instead of methyl 4-(bromomethyl) benzoate used in Step 4 of Example 1.

LCMS (m/z) 471 (M+H)+;
$^1$H NMR (400 MHz, CDCl$_3$) 8.08 (d, J=1.52 Hz, 1H), 7.88 (dd, J=1.52, 8.08 Hz, 1H), 7.38 (d, J=8.08 Hz, 1H), 7.32 (d, J=8.08 Hz, 1H), 7.26-7.30 (m, 1H), 7.14 (d, J=8.59 Hz,

2H), 6.79-6.92 (m, 3H), 4.86 (s, 2H), 3.79 (s, 3H), 3.71 (br t, J=7.45 Hz, 2H), 3.00 (t, J=7.58 Hz, 2H)

Example 79. 4-({[2-(4-methoxyphenyl)ethyl](6-nitro-benzo[d]thiazol-2-yl)amino}methyl)benzoic acid The titled compound was prepared in accordance with the same procedures as in Example 1, using 2-chloro-6-nitrobenzo[d]thiazole instead of 2-chloro-7-fluorobenzo[d]thiazole used in Step 3 of Example 1.

$^1$H NMR (400 MHz, DMSO-d$_6$) 12.93 (s, 1H), 8.81 (d, 1H), 8.21-8.11 (m, 1H), 7.93 (d, 2H), 7.56 (d, 1H), 7.44 (d, 2H), 7.23-7.16 (m, 2H), 6.87 (d, 2H), 4.92 (s, 2H), 3.72 (s, 5H), 2.94 (t, 2H).

Example 80. 4-({[2-(4-methoxyphenyl)ethyl](7-nitro-benzo[d]thiazol-2-yl)amino}methyl)benzoic acid The titled compound was prepared in accordance with the same procedures as in Example 1, using 2-chloro-7-nitrobenzo[d]thiazole instead of 2-chloro-7-fluorobenzo[d]thiazole used in Step 3 of Example 1.

$^1$H NMR (400 MHz, DMSO-d$_6$) 12.94 (s, 1H), 8.14 (d, 1H), 8.01 (d, 1H), 7.93 (d, 2H), 7.51 (d, 2H), 7.25-7.16 (m, 3H), 6.87 (d, 2H), 4.91 (s, 2H), 3.92-3.62 (m, 5H), 2.95 (t, 2H).

Example 81. 4-({(6-amino-benzo[d]thiazol-2-yl)[2-(4-methoxyphenyl)ethyl]amino}methyl)benzoic acid The titled compound was prepared in accordance with the same procedures as in Example 1, using 2-chloro-6-aminobenzo[d]thiazole instead of 2-chloro-7-fluorobenzo[d]thiazole used in Step 3 of Example 1.

$^1$H NMR (400 MHz, DMSO-d$_6$) 7.90 (d, 2H), 7.40 (d, 2H), 7.20-7.12 (m, 3H), 6.92-6.82 (m, 3H), 6.56 (dd, 1H), 4.75 (s, 2H), 3.71 (s, 3H), 3.60 (t, 2H), 2.86 (t, 2H).

Example 82. 4-({(7-amino-benzo[d]thiazol-2-yl)[2-(4-methoxyphenyl)ethyl]amino}methyl)benzoic acid The titled compound was prepared in accordance with the same procedures as in Example 1, using 2-chloro-7-aminobenzo[d]thiazole instead of 2-chloro-7-fluorobenzo[d]thiazole used in Step 3 of Example 1.

$^1$H NMR (400 MHz, DMSO-d$_6$) 7.92 (d, 2H), 7.45 (d, 2H), 7.19 (d, 2H), 6.95-6.75 (m, 4H), 6.55 (d, 1H), 4.82 (s, 2H), 3.72 (s, 3H), 3.66 (t, 2H), 2.90 (t, 2H).

Example 83. 4-({(7-chloro-benzo[d]thiazol-2-yl)[2-(4-methoxyphenyl)ethyl]amino}methyl)benzoic acid The titled compound was prepared in accordance with the same procedures as in Example 1, using 2-chloro-7-chlorobenzo[d]thiazole instead of 2-chloro-7-fluorobenzo[d]thiazole used in Step 3 of Example 1.

LCMS (m/z) 453 (M+H)+;

$^1$H NMR (400 MHz, CDCl$_3$) 8.05 (d, J=8.08 Hz, 2H), 7.46 (d, J=8.08 Hz, 1H), 7.34 (br d, J=8.08 Hz, 2H), 7.23 (s, 1H), 7.00-7.15 (m, 3H), 6.85 (d, J=8.34 Hz, 2H), 4.71 (s, 2H), 3.79 (s, 3H), 3.68 (br t, J=7.45 Hz, 2H), 2.96 (br t, J=7.33 Hz, 2H)

Example 84. 4-({(6-chloro-benzo[d]thiazol-2-yl)[2-(4-methoxyphenyl)ethyl]amino}methyl)benzoic acid The titled compound was prepared in accordance with the same procedures as in Example 1, using 2-chloro-6-chlorobenzo[d]thiazole instead of 2-chloro-7-fluorobenzo[d]thiazole used in Step 3 of Example 1.

LCMS (m/z) 453 (M+H)+;

$^1$H NMR (400 MHz, CDCl$_3$) 8.04 (d, J=8.34 Hz, 2H), 7.57 (d, J=2.27 Hz, 1H), 7.48 (d, J=8.59 Hz, 1H), 7.33 (d, J=8.34 Hz, 2H), 7.27 (d, J=2.27 Hz, 1H), 7.04-7.15 (m, 2H), 6.78-6.90 (m, 2H), 4.71 (s, 2H), 3.79 (s, 3H), 3.66 (t, J=7.45 Hz, 2H), 2.94 (t, J=7.45 Hz, 2H)

Example 85. 4-({(5-chloro-benzo[d]thiazol-2-yl)[2-(4-methoxyphenyl)ethyl]amino}methyl)benzoic acid The titled compound was prepared in accordance with the same procedures as in Example 1, using 2-chloro-5-chlorobenzo[d]thiazole instead of 2-chloro-7-fluorobenzo[d]thiazole used in Step 3 of Example 1.

LCMS (m/z) 453 (M+H)+;

$^1$H NMR (400 MHz, CDCl$_3$) 7.99-8.10 (m, J=8.08 Hz, 2H), 7.57 (d, J=2.02 Hz, 1H), 7.49 (d, J=8.59 Hz, 1H), 7.30-7.40 (m, J=8.08 Hz, 2H), 7.01-7.16 (m, 3H), 6.78-6.90 (m, 2H), 4.71 (s, 2H), 3.79 (s, 3H), 3.58-3.74 (m, 2H), 2.94 (t, J=7.45 Hz, 2H)

Example 86. 4-({(5,6-difluorobenzo[d]thiazol-2-yl)[2-(4-methoxyphenyl)ethyl]amino}methyl)benzoic acid The titled compound was prepared in accordance with the same procedures as in Example 1, using 2-chloro-5,6-difluorobenzo[d]thiazole instead of 2-chloro-7-fluorobenzo[d]thiazole used in Step 3 of Example 1.

LCMS (m/z) 455.1 (M+H)+;

$^1$H NMR (400 MHz, CDCl$_3$) 8.05 (d, J=8.08 Hz, 2H), 7.27-7.43 (m, 4H), 6.99-7.24 (m, 2H), 6.84 (d, J=8.34 Hz, 2H), 4.69 (s, 2H), 3.79 (s, 3H), 3.65 (br t, J=7.33 Hz, 2H), 2.93 (br t, J=7.45 Hz, 2H)

Example 87. 4-{[[2-(4-methoxyphenyl)ethyl](5,6,7-trifluorobenzo[d]thiazol-2-yl)amino]methyl}benzoic acid The titled compound was prepared in accordance with the same procedures as in Example 1, using 2-chloro-5,6,7-trifluorobenzo[d]thiazole instead of 2-chloro-7-fluorobenzo[d]thiazole used in Step 3 of Example 1.

LCMS (m/z) 473.1 (M+H)+;

$^1$H NMR (400 MHz, CDCl$_3$) 8.05 (d, J=8.08 Hz, 2H), 7.28-7.53 (m, 2H), 7.00-7.25 (m, 3H), 6.85 (d, J=8.34 Hz, 2H), 4.69 (s, 2H), 3.79 (s, 3H), 3.66 (br t, J=7.33 Hz, 2H), 2.94 (br t, J=7.33 Hz, 2H)

Example 88. 4-({(6-chloro-7-fluorobenzo[d]thiazol-2-yl)[2-(4-methoxyphenyl)ethyl]amino}methyl)benzoic acid The titled compound was prepared in accordance with the same procedures as in Example 1, using 2,6-dichloro-7-fluorobenzo[d]thiazole instead of 2-chloro-7-fluorobenzo[d]thiazole used in Step 3 of Example 1.

LCMS (m/z) 471.1 (M+H)+;

$^1$H NMR (400 MHz, CDCl$_3$) 8.05 (d, J=8.08 Hz, 2H), 7.28-7.41 (m, 4H), 6.99-7.25 (m, 2H), 6.85 (d, J=8.34 Hz, 2H), 4.71 (s, 2H), 3.79 (s, 3H), 3.67 (br t, J=7.20 Hz, 2H), 2.95 (br t, J=7.20 Hz, 2H)

Example 89. 4-{[[2-(4-methoxyphenyl)ethyl](7-trifluoromethyl-benzo[d]thiazol-2-yl)amino]methyl}benzoic acid The titled compound was prepared in accordance with the same procedures as in Example 1, using 2-chloro-7-trifluoromethylbenzo[d]thiazole instead of 2-chloro-7-fluorobenzo[d]thiazole used in Step 3 of Example 1.

LCMS (m/z) 487.1 (M+H)+;
$^1$H NMR (400 MHz, CDCl$_3$) 8.05 (br d, J=8.08 Hz, 2H), 7.72 (br d, J=8.08 Hz, 1H), 7.28-7.52 (m, 4H), 7.00-7.25 (m, 2H), 6.85 (br d, J=8.59 Hz, 2H), 4.74 (s, 2H), 3.79 (s, 3H), 3.69 (br t, J=7.20 Hz, 2H), 2.96 (br t, J=7.33 Hz, 2H)

Example 90. 4-({(6,7-difluorobenzo[d]thiazol-2-yl)-[2-(4-methoxyphenyl)ethyl]amino}methyl)benzoic acid The titled compound was prepared in accordance with the same procedures as in Example 1, using 2-chloro-6,7-difluorobenzo[d]thiazole instead of 2-chloro-7-fluorobenzo[d]thiazole used in Step 3 of Example 1.

LCMS (m/z) 455.1 (M+H)+;
$^1$H NMR (400 MHz, CDCl$_3$) 8.05 (d, J=7.58 Hz, 2H), 7.28-7.45 (m, 3H), 7.00-7.25 (m, 3H), 6.85 (d, J=8.34 Hz, 2H), 4.70 (s, 2H), 4.12 (d, J=7.33 Hz, 1H), 3.79 (s, 3H), 3.66 (br t, J=7.45 Hz, 2H), 2.95 (br t, J=7.45 Hz, 2H), 2.12 (s, 1H), 2.05 (s, 1H), 1.26 (t, J=7.07 Hz, 2H)

Example 91. 4-({(5-bromo-benzo[d]thiazol-2-yl)[2-(4-methoxyphenyl)ethyl]amino}methyl)benzoic acid The titled compound was prepared in accordance with the same procedures as in Example 1, using 2-chloro-5-bromobenzo[d]thiazole instead of 2-chloro-7-fluorobenzo[d]thiazole used in Step 3 of Example 1.

LCMS (m/z) 499.1 (M+H)+;
$^1$H NMR (400 MHz, CDCl$_3$) 8.04 (m, 2H), 7.73 (s, 1H), 7.44 (m, 1H), 7.34 (m, 2H), 7.20 (m, 1H), 7.10 (m, 2H), 6.84 (d, J=8.08 Hz, 2H), 4.71 (s, 2H), 3.79 (s, 2H), 3.67 (m, 2H), 2.95 (m, 2H)

Example 92. 4-({(6-fluorobenzo[d]thiazol-2-yl)[2-(4-methoxyphenyl)ethyl]amino}methyl)benzoic acid The titled compound was prepared in accordance with the same procedures as in Example 1, using 2-chloro-6-fluorobenzo[d]thiazole instead of 2-chloro-7-fluorobenzo[d]thiazole used in Step 3 of Example 1.

LCMS (m/z) 437.1 (M+H)+;
$^1$H NMR (400 MHz, CDCl$_3$) 8.04 (m, 2H), 7.50 (m, 2H), 7.29-7.40 (m, 3H), 6.99-7.25 (m, 3H), 6.84 (m, 2H), 4.71 (s, 2H), 3.79 (s, 3H), 3.65 (m, 2H), 2.94 (m, 2H)

Example 93. 4-({(5,7-difluorobenzo[d]thiazol-2-yl)[2-(4-methoxyphenyl)ethyl]amino}methyl)benzoic acid The titled compound was prepared in accordance with the same procedures as in Example 1, using 2-chloro-5,7-difluorobenzo[d]thiazole instead of 2-chloro-7-fluorobenzo[d]thiazole used in Step 3 of Example 1.

LCMS (m/z) 455.1 (M+H)+;
$^1$H NMR (400 MHz, CDCl$_3$) 8.05 (m, 2H), 7.27-7.52 (m, 3H), 7.00-7.25 (m, 3H), 6.85 (m, 2H), 6.62 (m, 1H), 4.71 (s, 2H), 3.79 (s, 3H), 3.67 (m, 2H), 2.95 (m, 2H)

Example 94. 4-({(7-fluoro-6-methyl-benzo[d]thiazol-2-yl)[2-(4-methoxyphenyl)ethyl]amino}methyl)benzoic acid The titled compound was prepared in accordance with the same procedures as in Example 1, using 2-chloro-7-fluoro-6-methylbenzo[d]thiazole instead of 2-chloro-7-fluorobenzo[d]thiazole used in Step 3 of Example 1.

LCMS (m/z) 451.1 (M+H)+;
$^1$H NMR (400 MHz, CDCl$_3$) 8.03 (d, J=8.08 Hz, 3H), 7.28-7.54 (m, 3H), 6.99-7.25 (m, 3H), 6.84 (d, J=8.34 Hz, 2H), 4.71 (s, 2H), 3.79 (s, 3H), 3.66 (br t, J=7.58 Hz, 2H), 2.95 (br t, J=7.58 Hz, 3H), 2.33 (s, 3H)

Example 95. 4-({(4,6-difluorobenzo[d]thiazol-2-yl)[2-(4-methoxyphenyl)ethyl]amino}methyl)benzoic acid The titled compound was prepared in accordance with the same procedures as in Example 1, using 2-chloro-4,6-difluorobenzo[d]thiazole instead of 2-chloro-7-fluorobenzo[d]thiazole used in Step 3 of Example 1.

LCMS (m/z) 455.1 (M+H)+;
$^1$H NMR (400 MHz, CDCl$_3$) 8.05 (m, 2H), 7.28-7.56 (m, 3H), 7.00-7.25 (m, 3H), 6.74-6.97 (m, 3H), 4.72 (s, 2H), 3.79 (s, 3H), 3.66 (m, 2H), 2.94 (m, 2H)

Example 96. 4-({[2-(4-methoxyphenyl)ethyl](7-methyl-benzo[d]thiazol-2-yl)amino}methyl)benzoic acid The titled compound was prepared in accordance with the same procedures as in Example 1, using 2-chloro-7-methylbenzo[d]thiazole instead of 2-chloro-7-fluorobenzo[d]thiazole used in Step 3 of Example 1.

$^1$H NMR (400 MHz, CDCl$_3$) 7.68-7.90 (m, 2H), 7.38 (br d, J=7.83 Hz, 1H), 7.16 (br t, J=7.71 Hz, 1H), 6.98 (br d, J=8.08 Hz, 4H), 6.78-6.86 (m, 1H), 6.73 (br d, J=7.83 Hz, 2H), 4.48 (br s, 2H), 3.68 (s, 3H), 3.46-3.65 (m, 2H), 2.80 (br t, J=7.07 Hz, 2H), 2.37 (s, 3H)

Example 97. 4-({[2-(4-methoxyphenyl)ethyl](6-methyl-benzo[d]thiazol-2-yl)amino}methyl)benzoic acid The titled compound was prepared in accordance with the same procedures as in Example 1, using 2-chloro-6-methylbenzo[d]thiazole instead of 2-chloro-7-fluorobenzo[d]thiazole used in Step 3 of Example 1.

$^1$H NMR (400 MHz, CDCl$_3$) 8.02 (d, J=7.83 Hz, 2H), 7.49 (d, J=8.34 Hz, 1H), 7.41 (s, 1H), 7.32 (d, J=7.83 Hz, 2H), 7.04-7.14 (m, 3H), 6.83 (d, J=7.58 Hz, 2H), 5.64 (br s, 1H), 4.71 (s, 2H), 3.78 (s, 3H), 3.65 (br t, J=7.45 Hz, 2H), 2.94 (br t, J=7.33 Hz, 2H), 2.40 (s, 3H)

Example 98. 4-({[2-(4-methoxyphenyl)ethyl](5-methyl-benzo[d]thiazol-2-yl)amino}methyl)benzoic acid The titled compound was prepared in accordance with the same procedures as in Example 1, using 2-chloro-5-methylbenzo[d]thiazole instead of 2-chloro-7-fluorobenzo[d]thiazole used in Step 3 of Example 1.

$^1$H NMR (400 MHz, CDCl$_3$) 8.03 (br d, J=7.58 Hz, 2H), 7.44 (d, J=8.08 Hz, 1H), 7.33 (br d, J=7.83 Hz, 2H), 7.24 (s, 1H), 7.11 (br d, J=7.58 Hz, 2H), 6.91 (br d, J=7.33 Hz, 1H), 6.84 (br d, J=7.33 Hz, 2H), 4.72 (s, 2H), 3.79 (s, 3H), 3.68 (br t, J=7.33 Hz, 2H), 2.96 (br t, J=7.33 Hz, 2H), 2.46 (s, 3H), 1.26 (s, 1H)

Example 99. 4-(1-{(5,7-difluorobenzo[d]thiazol-2-yl)[2-(4-methoxyphenyl)ethyl]amino}ethyl)benzoic acid The titled compound was prepared in accordance with the same procedures as in Example 52, using 2-chloro-5,7-difluorobenzo[d]thiazole instead of 2-chloro-7-fluorobenzo[d]thiazole used in Step 3 of Example 52.

LCMS (m/z) 469 (M+H)+;

$^1$H NMR (600 MHz, CDCl$_3$) 8.09 (br d, J=8.22 Hz, 2H), 7.49 (br d, J=8.22 Hz, 2H), 7.13 (br d, J=9.39 Hz, 1H), 7.00 (br d, J=8.22 Hz, 2H), 6.81 (br d, J=8.22 Hz, 2H), 6.63 (br t, J=9.39 Hz, 1H), 5.78 (br s, 1H), 3.77 (s, 3H), 3.41-3.52 (m, 1H), 3.29-3.41 (m, 1H), 2.88 (dt, J=5.58, 12.18 Hz, 1H), 2.57-2.69 (m, 1H), 1.71 (d, J=6.46 Hz, 3H)

Example 100. 4-(1-{(5,6-difluorobenzo[d]thiazol-2-yl)[2-(4-methoxyphenyl)ethyl]amino}ethyl)benzoic acid The titled compound was prepared in accordance with the same procedures as in Example 52, using 2-chloro-5,6-difluorobenzo[d]thiazole instead of 2-chloro-7-fluorobenzo[d]thiazole used in Step 3 of Example 52.

LCMS (m/z) 469 (M+H)+;

$^1$H NMR (600 MHz, CDCl$_3$) 8.08 (d, J=8.22 Hz, 2H), 7.48 (d, J=8.22 Hz, 2H), 7.33-7.44 (m, 2H), 7.00 (d, J=8.22 Hz, 2H), 6.81 (d, J=8.22 Hz, 2H), 5.73 (br d, J=7.04 Hz, 1H), 3.77 (s, 3H), 3.41-3.49 (m, 1H), 3.29-3.39 (m, 1H), 2.82-2.91 (m, 1H), 2.58-2.68 (m, 1H), 1.69 (d, J=7.04 Hz, 3H)

Example 101. 4-(1-{[2-(4-methoxyphenyl)ethyl](5,6,7-trifluorobenzo[d]thiazol-2-yl)amino}ethyl)benzoic acid The titled compound was prepared in accordance with the same procedures as in Example 52, using 2-chloro-5,6,7-trifluorobenzo[d]thiazole instead of 2-chloro-7-fluorobenzo[d]thiazole used in Step 3 of Example 52.

LCMS (m/z) 487 (M+H)+;

$^1$H NMR (600 MHz, CDCl$_3$) 8.10 (d, J=8.22 Hz, 2H), 7.48 (d, J=8.22 Hz, 2H), 7.20 (br dd, J=5.58, 10.27 Hz, 1H), 7.00 (d, J=8.80 Hz, 2H), 6.81 (d, J=8.80 Hz, 2H), 5.71 (br s, 1H), 3.78 (s, 3H), 3.41-3.52 (m, 1H), 3.30-3.41 (m, 1H), 2.87 (dt, J=5.87, 12.03 Hz, 1H), 2.57-2.67 (m, 1H), 1.80 (br d, J=7.63 Hz, 1H), 1.70 (d, J=6.46 Hz, 3H)

Example 102. 4-(1-{(6-chloro-7-fluorobenzo[d]thiazol-2-yl)[2-(4-methoxyphenyl)ethyl]amino}ethyl)benzoic acid The titled compound was prepared in accordance with the same procedures as in Example 52, using 2,6-dichloro-7-fluorobenzo[d]thiazole instead of 2-chloro-7-fluorobenzo[d]thiazole used in Step 3 of Example 52.

LCMS (m/z) 485 (M+H)+;

$^1$H NMR (600 MHz, CDCl$_3$) 8.10 (d, J=8.22 Hz, 2H), 7.48 (d, J=8.22 Hz, 2H), 7.20 (br dd, J=5.58, 10.27 Hz, 1H), 7.00 (d, J=8.80 Hz, 2H), 6.81 (d, J=8.80 Hz, 2H), 5.71 (br s, 1H), 3.78 (s, 3H), 3.41-3.52 (m, 1H), 3.30-3.41 (m, 1H), 2.87 (dt, J=5.87, 12.03 Hz, 1H), 2.57-2.67 (m, 1H), 1.80 (br d, J=7.63 Hz, 1H), 1.70 (d, J=6.46 Hz, 3H)

Example 103. 4-(1-{(5-bromo-benzo[d]thiazol-2-yl)[2-(4-methoxyphenyl)ethyl]amino}ethyl)benzoic acid The titled compound was prepared in accordance with the same procedures as in Example 52, using 2-chloro-5-bromobenzo[d]thiazole instead of 2-chloro-7-fluorobenzo[d]thiazole used in Step 3 of Example 52.

LCMS (m/z) 512 (M+H)+;

$^1$H NMR (600 MHz, CDCl$_3$) 8.08 (d, J=8.22 Hz, 2H), 7.75 (s, 1H), 7.44-7.53 (m, 3H), 7.17-7.25 (m, 1H), 6.97-7.04 (m, J=8.22 Hz, 2H), 6.76-6.86 (m, J=8.22 Hz, 2H), 5.77 (br s, 1H), 3.77 (s, 3H), 3.41-3.51 (m, 1H), 3.27-3.40 (m, 1H), 2.87 (dt, J=5.58, 12.18 Hz, 1H), 2.58-2.69 (m, 1H), 1.70 (brd, J=7.04 Hz, 3H)

Example 104. 4-(1-{(6,7-difluorobenzo[d]thiazol-2-yl)[2-(4-methoxyphenyl)ethyl]amino}ethyl)benzoic acid The titled compound was prepared in accordance with the same procedures as in Example 52, using 2-chloro-6,7-difluorobenzo[d]thiazole instead of 2-chloro-7-fluorobenzo[d]thiazole used in Step 3 of Example 52.

LCMS (m/z) 469 (M+H)+;

$^1$H NMR (600 MHz, CDCl$_3$) 8.08 (d, J=8.22 Hz, 2H), 7.45-7.52 (m, J=8.22 Hz, 2H), 7.29 (d, J=9.00 Hz, 1H), 7.12-7.18 (m, 1H), 6.98-7.03 (m, J=8.22 Hz, 2H), 6.78-6.84 (m, 2H), 5.74 (br d, J=6.46 Hz, 1H), 3.77 (s, 3H), 3.43-3.52 (m, 2H), 3.30-3.40 (m, 1H), 2.88 (dt, J=5.87, 12.33 Hz, 1H), 2.64 (dt, J=4.70, 12.03 Hz, 1H), 1.70 (d, J=7.04 Hz, 3H)

Example 105. 4-(1-{(7-fluoro-6-methyl-benzo[d]thiazol-2-yl)[2-(4-methoxyphenyl)ethyl]amino}ethyl)benzoic acid The titled compound was prepared in accordance with the same procedures as in Example 52, using 2-chloro-7-fluoro-6-methylbenzo[d]thiazole instead of 2-chloro-7-fluorobenzo[d]thiazole used in Step 3 of Example 52.

LCMS (m/z) 465 (M+H)+;

$^1$H NMR (600 MHz, CDCl$_3$) 8.07 (d, J=8.22 Hz, 2H), 7.48 (d, J=8.22 Hz, 2H), 7.30 (d, J=8.22 Hz, 1H), 7.12 (t, J=7.92 Hz, 1H), 7.01 (d, J=8.80 Hz, 2H), 6.81 (d, J=8.80 Hz, 2H), 5.79 (br d, J=6.46 Hz, 1H), 3.77 (s, 3H), 3.42-3.50 (m, 1H), 3.29-3.38 (m, 1H), 2.85-2.94 (m, 1H), 2.60-2.69 (m, 1H), 2.34 (s, 3H), 2.05 (s, 1H), 1.69 (d, J=7.04 Hz, 3H)

Example 106. 4-(1-{[2-(4-methoxyphenyl)ethyl][7-(trifluoromethyl)-benzo[d]thiazol-2-yl]amino}ethyl)benzoic acid The titled compound was prepared in accordance with the same procedures as in Example 52, using 2-chloro-7-trifluoromethylbenzo[d]thiazole instead of 2-chloro-7-fluorobenzo[d]thiazole used in Step 3 of Example 52.

LCMS (m/z) 501 (M+H)+;

$^1$H NMR (600 MHz, CDCl$_3$) 8.08 (d, J=8.22 Hz, 2H), 7.75 (d, J=7.63 Hz, 1H), 7.49 (d, J=8.22 Hz, 2H), 7.39-7.44 (m, 1H), 7.35-7.39 (m, 1H), 7.01 (d, J=8.22 Hz, 2H), 6.81 (d, J=8.22 Hz, 2H), 5.81 (br s, 1H), 3.77 (s, 3H), 3.44-3.54 (m, 1H), 3.34-3.43 (m, 1H), 2.84-2.94 (m, 1H), 2.61-2.69 (m, 1H), 1.71 (d, J=7.04 Hz, 3H)

Example 107. 4-(1-{(5-chloro-benzo[d]thiazol-2-yl)[2-(4-methoxyphenyl)ethyl]amino}ethyl)benzoic acid The titled compound was prepared in accordance with the same procedures as in Example 52, using 2,5-dichlorobenzo

[d]thiazole instead of 2-chloro-7-fluorobenzo[d]thiazole used in Step 3 of Example 52.

LCMS (m/z) 467 (M+H)+;
$^1$H NMR (600 MHz, CDCl$_3$) 8.08 (d, J=8.22 Hz, 2H), 7.60 (s, 1H), 7.52 (d, J=8.22 Hz, 1H), 7.48 (d, J=8.22 Hz, 2H), 7.07 (dd, J=1.47, 8.51 Hz, 1H), 7.01 (d, J=8.80 Hz, 2H), 6.81 (d, J=8.22 Hz, 2H), 5.78 (br d, J=6.46 Hz, 1H), 3.74-3.81 (m, 3H), 3.42-3.51 (m, 1H), 3.29-3.40 (m, 1H), 2.87 (dt, J=5.87, 12.33 Hz, 1H), 2.64 (dt, J=4.99, 12.18 Hz, 1H), 1.70 (d, J=7.04 Hz, 3H)

Example 108. 4-(1-{(6-chloro-benzo[d]thiazol-2-yl)[2-(4-methoxyphenyl)ethyl]amino}ethyl)benzoic acid The titled compound was prepared in accordance with the same procedures as in Example 52, using 2,6-dichlorobenzo[d]thiazole instead of 2-chloro-7-fluorobenzo[d]thiazole used in Step 3 of Example 52.

LCMS (m/z) 467 (M+H)+;
$^1$H NMR (600 MHz, CDCl$_3$) 8.08 (br d, J=8.22 Hz, 2H), 7.60 (s, 1H), 7.43-7.53 (m, 3H), 7.28 (d, J=8.76 Hz, 1H), 7.00 (d, J=8.22 Hz, 2H), 6.77-6.83 (m, 2H), 5.77 (br d, J=7.04 Hz, 1H), 3.77 (s, 3H), 3.41-3.49 (m, 1H), 3.29-3.39 (m, 1H), 2.83-2.92 (m, 1H), 2.58-2.68 (m, 1H), 1.69 (d, J=7.04 Hz, 3H)

Example 109. 4-(1-{(7-chloro-benzo[d]thiazol-2-yl)[2-(4-methoxyphenyl)ethyl]amino}ethyl)benzoic acid The titled compound was prepared in accordance with the same procedures as in Example 52, using 2,7-dichlorobenzo[d]thiazole instead of 2-chloro-7-fluorobenzo[d]thiazole used in Step 3 of Example 52.

LCMS (m/z) 467 (M+H)+;
$^1$H NMR (600 MHz, CDCl$_3$) 8.08 (d, J=7.63 Hz, 1H), 8.04-8.06 (m, 1H), 7.49 (d, J=8.22 Hz, 3H), 7.26-7.29 (m, 1H), 7.08 (d, J=8.22 Hz, 1H), 6.97-7.04 (m, J=8.22 Hz, 2H), 6.75-6.88 (m, J=8.22 Hz, 2H), 5.81 (br s, 1H), 3.77 (s, 3H), 3.41-3.52 (m, 1H), 3.30-3.41 (m, 1H), 2.90 (dt, J=5.87, 12.33 Hz, 1H), 2.62-2.71 (m, 1H), 1.70 (d, J=7.04 Hz, 3H)

Example 110. 4-(1-{[2-(4-methoxyphenyl)ethyl](7-methyl-benzo[d]thiazol-2-yl)amino}ethyl)benzoic acid The titled compound was prepared in accordance with the same procedures as in Example 52, using 2-chloro-7-methylbenzo[d]thiazole instead of 2-chloro-7-fluorobenzo[d]thiazole used in Step 3 of Example 52.

LCMS (m/z) 447 (M+H)+;
$^1$H NMR (600 MHz, CDCl$_3$) 8.07 (d, J=8.22 Hz, 2H), 7.43-7.54 (m, 3H), 7.26-7.30 (m, 1H), 7.02 (d, J=8.22 Hz, 2H), 6.92 (d, J=7.63 Hz, 1H), 6.81 (d, J=8.80 Hz, 2H), 5.85 (br d, J=6.46 Hz, 1H), 3.77 (s, 3H), 3.42-3.53 (m, 1H), 3.30-3.42 (m, 1H), 2.90 (dt, J=5.87, 12.33 Hz, 1H), 2.63-2.73 (m, 1H), 2.49 (s, 3H), 1.69 (d, J=7.04 Hz, 3H)

Example 111. 4-(1-{[2-(4-methoxyphenyl)ethyl](6-methyl-benzo[d]thiazol-2-yl)amino}ethyl)benzoic acid The titled compound was prepared in accordance with the same procedures as in Example 52, using 2-chloro-6-methylbenzo[d]thiazole instead of 2-chloro-7-fluorobenzo[d]thiazole used in Step 3 of Example 52.

LCMS (m/z) 447 (M+H)+;
$^1$H NMR (600 MHz, CDCl$_3$) 8.06 (d, J=8.22 Hz, 2H), 7.46-7.53 (m, 3H), 7.45 (s, 1H), 7.14 (d, J=8.22 Hz, 1H), 7.01 (d, J=8.22 Hz, 2H), 6.80 (d, J=8.22 Hz, 2H), 5.81 (br d, J=7.04 Hz, 1H), 3.77 (s, 3H), 3.39-3.49 (m, 1H), 3.27-3.38 (m, 1H), 2.84-2.93 (m, 1H), 2.59-2.70 (m, 1H), 2.42 (s, 3H), 1.68 (d, J=7.04 Hz, 3H)

Example 112. 4-(1-{[2-(4-methoxyphenyl)ethyl](5-methyl-benzo[d]thiazol-2-yl)amino}ethyl)benzoic acid The titled compound was prepared in accordance with the same procedures as in Example 52, using 2-chloro-5-methylbenzo[d]thiazole instead of 2-chloro-7-fluorobenzo[d]thiazole used in Step 3 of Example 52.

LCMS (m/z) 447 (M+H)+;
$^1$H NMR (600 MHz, CDCl$_3$) 8.07 (d, J=8.22 Hz, 2H), 7.44-7.55 (m, 4H), 7.01 (d, J=8.80 Hz, 2H), 6.94 (d, J=8.22 Hz, 1H), 6.80 (d, J=8.22 Hz, 2H), 5.82 (br d, J=6.46 Hz, 1H), 3.77 (s, 3H), 3.41-3.52 (m, 1H), 3.25-3.38 (m, 1H), 2.82-2.95 (m, 1H), 2.61-2.70 (m, 1H), 2.43 (s, 3H), 1.68 (d, J=7.04 Hz, 3H)

Example 113. 4-(1-{(5-fluorobenzo[d]thiazol-2-yl)[2-(4-methoxyphenyl)ethyl]amino}ethyl)benzoic acid The titled compound was prepared in accordance with the same procedures as in Example 52, using 2-chloro-5-fluorobenzo[d]thiazole instead of 2-chloro-7-fluorobenzo[d]thiazole used in Step 3 of Example 52.

LCMS (m/z) 451 (M+H)+;
$^1$H NMR (600 MHz, CDCl$_3$) 8.08 (d, J=8.22 Hz, 2H), 7.46-7.56 (m, 3H), 7.35 (dd, J=2.64, 7.92 Hz, 1H), 6.97-7.08 (m, 3H), 6.81 (d, J=8.80 Hz, 2H), 5.76 (q, J=7.04 Hz, 1H), 3.77 (s, 3H), 3.40-3.50 (m, 1H), 3.28-3.39 (m, 1H), 2.83-2.92 (m, 1H), 2.60-2.70 (m, 1H), 1.69 (d, J=7.04 Hz, 3H)

Example 114. 4-(1-{(4,6-difluorobenzo[d]thiazol-2-yl)[2-(4-methoxyphenyl)ethyl]amino}ethyl)benzoic acid The titled compound was prepared in accordance with the same procedures as in Example 52, using 2-chloro-4,6-difluorobenzo[d]thiazole instead of 2-chloro-7-fluorobenzo[d]thiazole used in Step 3 of Example 52.

LCMS (m/z) 469 (M+H)+;
$^1$H NMR (600 MHz, CDCl$_3$) 8.09 (d, J=8.22 Hz, 2H), 7.49 (d, J=7.63 Hz, 2H), 7.16 (br d, J=7.04 Hz, 1H), 7.01 (d, J=8.22 Hz, 2H), 6.87 (br t, J=9.98 Hz, 1H), 6.81 (d, J=8.80 Hz, 2H), 5.81 (br d, J=6.46 Hz, 1H), 3.77 (s, 3H), 3.41-3.52 (m, 1H), 3.28-3.41 (m, 1H), 2.87 (dt, J=5.87, 12.03 Hz, 1H), 2.64 (dt, J=4.70, 12.33 Hz, 1H), 1.70 (d, J=7.04 Hz, 3H)

Example 115. 4-({(6-bromo-benzo[d]thiazol-2-yl)[2-(4-methoxyphenyl)ethyl]amino}methyl)benzoic acid The titled compound was prepared in accordance with the same procedures as in Example 1, using 2-chloro-6-bromobenzo[d]thiazole instead of 2-chloro-7-fluorobenzo[d]thiazole used in Step 3 of Example 1.

$^1$H NMR (400 MHz, CDCl$_3$) 8.04 (d, J=8.34 Hz, 2H), 7.70 (s, 1H), 7.42 (q, J=8.59 Hz, 2H), 7.33 (d, J=8.08 Hz,

2H), 7.04-7.14 (m, J=8.34 Hz, 2H), 6.78-6.89 (m, J=8.34 Hz, 2H), 4.71 (s, 2H), 3.78 (s, 3H), 3.66 (br t, J=7.45 Hz, 2H), 2.93 (t, J=7.33 Hz, 2H)

Example 116. 4-(1-{(6-bromo-benzo[d]thiazol-2-yl)[2-(4-methoxyphenyl)ethyl]amino}ethyl)benzoic acid The titled compound was prepared in accordance with the same procedures as in Example 52, using 2-chloro-6-bromobenzo[d]thiazole instead of 2-chloro-7-fluorobenzo[d]thiazole used in Step 3 of Example 52.
LCMS (m/z) 512 (M+H)+;
$^1$H NMR (400 MHz, CDCl$_3$) 8.08 (d, J=8.59 Hz, 2H), 7.74 (d, J=1.77 Hz, 1H), 7.37-7.53 (m, 4H), 6.94-7.05 (m, J=8.59 Hz, 2H), 6.74-6.84 (m, J=8.59 Hz, 2H), 5.68-5.83 (m, 1H), 3.77 (s, 3H), 3.28-3.52 (m, 2H), 2.76-2.94 (m, 1H), 2.55-2.72 (m, 1H), 1.69 (d, J=7.07 Hz, 3H)

Example 117. 2-{(4-carboxybenzyl)[2-(4-methoxyphenyl)ethyl]amino}benzo[d]thiazole-6-carboxylic acid The titled compound was prepared in accordance with the same procedures as in Example 1, using 2-chloro-6-hydroxycarbonylbenzo[d]thiazole instead of 2-chloro-7-fluorobenzo[d]thiazole used in Step 3 of Example 1.
$^1$H NMR (400 MHz, DMSO-d$_6$) 12.76 (brs, 2H), 8.36 (s, 1H), 7.94 (d, 2H), 7.88 (d, 1H), 7.51 (d, 1H), 7.44 (d, 2H), 7.19 (d, 2H), 6.87 (d, 2H), 4.87 (s, 2H), 3.71 (m, 5H), 2.93-2.90 (m, 2H).

Example 118. 2-{(4-carboxybenzyl)[2-(4-methoxyphenyl)ethyl]amino}benzo[d]thiazole-7-carboxylic acid The titled compound was prepared in accordance with the same procedures as in Example 1, using 2-chloro-7-hydroxycarbonylbenzo[d]thiazole instead of 2-chloro-7-fluorobenzo[d]thiazole used in Step 3 of Example 1.
$^1$H NMR (400 MHz, DMSO-d$_6$) 13.04 (brs, 1H), 7.94 (m, 2H), 7.71 (m, 2H), 7.47-7.42 (m, 3H), 7.20 (m, 2H), 6.89 (m, 2H), 4.86 (s, 2H), 3.80-3.72 (m, 5H), 2.93 (m, 2H)

Example 119. 4-({[2-(4-methoxyphenyl)ethyl][6-(trifluoromethyl)benzo[d]thiazol-2-yl]amino}methyl)benzoic acid The titled compound was prepared in accordance with the same procedures as in Example 1, using 2-chloro-6-trifluoromethylbenzo[d]thiazole instead of 2-chloro-7-fluorobenzo[d]thiazole used in Step 3 of Example 1.
LCMS (m/z) 487.1 (M+H)+;
$^1$H NMR (400 MHz, CDCl$_3$) 8.05 (br d, J=8.08 Hz, 2H), 7.86 (s, 1H), 7.51-7.66 (m, 2H), 7.34 (br d, J=7.83 Hz, 2H), 7.26 (s, 1H), 7.10 (br d, J=8.59 Hz, 2H), 6.84 (br d, J=8.34 Hz, 2H), 4.73 (s, 2H), 3.79 (s, 3H), 3.69 (br t, J=7.20 Hz, 3H), 2.95 (br t, J=7.45 Hz, 2H)

Example 120. 4-({[2-(4-methoxyphenyl)ethyl][5-(trifluoromethyl)benzo[d]thiazol-2-yl]amino}methyl)benzoic acid The titled compound was prepared in accordance with the same procedures as in Example 1, using 2-chloro-5-trifluoromethylbenzo[d]thiazole instead of 2-chloro-7-fluorobenzo[d]thiazole used in Step 3 of Example 1.
LCMS (m/z) 487.1 (M+H)+

Example 121. 4-({[7-fluoro-6-(trifluoromethyl)benzo[d]thiazol-2-yl][2-(4-methoxyphenyl)ethyl]amino}methyl)benzoic acid The titled compound was prepared in accordance with the same procedures as in Example 1, using 2-chloro-7-fluoro-6-trifluoromethylbenzo[d]thiazole instead of 2-chloro-7-fluorobenzo[d]thiazole used in Step 3 of Example 1.
LCMS (m/z) 505.2 (M+H)+

Example 122. 4-(1-{(5,7-difluorobenzo[d]thiazol-2-yl)[2-(3-fluoro-4-methoxyphenyl)ethyl]amino}ethyl)benzoic acid The titled compound was prepared in accordance with the same procedures as in Example 52, using 2-chloro-5,7-difluorobenzo[d]thiazole instead of 2-chloro-7-fluorobenzo[d]thiazole used in Step 3 of Example 52.
LCMS (m/z) 487.1 (M+H)+;
$^1$H NMR (400 MHz, CDCl$_3$) 8.10 (m, 2H), 7.48 (m, 2H), 7.13 (d, J=9.60 Hz, 1H), 6.72-6.98 (m, 3H), 6.64 (m, 1H), 5.71 (m, 1H), 3.85 (s, 3H), 3.32-3.58 (m, 2H), 2.74-3.02 (m, 1H), 2.51-2.74 (m, 1H), 1.54-1.82 (m, 3H)

Example 123. 4-(1-{[2-(4-methoxyphenyl)ethyl][6-(trifluoromethyl)benzo[d]thiazol-2-yl]amino}ethyl)benzoic acid The titled compound was prepared in accordance with the same procedures as in Example 52, using 2-chloro-6-trifluoromethylbenzo[d]thiazole instead of 2-chloro-7-fluorobenzo[d]thiazole used in Step 3 of Example 52.
LCMS (m/z) 501.2 (M+H)+

Example 124. 4-(1-{[2-(4-methoxyphenyl)ethyl][5-(trifluoromethyl)benzo[d]thiazol-2-yl]amino}ethyl)benzoic acid The titled compound was prepared in accordance with the same procedures as in Example 52, using 2-chloro-5-trifluoromethylbenzo[d]thiazole instead of 2-chloro-7-fluorobenzo[d]thiazole used in Step 3 of Example 52.
LCMS (m/z) 501.2 (M+H)+

Example 125. 4-(1-{[7-fluoro-6-(trifluoromethyl)benzo[d]thiazol-2-yl][2-(4-methoxyphenyl)ethyl]amino}ethyl)benzoic acid The titled compound was prepared in accordance with the same procedures as in Example 52, using 2-chloro-7-fluoro-6-trifluoromethylbenzo[d]thiazole instead of 2-chloro-7-fluorobenzo[d]thiazole used in Step 3 of Example 52.
LCMS (m/z) 519.2 (M+H)+

Test Example 1: Inhibitory Activity Against the Binding Between the KRS Protein and the Laminin Receptor (LR)

Figure 2:
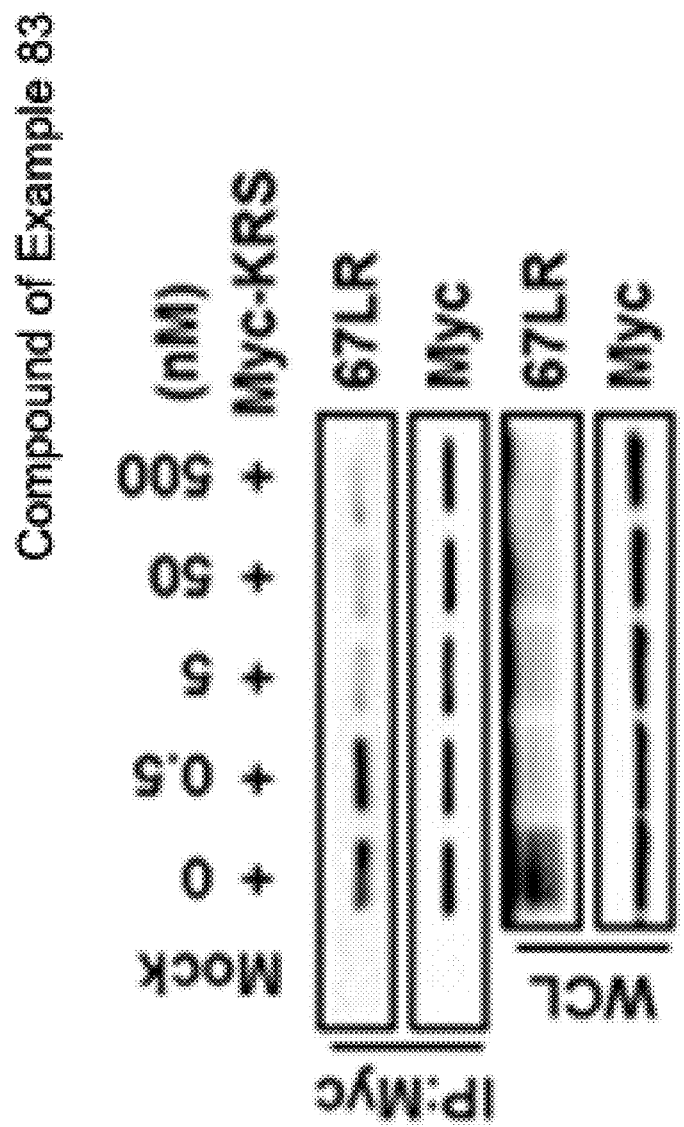
Figure 3:
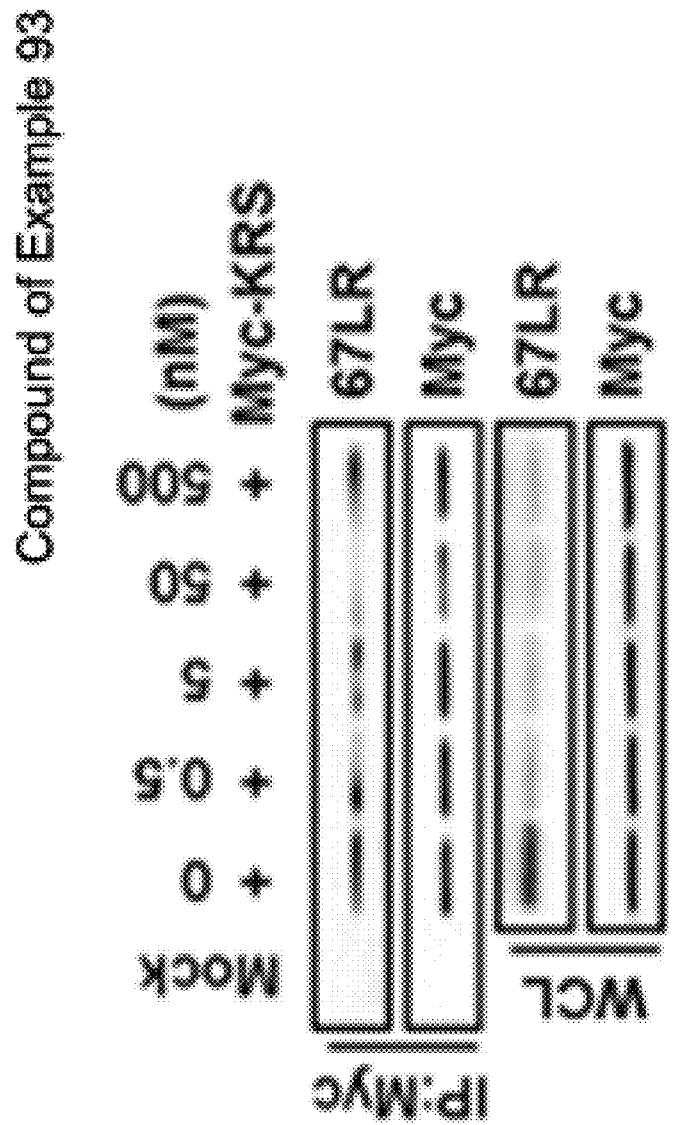

The effects of the compounds of the present invention on the binding between the KRS protein and the laminin receptor (LR) were evaluated according to the co-immunoprecipitation method. A Myc-tagged KRS expression vector was transfected into human lung cancer cell line A549 (Korean Cell Line Bank) using the lipofectamine reagent (Invitrogen), followed by culturing in a RPMI1640 medium supplemented with 10% FBS for 24 hours. The transfected A549 cell line was inoculated into the serum-free RPMI 1640 medium, treated with laminin (10 μg/mL), and then cultured for 2 hours. The cell line was treated with the compounds of the present invention (i.e., the compounds of Examples 1, 83, and 93) in predetermined concentrations, cultured for 6 hours, and then washed with cold phosphate buffered saline (PBS) three times. The obtained cells were lysed with a RIPA buffer (Sigma) and then reacted with an anti-myc antibody (Santacruz) containing agarose at 4° C. for 2 hours. The inhibitions against the binding between the KRS protein and the LR protein were determined through SDS-PAGE and western blotting. The results obtained by measuring the amounts of the precipitated LR protein bound to myc-KRS protein are shown in FIGS. 1 to 3.

When KRS and LR are combined each other, co-precipitated LR protein with myc-KRS is also present and can be confirmed by Western blotting using LR antibody (Santacruz). As can be seen from the results of FIGS. 1 to 3, the bindings between the KRS protein and the LR protein were weakened in a concentration-dependent manner according to the treatments of the compounds of the present invention, which can be confirmed by the blurring of the LR band of Western blotting. Therefore, it can be seen that the compounds of the present invention strongly inhibit the binding between KRS and LR.

Test Example 2: Cell Migration Assay

Cell migration was measured with a 24-well transwell having a polycarbonate membrane (8.0 μm pore size, Costar) at the bottom of the upper chamber. Each lower well was treated with laminin (10 μg/mL) and test compounds in predetermined concentrations (0.39~100 μM) along with a serum-free RPMI1640 medium. A549 cells (Korean Cell Line Bank) were suspended in a serum-free RPMI1640 medium at a concentration of $1 \times 10^6$ cells/mL and then the test compounds were added thereto at the indicated concentrations. Each resulting solution (100 μL) was added to the upper chamber. The cells were cultured at 37° C. for 6 hours in a $CO_2$ incubator. The upper chamber was taken out and then the cells were fixed with PBS containing 70% methyl alcohol for 10 minutes, followed by washing with PBS twice. The cells were stained with hematoxylin (Sigma) for 10 minutes and then washed with distilled water. The non-migrated cells were removed from the upper portion of the polycarbonate membrane with a cotton swab. The membranes were excised and separated from the chamber, and then mounted to a slide using a gel mount reagent (Biomeda, USA). The migrated cells (attached to the lower face of the membrane) were counted at three randomly selected sites under a microscope (×20). The cell counting was performed with the Image J program. From the counted cell numbers, each $IC_{50}$ value was calculated by non-linear regression curve fit using the "GraphPad Prism" program. The results are shown in Table 1 below.

TABLE 1

| Example No. | Inhibitory activity against cell migration |
| --- | --- |
| 1 | +++ |
| 2 | +++ |
| 3 | + |
| 4 | ++ |
| 5 | + |
| 6 | +++ |
| 7 | ++ |
| 8 | + |
| 9 | +++ |
| 10 | ++ |
| 11 | ++ |
| 12 | +++ |
| 13 | +++ |
| 14 | + |
| 15 | +++ |
| 16 | + |
| 17 | + |
| 18 | ++ |
| 19 | +++ |
| 20 | +++ |
| 21 | +++ |
| 22 | ++ |
| 23 | + |
| 24 | ++ |
| 25 | + |
| 26 | +++ |
| 27 | ++ |
| 28 | +++ |
| 29 | +++ |
| 30 | + |
| 31 | ++ |
| 32 | +++ |
| 33 | + |
| 34 | + |
| 35 | + |
| 36 | + |
| 37 | + |
| 38 | + |
| 39 | + |
| 40 | + |
| 41 | + |
| 42 | + |
| 43 | +++ |
| 44 | + |
| 45 | +++ |
| 46 | + |
| 47 | + |
| 48 | +++ |
| 49 | +++ |
| 50 | +++ |
| 51 | +++ |
| 52 | +++ |
| 53 | +++ |
| 54 | + |
| 55 | + |
| 56 | + |
| 57 | + |
| 58 | + |
| 59 | + |
| 60 | +++ |
| 61 | +++ |
| 62 | + |
| 63 | +++ |
| 64 | +++ |
| 65 | +++ |
| 66 | +++ |
| 67 | +++ |
| 68 | +++ |
| 69 | + |
| 70 | + |
| 71 | + |
| 72 | + |
| 73 | + |
| 74 | + |
| 75 | + |
| 76 | + |
| 77 | +++ |
| 78 | +++ |
| 79 | +++ |
| 80 | +++ |
| 81 | +++ |

TABLE 1-continued

| Example No. | Inhibitory activity against cell migration |
|---|---|
| 82 | +++ |
| 83 | +++ |
| 84 | +++ |
| 85 | +++ |
| 86 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | +++ |
| 110 | + |
| 111 | + |
| 112 | + |
| 113 | + |
| 114 | + |
| 115 | + |
| 116 | + |
| 117 | + |
| 118 | + |
| 119 | + |
| 120 | +++ |
| 121 | + |
| 122 | +++ |
| 124 | +++ |

+++: $IC_{50} < 1\ \mu M$,
++: $1\ \mu M < IC_{50} < 10\ \mu M$,
+: $IC_{50} > 10\ \mu M$

The cells are pulled by laminin residing in the lower chamber and then passed through the polycarbonate membrane, so as to attach to the lower face of the membrane. As shown in Table 1, the compounds of the present invention efficiently inhibit the cell migration, thereby showing excellent activity against a disease associated with cancer cell metastasis.

The invention claimed is:

1. A compound of Formula 1 or its pharmaceutically acceptable salt:

<Formula 1>

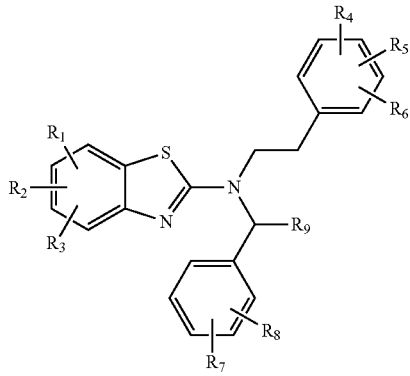

wherein, $R_1$, $R_2$, and $R_3$ are, independently of each other, hydrogen; a halogen group; a nitro group; an amino group; a $C_1$~$C_6$ alkyl group optionally substituted with halogen; or a hydroxycarbonyl group (with the proviso that $R_1$, $R_2$, and $R_3$ are not hydrogen at the same time), $R_4$, $R_5$, and $R_6$ are, independently of each other, hydrogen; a halogen group; a $C_1$~$C_6$ alkyl group; a $C_1$~$C_6$ alkoxy group optionally substituted with $C_3$~$C_6$ cycloalkyl; a $C_1$~$C_6$ alkylsulfanyl group; or a mono- or di-$C_1$~$C_6$ alkylamino group, $R_7$ and $R_8$ are, independently of each other, hydrogen; a hydroxy group; a halogen group; or a hydroxycarbonyl group (with the proviso that $R_7$ and $R_8$ are not hydrogen at the same time), and $R_9$ is hydrogen or a $C_1$~$C_6$ alkyl group.

2. The compound or its pharmaceutically acceptable salt of claim 1, wherein $R_1$, $R_2$, and $R_3$ are, independently of each other, hydrogen; or a halogen group (with the proviso that $R_1$, $R_2$, and $R_3$ are not hydrogen at the same time), $R_4$, $R_5$, and $R_6$ are, independently of each other, hydrogen; a halogen group; or a $C_1$~$C_6$ alkoxy group (with the proviso that $R_4$, $R_5$, and $R_6$ are not hydrogen at the same time), $R_7$ and $R_8$ are, independently of each other, hydrogen; or a hydroxycarbonyl group (with the proviso that $R_7$ and $R_8$ are not hydrogen at the same time), and $R_9$ is hydrogen or a $C_1$~$C_6$ alkyl group.

3. The compound or its pharmaceutically acceptable salt of claim 1, which is selected from the group consisting of:
4-({(7-fluorobenzo[d]thiazol-2-yl)[2-(4-methoxyphenyl) ethyl]amino}methyl)benzoic acid;
4-(((2-chlorophenylethyl)(7-fluorobenzo[d]thiazol-2-yl) amino)methyl)benzoic acid;
4-({(7-fluorobenzo[d]thiazol-2-yl)[2-(3-fluorophenyl) ethyl]amino}methyl)benzoic acid;
4-{[[2-(4-chlorophenyl)ethyl](7-fluorobenzo[d]thiazol-2-yl)amino]methyl}benzoic acid;
4-{[[2-(3-chlorophenyl)ethyl](7-fluorobenzo[d]thiazol-2-yl)amino]methyl}benzoic acid;
4-(((7-fluorobenzo[d]thiazol-2-yl)(4-methylphenylethyl) amino)methyl)benzoic acid;
4-({(7-fluorobenzo[d]thiazol-2-yl)[2-(3-methoxyphenyl) ethyl]amino}methyl)benzoic acid;

4-({(7-fluorobenzo[d]thiazol-2-yl)[2-(4-fluorophenyl)ethyl]amino}methyl)benzoic acid;
4-{[[2-(4-ethoxyphenyl)ethyl](7-fluorobenzo[d]thiazol-2-yl)amino]methyl}benzoic acid;
4-({(7-fluorobenzo[d]thiazol-2-yl)[2-(4-propoxyphenyl)ethyl]amino}methyl)benzoic acid;
4-({(7-fluorobenzo[d]thiazol-2-yl)[2-(4-isopropoxyphenyl)ethyl]amino}methyl)benzoic acid;
4-{[(7-fluorobenzo[d]thiazol-2-yl){2-[4-(methylsulfanyl)phenyl]ethyl}amino]methyl}benzoic acid;
4-{[(7-fluorobenzo[d]thiazol-2-yl){2-[3-(methylsulfanyl)phenyl]ethyl}amino]methyl}benzoic acid;
4-({[2-(2,5-dimethoxyphenyl)ethyl](7-fluorobenzo[d]thiazol-2-yl)amino}methyl)benzoic acid;
4-({[2-(3,4-dimethoxyphenyl)ethyl](7-fluorobenzo[d]thiazol-2-yl)amino}methyl)benzoic acid;
4-({(7-fluorobenzo[d]thiazol-2-yl)[2-(2-methoxyphenyl)ethyl]amino}methyl)benzoic acid;
4-({(7-fluorobenzo[d]thiazol-2-yl)[2-(3-methylphenyl)ethyl]amino}methyl)benzoic acid;
4-({(7-fluorobenzo[d]thiazol-2-yl)[2-(4-isobutoxyphenyl)ethyl]amino}methyl)benzoic acid;
4-{[[2-(4-cyclopropylmethoxyphenyl)ethyl](7-fluorobenzo[d]thiazol-2-yl)amino]methyl}benzoic acid;
4-{[(7-fluorobenzo[d]thiazol-2-yl){2-[4-(methylamino)phenyl]ethyl}amino]methyl}benzoic acid;
4-{[{2-[4-(dimethylamino)phenyl]ethyl}(7-fluorobenzo[d]thiazol-2-yl)amino]methyl}benzoic acid;
4-{[(7-fluorobenzo[d]thiazol-2-yl)(2-phenylethyl)amino]methyl}benzoic acid;
4-{[[2-(4-cyclohexylmethoxyphenyl)ethyl]-(7-fluorobenzo[d]thiazol-2-yl)amino]methyl}benzoic acid;
4-{[[2-(4-cyclobutylmethoxyphenyl)ethyl]-(7-fluorobenzo[d]thiazol-2-yl)amino]methyl}benzoic acid;
4-({[2-(4-ethoxy-3-methoxyphenyl)ethyl](7-fluorobenzo[d]thiazol-2-yl)amino}methyl)benzoic acid;
4-({(7-fluorobenzo[d]thiazol-2-yl)[2-(2-fluoro-4-methoxyphenyl)ethyl]amino}methyl)benzoic acid;
4-({[2-(2,4-dimethoxyphenyl)ethyl](7-fluorobenzo[d]thiazol-2-yl)amino}methyl)benzoic acid;
4-({(7-fluorobenzo[d]thiazol-2-yl)[2-(3-fluoro-4-methoxyphenyl)ethyl]amino}methyl)benzoic acid;
4-({[2-(3-chloro-4-methoxyphenyl)ethyl](7-fluorobenzo[d]thiazol-2-yl)amino}methyl)benzoic acid;
4-{[[2-(4-sec-butoxyphenyl)ethyl](7-fluorobenzo[d]thiazol-2-yl)amino]methyl}benzoic acid;
4-{[[2-(4-ethylaminophenyl)ethyl](7-fluorobenzo[d]thiazol-2-yl)amino]methyl}benzoic acid;
4-({[2-(4-ethylphenyl)ethyl](7-fluorobenzo[d]thiazol-2-yl)amino}methyl)benzoic acid;
4-{[(7-fluorobenzo[d]thiazol-2-yl){2-[4-(propan-2-yl)phenyl]ethyl}amino]methyl}benzoic acid;
4-({[2-(2,3-difluorophenyl)ethyl](7-fluorobenzo[d]thiazol-2-yl)amino}methyl)benzoic acid;
4-({[2-(2,5-difluorophenyl)ethyl](7-fluorobenzo[d]thiazol-2-yl)amino}methyl)benzoic acid;
4-({(7-fluorobenzo[d]thiazol-2-yl)[2-(3,4,5-trifluorophenyl)ethyl]amino}methyl)benzoic acid;
4-({[2-(3-bromo-4-methoxyphenyl)ethyl](7-fluorobenzo[d]thiazol-2-yl)amino}methyl)benzoic acid;
4-({[2-(2,4-dichlorophenyl)ethyl](7-fluorobenzo[d]thiazol-2-yl)amino}methyl)benzoic acid;
4-({[2-(2,4-difluorophenyl)ethyl](7-fluorobenzo[d]thiazol-2-yl)amino}methyl)benzoic acid;
4-({(7-fluorobenzo[d]thiazol-2-yl)[2-(2-methoxyphenyl)ethyl]amino}methyl)benzoic acid;
4-({(7-fluorobenzo[d]thiazol-2-yl)[2-(2-fluorophenyl)ethyl]amino}methyl)benzoic acid;
4-({(7-fluorobenzo[d]thiazol-2-yl)[2-(3-methoxyphenyl)ethyl]amino}methyl)benzoic acid;
4-({[2-(2,3-difluoro-4-methoxyphenyl)ethyl](7-fluorobenzo[d]thiazol-2-yl)amino}methyl)benzoic acid;
4-{[(7-fluorobenzo[d]thiazol-2-yl){2-[4-methoxy-2-methyl-5-(propan-2-yl)phenyl]ethyl}amino]methyl}benzoic acid;
4-({[2-(2,5-difluoro-4-methoxyphenyl)ethyl](7-fluorobenzo[d]thiazol-2-yl)amino}methyl)benzoic acid;
4-({[2-(2-chloro-4-methoxyphenyl)ethyl](7-fluorobenzo[d]thiazol-2-yl)amino}methyl)benzoic acid;
4-({(7-fluorobenzo[d]thiazol-2-yl)[2-(4-methoxy-2,3-dimethylphenyl)ethyl]amino}methyl)benzoic acid;
4-({(7-fluorobenzo[d]thiazol-2-yl)[2-(4-methoxy-2,5-dimethylphenyl)ethyl]amino}methyl)benzoic acid;
4-({(7-fluorobenzo[d]thiazol-2-yl)[2-(4-methoxy-3-methylphenyl)ethyl]amino}methyl)benzoic acid;
4-({(7-fluorobenzo[d]thiazol-2-yl)[2-(4-methoxy-2-methylphenyl)ethyl]amino}methyl)benzoic acid;
4-({[2-(2,6-difluoro-4-methoxyphenyl)ethyl](7-fluorobenzo[d]thiazol-2-yl)amino}methyl)benzoic acid;
4-(1-{(7-fluorobenzo[d]thiazol-2-yl)[2-(4-methoxyphenyl)ethyl]amino}ethyl)benzoic acid;
4-(1-{(7-fluorobenzo[d]thiazol-2-yl)[2-(4-methoxyphenyl)ethyl]amino}propyl)benzoic acid;
4-(1-{(7-fluorobenzo[d]thiazol-2-yl)[2-(3-fluoro-4-methoxyphenyl)ethyl]amino}ethyl)benzoic acid;
4-(1-{[2-(3-bromo-4-methoxyphenyl)ethyl](7-fluorobenzo[d]thiazol-2-yl)amino}ethyl)benzoic acid;
4-(1-{[2-(2,4-difluorophenyl)ethyl](7-fluorobenzo[d]thiazol-2-yl)amino}ethyl)benzoic acid;
4-(1-{[2-(2,3-difluorophenyl)ethyl](7-fluorobenzo[d]thiazol-2-yl)amino}ethyl)benzoic acid;
4-(1-{(7-fluorobenzo[d]thiazol-2-yl)[2-(3,4,5-trifluorophenyl)ethyl]amino}ethyl)benzoic acid;
4-(1-{[2-(2,4-dichlorophenyl)ethyl](7-fluorobenzo[d]thiazol-2-yl)amino}ethyl)benzoic acid;
4-(1-{[2-(2,3-difluoro-4-methoxyphenyl)ethyl](7-fluorobenzo[d]thiazol-2-yl)amino}ethyl)benzoic acid;
4-(1-{[2-(2,5-difluoro-4-methoxyphenyl)ethyl](7-fluorobenzo[d]thiazol-2-yl)amino}ethyl)benzoic acid;
4-{1-[(7-fluorobenzo[d]thiazol-2-yl){2-[4-methoxy-2-methyl-5-(propan-2-yl)phenyl]ethyl}amino]ethyl}benzoic acid;
4-(1-{(7-fluorobenzo[d]thiazol-2-yl)[2-(4-methoxy-2,3-dimethylphenyl)ethyl]amino}ethyl)benzoic acid;
4-(1-{(7-fluorobenzo[d]thiazol-2-yl)[2-(4-methoxy-2,5-dimethylphenyl)ethyl]amino}ethyl)benzoic acid;
4-(1-{(7-fluorobenzo[d]thiazol-2-yl)[2-(4-methoxy-3-methylphenyl)ethyl]amino}ethyl)benzoic acid;
4-(1-{(7-fluorobenzo[d]thiazol-2-yl)[2-(4-methoxy-2-methylphenyl)ethyl]amino}ethyl)benzoic acid;
4-(1-{[2-(2,6-difluoro-4-methoxyphenyl)ethyl](7-fluorobenzo[d]thiazol-2-yl)amino}ethyl)benzoic acid;
4-(1-{[2-(2,3-difluoro-4-methoxyphenyl)ethyl](7-fluorobenzo[d]thiazol-2-yl)amino}propyl)benzoic acid;
4-(1-{[2-(2,5-difluoro-4-methoxyphenyl)ethyl](7-fluorobenzo[d]thiazol-2-yl)amino}propyl)benzoic acid;
4-(1-{[2-(2-chloro-4-methoxyphenyl)ethyl](7-fluorobenzo[d]thiazol-2-yl)amino}propyl)benzoic acid;
4-(1-{(7-fluorobenzo[d]thiazol-2-yl)[2-(4-methoxy-2,3-dimethylphenyl)ethyl]amino}propyl)benzoic acid;
4-(1-{(7-fluorobenzo[d]thiazol-2-yl)[2-(4-methoxy-2,5-dimethylphenyl)ethyl]amino}propyl)benzoic acid;

4-(1-{(7-fluorobenzo[d]thiazol-2-yl)[2-(4-methoxy-3-methylphenyl)ethyl]amino}propyl)benzoic acid;
4-(1-{(7-fluorobenzo[d]thiazol-2-yl)[2-(4-methoxy-2-methylphenyl)ethyl]amino}propyl)benzoic acid;
4-(1-{[2-(2,6-difluoro-4-methoxyphenyl)ethyl](7-fluorobenzo[d]thiazol-2-yl)amino}propyl)benzoic acid;
4-{1-[(7-fluorobenzo[d]thiazol-2-yl){2-[4-methoxy-2-methyl-5-(propan-2-yl)phenyl]ethyl}amino]propyl}benzoic acid;
4-({(7-fluorobenzo[d]thiazol-2-yl)[2-(4-methoxyphenyl)ethyl]amino}methyl)-2-hydroxybenzoic acid;
3-chloro-4-({(7-fluorobenzo[d]thiazol-2-yl)[2-(4-methoxyphenyl)ethyl]amino}methyl)benzoic acid;
4-({[2-(4-methoxyphenyl)ethyl](6-nitro-benzo[d]thiazol-2-yl)amino}methyl)benzoic acid;
4-({[2-(4-methoxyphenyl)ethyl](7-nitro-benzo[d]thiazol-2-yl)amino}methyl)benzoic acid;
4-({(6-amino-benzo[d]thiazol-2-yl)[2-(4-methoxyphenyl)ethyl]amino}methyl)benzoic acid;
4-({(7-amino-benzo[d]thiazol-2-yl)[2-(4-methoxyphenyl)ethyl]amino}methyl)benzoic acid;
4-({(7-chloro-benzo[d]thiazol-2-yl)[2-(4-methoxyphenyl)ethyl]amino}methyl)benzoic acid;
4-({(6-chloro-benzo[d]thiazol-2-yl)[2-(4-methoxyphenyl)ethyl]amino}methyl)benzoic acid;
4-({(5-chloro-benzo[d]thiazol-2-yl)[2-(4-methoxyphenyl)ethyl]amino}methyl)benzoic acid;
4-({(5,6-difluorobenzo[d]thiazol-2-yl)[2-(4-methoxyphenyl)ethyl]amino}methyl)benzoic acid;
4-{[[2-(4-methoxyphenyl)ethyl](5,6,7-trifluorobenzo[d]thiazol-2-yl)amino]methyl}benzoic acid;
4-({(6-chloro-7-fluorobenzo[d]thiazol-2-yl)[2-(4-methoxyphenyl)ethyl]amino}methyl)benzoic acid;
4-{[[2-(4-methoxyphenyl)ethyl](7-trifluoromethyl-benzo[d]thiazol-2-yl)amino]methyl}benzoic acid;
4-({(6,7-difluorobenzo[d]thiazol-2-yl)-[2-(4-methoxyphenyl)ethyl]amino}methyl)benzoic acid;
4-({(5-bromo-benzo[d]thiazol-2-yl)[2-(4-methoxyphenyl)ethyl]amino}methyl)benzoic acid;
4-({(6-fluorobenzo[d]thiazol-2-yl)[2-(4-methoxyphenyl)ethyl]amino}methyl)benzoic acid;
4-({(5,7-difluorobenzo[d]thiazol-2-yl)[2-(4-methoxyphenyl)ethyl]amino}methyl)benzoic acid;
4-({(7-fluoro-6-methyl-benzo[d]thiazol-2-yl)[2-(4-methoxyphenyl)ethyl]amino}methyl)benzoic acid;
4-({(4,6-difluorobenzo[d]thiazol-2-yl)[2-(4-methoxyphenyl)ethyl]amino}methyl)benzoic acid;
4-({[2-(4-methoxyphenyl)ethyl](7-methyl-benzo[d]thiazol-2-yl)amino}methyl)benzoic acid;
4-({[2-(4-methoxyphenyl)ethyl](6-methyl-benzo[d]thiazol-2-yl)amino}methyl)benzoic acid;
4-({[2-(4-methoxyphenyl)ethyl](5-methyl-benzo[d]thiazol-2-yl)amino}methyl)benzoic acid;
4-(1-{(5,7-difluorobenzo[d]thiazol-2-yl)[2-(4-methoxyphenyl)ethyl]amino}ethyl)benzoic acid;
4-(1-{(5,6-difluorobenzo[d]thiazol-2-yl)[2-(4-methoxyphenyl)ethyl]amino}ethyl)benzoic acid;
4-(1-{[2-(4-methoxyphenyl)ethyl](5,6,7-trifluorobenzo[d]thiazol-2-yl)amino}ethyl)benzoic acid;
4-(1-{(6-chloro-7-fluorobenzo[d]thiazol-2-yl)[2-(4-methoxyphenyl)ethyl]amino}ethyl)benzoic acid;
4-(1-{(5-bromo-benzo[d]thiazol-2-yl)[2-(4-methoxyphenyl)ethyl]amino}ethyl)benzoic acid;
4-(1-{(6,7-difluorobenzo[d]thiazol-2-yl)[2-(4-methoxyphenyl)ethyl]amino}ethyl)benzoic acid;
4-(1-{(7-fluoro-6-methyl-benzo[d]thiazol-2-yl)[2-(4-methoxyphenyl)ethyl]amino}ethyl)benzoic acid;
4-(1-{[2-(4-methoxyphenyl)ethyl][7-(trifluoromethyl)-benzo[d]thiazol-2-yl]amino}ethyl)benzoic acid;
4-(1-{(5-chloro-benzo[d]thiazol-2-yl)[2-(4-methoxyphenyl)ethyl]amino}ethyl)benzoic acid;
4-(1-{(6-chloro-benzo[d]thiazol-2-yl)[2-(4-methoxyphenyl)ethyl]amino}ethyl)benzoic acid;
4-(1-{(7-chloro-benzo[d]thiazol-2-yl)[2-(4-methoxyphenyl)ethyl]amino}ethyl)benzoic acid;
4-(1-{[2-(4-methoxyphenyl)ethyl](7-methyl-benzo[d]thiazol-2-yl)amino}ethyl)benzoic acid;
4-(1-{[2-(4-methoxyphenyl)ethyl](6-methyl-benzo[d]thiazol-2-yl)amino}ethyl)benzoic acid;
4-(1-{[2-(4-methoxyphenyl)ethyl](5-methyl-benzo[d]thiazol-2-yl)amino}ethyl)benzoic acid;
4-(1-{(5-fluorobenzo[d]thiazol-2-yl)[2-(4-methoxyphenyl)ethyl]amino}ethyl)benzoic acid;
4-(1-{(4,6-difluorobenzo[d]thiazol-2-yl)[2-(4-methoxyphenyl)ethyl]amino}ethyl)benzoic acid;
4-({(6-bromo-benzo[d]thiazol-2-yl)[2-(4-methoxyphenyl)ethyl]amino}methyl)benzoic acid;
4-(1-{(6-bromo-benzo[d]thiazol-2-yl)[2-(4-methoxyphenyl)ethyl]amino}ethyl)benzoic acid;
2-{(4-carboxybenzyl)[2-(4-methoxyphenyl)ethyl]amino}benzo[d]thiazole-6-carboxylic acid;
2-{(4-carboxybenzyl)[2-(4-methoxyphenyl)ethyl]amino}benzo[d]thiazole-7-carboxylic acid;
4-({[2-(4-methoxyphenyl)ethyl][6-(trifluoromethyl)benzo[d]thiazol-2-yl]amino}methyl)benzoic acid;
4-({[2-(4-methoxyphenyl)ethyl][5-(trifluoromethyl)benzo[d]thiazol-2-yl]amino}methyl)benzoic acid;
4-({[7-fluoro-6-(trifluoromethyl)benzo[d]thiazol-2-yl][2-(4-methoxyphenyl)ethyl]amino}methyl)benzoic acid;
4-(1-{(5,7-difluorobenzo[d]thiazol-2-yl)[2-(3-fluoro-4-methoxyphenyl)ethyl]amino}ethyl)benzoic acid;
4-(1-{[2-(4-methoxyphenyl)ethyl][6-(trifluoromethyl)benzo[d]thiazol-2-yl]amino}ethyl)benzoic acid;
4-(1-{[2-(4-methoxyphenyl)ethyl][5-(trifluoromethyl)benzo[d]thiazol-2-yl]amino}ethyl)benzoic acid; and
4-(1-{[7-fluoro-6-(trifluoromethyl)benzo[d]thiazol-2-yl][2-(4-methoxyphenyl)ethyl]amino}ethyl)benzoic acid.

4. The compound or its pharmaceutically acceptable salt of claim 1, which is selected from the group consisting of:
4-({(7-fluorobenzo[d]thiazol-2-yl)[2-(4-methoxyphenyl)ethyl]amino}methyl)benzoic acid;
4-(((2-chlorophenylethyl)(7-fluorobenzo[d]thiazol-2-yl)amino)methyl)benzoic acid;
4-(((7-fluorobenzo[d]thiazol-2-yl)(4-methylphenylethyl)amino)methyl)benzoic acid;
4-{[[2-(4-ethoxyphenyl)ethyl](7-fluorobenzo[d]thiazol-2-yl)amino]methyl}benzoic acid;
4-{[(7-fluorobenzo[d]thiazol-2-yl){2-[4-(methylsulfanyl)phenyl]ethyl}amino]methyl}benzoic acid;
4-{[(7-fluorobenzo[d]thiazol-2-yl){2-[3-(methylsulfanyl)phenyl]ethyl}amino]methyl}benzoic acid;
4-({[2-(3,4-dimethoxyphenyl)ethyl](7-fluorobenzo[d]thiazol-2-yl)amino}methyl)benzoic acid;
4-{[[2-(4-cyclopropylmethoxyphenyl)ethyl](7-fluorobenzo[d]thiazol-2-yl)amino]methyl}benzoic acid;
4-{[(7-fluorobenzo[d]thiazol-2-yl){2-[4-(methylamino)phenyl]ethyl}amino]methyl}benzoic acid;
4-{[{2-[4-(dimethylamino)phenyl]ethyl}(7-fluorobenzo[d]thiazol-2-yl)amino]methyl}benzoic acid;
4-({(7-fluorobenzo[d]thiazol-2-yl)[2-(2-fluoro-4-methoxyphenyl)ethyl]amino}methyl)benzoic acid;
4-({(7-fluorobenzo[d]thiazol-2-yl)[2-(3-fluoro-4-methoxyphenyl)ethyl]amino}methyl)benzoic acid;

4-({[2-(3-chloro-4-methoxyphenyl)ethyl](7-fluorobenzo[d]thiazol-2-yl)amino}methyl)benzoic acid;
4-({[2-(4-ethylphenyl)ethyl](7-fluorobenzo[d]thiazol-2-yl)amino}methyl)benzoic acid;
4-({[2-(2,3-difluoro-4-methoxyphenyl)ethyl](7-fluorobenzo[d]thiazol-2-yl)amino}methyl)benzoic acid;
4-({[2-(2,5-difluoro-4-methoxyphenyl)ethyl](7-fluorobenzo[d]thiazol-2-yl)amino}methyl)benzoic acid;
4-({(7-fluorobenzo[d]thiazol-2-yl)[2-(4-methoxy-2,5-dimethylphenyl)ethyl]amino}methyl)benzoic acid;
4-({(7-fluorobenzo[d]thiazol-2-yl)[2-(4-methoxy-3-methylphenyl)ethyl]amino}methyl)benzoic acid;
4-({(7-fluorobenzo[d]thiazol-2-yl)[2-(4-methoxy-2-methylphenyl)ethyl]amino}methyl)benzoic acid;
4-({[2-(2,6-difluoro-4-methoxyphenyl)ethyl](7-fluorobenzo[d]thiazol-2-yl)amino}methyl)benzoic acid;
4-(1-{(7-fluorobenzo[d]thiazol-2-yl)[2-(4-methoxyphenyl)ethyl]amino}ethyl)benzoic acid;
4-(1-{(7-fluorobenzo[d]thiazol-2-yl)[2-(4-methoxyphenyl)ethyl]amino}propyl)benzoic acid;
4-(1-{[2-(2,3-difluoro-4-methoxyphenyl)ethyl](7-fluorobenzo[d]thiazol-2-yl)amino}ethyl)benzoic acid;
4-(1-{[2-(2,5-difluoro-4-methoxyphenyl)ethyl](7-fluorobenzo[d]thiazol-2-yl)amino}ethyl)benzoic acid;
4-(1-{(7-fluorobenzo[d]thiazol-2-yl)[2-(4-methoxy-2,3-dimethylphenyl)ethyl]amino}ethyl)benzoic acid;
4-(1-{(7-fluorobenzo[d]thiazol-2-yl)[2-(4-methoxy-2,5-dimethylphenyl)ethyl]amino}ethyl)benzoic acid;
4-(1-{(7-fluorobenzo[d]thiazol-2-yl)[2-(4-methoxy-3-methylphenyl)ethyl]amino}ethyl)benzoic acid;
4-(1-{(7-fluorobenzo[d]thiazol-2-yl)[2-(4-methoxy-2-methylphenyl)ethyl]amino}ethyl)benzoic acid;
4-(1-{[2-(2,6-difluoro-4-methoxyphenyl)ethyl](7-fluorobenzo[d]thiazol-2-yl)amino}ethyl)benzoic acid;
4-(1-{[2-(2,3-difluoro-4-methoxyphenyl)ethyl](7-fluorobenzo[d]thiazol-2-yl)amino}propyl)benzoic acid;
4-({(7-fluorobenzo[d]thiazol-2-yl)[2-(4-methoxyphenyl)ethyl]amino}methyl)-2-hydroxybenzoic acid;
3-chloro-4-({(7-fluorobenzo[d]thiazol-2-yl)[2-(4-methoxyphenyl)ethyl]amino}methyl)benzoic acid;
4-({[2-(4-methoxyphenyl)ethyl](6-nitro-benzo[d]thiazol-2-yl)amino}methyl)benzoic acid;
4-({[2-(4-methoxyphenyl)ethyl](7-nitro-benzo[d]thiazol-2-yl)amino}methyl)benzoic acid;
4-({(6-amino-benzo[d]thiazol-2-yl)[2-(4-methoxyphenyl)ethyl]amino}methyl)benzoic acid;
4-({(7-amino-benzo[d]thiazol-2-yl)[2-(4-methoxyphenyl)ethyl]amino}methyl)benzoic acid;
4-({(7-chloro-benzo[d]thiazol-2-yl)[2-(4-methoxyphenyl)ethyl]amino}methyl)benzoic acid;
4-({(6-chloro-benzo[d]thiazol-2-yl)[2-(4-methoxyphenyl)ethyl]amino}methyl)benzoic acid;
4-({(5-chloro-benzo[d]thiazol-2-yl)[2-(4-methoxyphenyl)ethyl]amino}methyl)benzoic acid;
4-({(5,6-difluorobenzo[d]thiazol-2-yl)[2-(4-methoxyphenyl)ethyl]amino}methyl)benzoic acid;
4-{[[2-(4-methoxyphenyl)ethyl](5,6,7-trifluorobenzo[d]thiazol-2-yl)amino]methyl}benzoic acid;
4-({(6-chloro-7-fluorobenzo[d]thiazol-2-yl)[2-(4-methoxyphenyl)ethyl]amino}methyl)benzoic acid;
4-{[[2-(4-methoxyphenyl)ethyl](7-trifluoromethyl-benzo[d]thiazol-2-yl)amino]methyl}benzoic acid;
4-({(6,7-difluorobenzo[d]thiazol-2-yl)-[2-(4-methoxyphenyl)ethyl]amino}methyl)benzoic acid;
4-({(5-bromo-benzo[d]thiazol-2-yl)[2-(4-methoxyphenyl)ethyl]amino}methyl)benzoic acid;
4-({(6-fluorobenzo[d]thiazol-2-yl)[2-(4-methoxyphenyl)ethyl]amino}methyl)benzoic acid;
4-({(5,7-difluorobenzo[d]thiazol-2-yl)[2-(4-methoxyphenyl)ethyl]amino}methyl)benzoic acid;
4-({(7-fluoro-6-methyl-benzo[d]thiazol-2-yl)[2-(4-methoxyphenyl)ethyl]amino}methyl)benzoic acid;
4-({(4,6-difluorobenzo[d]thiazol-2-yl)[2-(4-methoxyphenyl)ethyl]amino}methyl)benzoic acid;
4-(1-{(7-chloro-benzo[d]thiazol-2-yl)[2-(4-methoxyphenyl)ethyl]amino}ethyl)benzoic acid;
4-({[2-(4-methoxyphenyl)ethyl][5-(trifluoromethyl)benzo[d]thiazol-2-yl]amino}methyl)benzoic acid;
4-(1-{(5,7-difluorobenzo[d]thiazol-2-yl)[2-(3-fluoro-4-methoxyphenyl)ethyl]amino}ethyl)benzoic acid; and
4-(1-{[2-(4-methoxyphenyl)ethyl][5-(trifluoromethyl)benzo[d]thiazol-2-yl]amino}ethyl)benzoic acid.

5. The compound or its pharmaceutically acceptable salt of claim 1, which is selected from the group consisting of:
4-({(7-fluorobenzo[d]thiazol-2-yl)[2-(4-methoxyphenyl)ethyl]amino}methyl)benzoic acid;
4-({(7-chloro-benzo[d]thiazol-2-yl)[2-(4-methoxyphenyl)ethyl]amino}methyl)benzoic acid; and
4-({(5,7-difluorobenzo[d]thiazol-2-yl)[2-(4-methoxyphenyl)ethyl]amino}methyl)benzoic acid.

6. A pharmaceutical composition for treating a disease associated with cancer cell metastasis, comprising a therapeutically effective amount of the compound or its pharmaceutically acceptable salt according to claim 1; and a pharmaceutically acceptable carrier.

7. The pharmaceutical composition of claim 6, wherein the disease associated with cancer cell metastasis is selected from the group consisting of colon cancer, lung cancer, hepatic cancer, gastric cancer, esophageal cancer, pancreatic cancer, gallbladder cancer, kidney cancer, bladder cancer, prostate cancer, testicular cancer, cervical cancer, endometrial cancer, choriocarcinoma, ovarian cancer, breast cancer, thyroid cancer, brain tumor, head and neck cancer, malignant melanoma, lymphoma, and aplastic anemia.

8. An inhibitor against cancer cell metastasis, comprising a therapeutically effective amount of the compound or its pharmaceutically acceptable salt according to claim 1 as an active ingredient.

* * * * *